(12) United States Patent
Barry et al.

(10) Patent No.: US 9,745,636 B2
(45) Date of Patent: Aug. 29, 2017

(54) SWI5 GENE AS A DIAGNOSTIC TARGET FOR THE IDENTIFICATION OF FUNGAL AND YEAST SPECIES

(75) Inventors: Thomas Gerard Barry, Kinarva (IE); Majella Maher, Moycullen (IE); Terry James Smith, Galway (IE); Marcin Jankiewicz, Galway (IE); Louise O'Connor, Moycullen (IE); Nina Tuite, Galway (IE); Sinead Lahiff, Gort (IE)

(73) Assignee: National University of Ireland, Galway, Galway (IE)

(*) Notice: Subject to any disclaimer, the term of this patent is extended or adjusted under 35 U.S.C. 154(b) by 754 days.

(21) Appl. No.: 12/997,482

(22) PCT Filed: Jun. 15, 2009

(86) PCT No.: PCT/EP2009/057346
§ 371 (c)(1),
(2), (4) Date: May 5, 2011

(87) PCT Pub. No.: WO2009/150244
PCT Pub. Date: Dec. 17, 2009

(65) Prior Publication Data
US 2011/0212445 A1  Sep. 1, 2011

(30) Foreign Application Priority Data
Jun. 13, 2008 (IE) .................... 2008/0487

(51) Int. Cl.
*C12Q 1/68* (2006.01)

(52) U.S. Cl.
CPC ................ *C12Q 1/6895* (2013.01)

(58) Field of Classification Search
None
See application file for complete search history.

(56) References Cited

U.S. PATENT DOCUMENTS 7,504,490 B1 * 3/2009 Weinstock et al. .......... 536/23.1
2004/0219565 A1 * 11/2004 Kauppinen et al. ............ 435/6

OTHER PUBLICATIONS

Pan et al. (Mol. Cell Biol., 2000, 20(22):8364-8372).*
Nierman et al. (2005, vol. 438 (1151-1156), including supplemental documents).*
Lowe et al. (Nucleic Acids Research, 1990, 18(7):1757-1761).*
Fedorova et al., "Genomic Islands in the Pathogenic Filamentous Fungus Aspergillus Fumigatus," PLOS Genetics 4(4): 1-13 (2008).
Levdansky et al., "Coding Tandem Repeats Generate Diversity in Aspergillus Genes," Eukaryotic Cell 6(8):1380-1391 (2007).
MacCallum et al., "Different Consequences of ACE2 and SWI5 Gene Disruptions for Virulence of Pathogenic and Nonpathogenic Yeasts," Infection and Immunity 74(9): 5244-5248 (2006).
NCBI Reference Sequence: XM_001213836.1. "Aspergillus terreus NIH2624 conserved hypothetical protein (ATEG_04658) partial mRNA." (Nov. 23, 2012).
NCBI Reference Sequence: XM_001263336.1 "Neosartorya fischeri NRRL 181 C2H2 transcription factor (Swi5), putative (NFIA_066040) partial mRNA." (Nov. 23, 2012).
NCBI Reference Sequence: XM_001271124.1 "Aspergillus clavatus NRRL 1 C2H2 transcription factor (Swi5), putative (ACLA_039140), partial mRNA." (Nov. 23, 2012).
NCBI Reference Sequence: XM_001399797.1 "Aspergillus niger CBS 513.88 hypothetical protein (An02g07000) partial mRNA." (Nov. 23, 2012).
NCBI Reference Sequence: XM_00189776.1 "Aspergillus Oryzae RIB40 Hypothetical Protein Partial mRNA." (Nov. 23, 2012).
NCBI Reference Sequence: XM_657385.1. "Aspergillus nidulans FGSC A4 hypothetical protein AN4873.2 partial mRNA." (Nov. 23, 2012).
NCBI Reference Sequence XM_749401.1 "Aspergillus fumigatus Af293 C2H2 transcription factor (Swi5), putative (AFUA_3G11250), partial mRNA." (Nov. 23, 2012).
Rokas et al., "What Can Comparative Genomics Tell Us About Species Concepts in the Genus *Aspergillus*?" Studies in Mycology 59:11-17 (2007).
Stillman et al., "Characterization of a Transcription Factor Involved in Mother Cell Specific Transcription of the Yeast HO Gene," The EMBO Journal 7(2): 485-494 (1988).

* cited by examiner

*Primary Examiner* — Stephanie K Mummert
(74) *Attorney, Agent, or Firm* — Foley Lardner LLP; Antoinette F. Konski

(57) ABSTRACT

The invention relates to the SWI5 gene, the corresponding RNA, specific probes, primers and oligonucleotides related thereto and their use in diagnostic assays to detect and/or discriminate between fungal and yeast species.

13 Claims, 18 Drawing Sheets

Figure 1

SEQ ID NO 29

ATGTTAGCCAATCCACATAGTAATCTGCACGAGCGTTATCGACAACATCGTCGGC
AGATTTCAACCCCCAATGCGCTGGAAGCCGCCAAAGTTCCTACCCTTCCAGCACA
GGCATTGCAGCGAATCAATGCGCATCGCCGTGGACAGAGTCTCGACCAACGACCT
TTGCACGATGGGACCGTTTCCATTACTAACGCAACAGCAACTCAGCAGCACCAAA
TCCTTGCTGGAGGAGAACAGCATCCCCAATTCTCGCAATCGGCACATTTCCCCCA
GCACTCCTCTCCCATGCCCGTGATGCCTGAATGCCCGTCTTTGACCTCAGAAGAC
TTGCAAGCATTATCCAATTCTACCAGCAATGCGAATCATCCGGGCATGGCTTACA
TGAATTCGAGCTTCTTTGCTATGGGGAATCCGAGCTTGGGACTTCGACCAATGGA
TAACAATCTGAATCTGATGCAACAGCAACAGCAGCAAAATGCCCACGTCTCATGC
GTCAATAGCCTTGAGGGCCAAATCCTCGACAACGGTGCCTGGAATTTCTACCAGC
AAGGCCAGCTCCCTACGACGCTTCGGTCTCAAGTCAACAATCTTTCGGCCGATGG
GAGACGACAGTCTGTTCAGTCAGATATCACCCCCTCGCAACGACCACATACCCCC
AAGCAAGCAAATACGCACTACTTTCCCATAACGCCAGCGACAACTCCGTTTAAGA
AACCGGCGGAACTTGCTCAGTATAGTACGGACATGCAGTCCACCCCCACCAAGGA
GACAGGCCGCTCTGCACCCGCATCAGCCCAGTCGGTATACATGCAACGAGCCAAA
TCCCTCCAAGGAGTTGCGGGGTCTACCTTTTCCAACTCCAAAATCGAGATGCCCT
CCCCCCCGAACACGGCTTCATTTGAAATTGACAATTTTGATGCGTTTAGCAGTCA
GCAGGGTTCCAGTTTCGAGATTTCCGAGTCAGAGAATTTATCGCAGAGTCACTAT
GCCTCGTCGTCAGCAACCTCGTCCTTTCAATCCTCCCAGAGCTAGCCGCCATGC
CAAGCCCCGAAGACAATCACGAGAAGGCTCATAAGCTGCCCATCTTCCCTGCCGC
GTCCAATCGGCCAGCGCACAGGAAGGCGCTGAGTACCAGCTCCAGTTCCACCTTG
ACGAAACCCCGGCTCTCTCCAAGAGTGGCTTCAATTGATAGCCTTAACCTTGATG
CTAGGGTTCATGCTTCTATCAAAGAGACTGGGATCACCATCGATGAGATCGCCTC
CTACATCTCTGGCCCTGACCGGAGGATGGAAAGTGGGTTTGCCTTCACCCCGGC
TGCGAGCGGCGGTTCGGAAGAAAAGAAAATATCAAGTCCCACGTCCAAACCCACC
TTGGTGATCGCCAATATAAGTGTGATCATTGCAACAAGTGCTTCGTTCGTGGACA
TGACCTGAAGCGTCACGCCAAGATTCACACTGGAGACAAACCATATGAATGTCTT
TGTGGCAATGTATTCGCTAGGCACGATGCTCTGACTCGGCACAGACAACGAGGAA
TGTGCATCGGCGGTTACAAGGGTATTGTGCGCAAGACAACCAAGCGTGGCCGTCC
AAAGAAACATCGACCAGAGTTGGAGGAGAGACAGGATAAGGCAGCCAAGACACGC
CAGAGAGTCGCCGAAAAGTCATCCCATGACTCCTCGTCCGGGTGTGTTGATTCCC
CCAACTCGCCGCCTTCCGAAATCCTTGAAAATATGAGTCTTCACGGGGATCGAG
CCCTAAAGAGAATATGCCCGCGTTCATTCAGCCCAACTTTTCCTTGCCTCCATCG
GCGTTTACTTTCACGCCTCCTGCGTCTCCCCGACAGAGTCTTGGAAACCAGCCAT
CGCCCGCTCAGAGTCGCCGCTCACTCACGCCCAGTAGCGAGGATGAAATGCTGCC
TTTGTCTCCCTCCAAGCGCCCCCTCGAGAAGATCGTTGAAGAACCGAGCCTGCCT
TTCACTTCGAGTGCCGACCCATACACCGATATTGCTGCTCCACCGCGGAGCTGT
CTTCTCCACATACGGCTCCCACCTTGGCTGATTCGTCTCACGGCTCCGACCTCGA
TATTTTCATCAGCACGGATAGCTCCGCCAATTTCAAGCATGAATTTCCCGATCTG
AGTGACCCCGACATGGCCGCTTTCCCCGACTATGTCAATGGGTCTACCTTCGAAC
CCGGAATGGATCTGTTCTCGAGCAAGACATTCTCTGCCGGTACCTCGATGAACGA
GGACTTCTTTTCACTCCAATTCCAGGTTGATGATATGACCAAAGAATTCTTCATG
GACTGCTAG-2319bp

Figure 2

SEQ ID NOs 17, SEQ ID NOs 1, SEQ ID NOs 2

ATCGACAACATCGTCGGCACATTTCAACCCCCAATGCGCTGGAAGCCG**CCAAAGT
TCCTACCCTTCCAGCAC**AGGCATTGCAGCGAATCAATGCGCATCGCCGTGGACAG
AGTCTCGACCAACGACCTTTGCACGATGGGACCGTTTCCATTACTAACGCAACAG
CAACTCAGCAGCACCAAATCCTTGCTGGAGGAGAACAGCATCCCCAATTCTCGCA
ATCGGCACATTTCCCCCAGCACTCCTCTCCCATGCCCGTGATGCCTGAATGCCCG
TCTTTGACCTCAGAAGACTTGCAAGCATTATCCAATTCTACCAGCAATGCGAATC
ATCCGGGCATGGCTTACATGAATTCGAGCTTCTTTGCTATGGGGAATCCGAGCTT
GGGACTTCGACCAATGGATAACAATCTGAATCTGATGCAACAGCAACAGC

Figure 3

SEQ ID NO. 18, SEQ ID NO. 5, SEQ ID NO. 6

CGTGGACATGACCTGAAGCGTCACGCCAAGATTCACACTGGAGACAAACCATATG
AATGTCTTTGTGGCAATGTATTCGCTAGGCACGATGCT**CTGACTCGGCACAGACA
ACGAGGA**ATGTGCATCGGCGGTTACAAGGGTATTGTGCGCAAGACAACCAAGCGT
GGCCGTCCAAAGAAACATCGACCAGACTTGGAGGAGAGAC

```
GLAU543  : ----------AGCGATCTGAACTTATATCAGACAGC : 418
              g   c   c   t    a    A  TcaA cTgATgCAaca ca
                                  A TcaA cTgATgCAAaca ca
```

SWI5 GENE AS A DIAGNOSTIC TARGET FOR THE IDENTIFICATION OF FUNGAL AND YEAST SPECIES

CROSS-REFERENCE TO RELATED APPLICATIONS

This application claims the benefit under 35 U.S.C. §371 of PCT International Application No. PCT/EP2009/057346, filed Jun. 15, 2009, which in turn claims priority to Irish Application No. 2008/0487, filed Jun. 13, 2008, the contents of each which are hereby incorporated by reference in their entirety.

FIELD OF THE INVENTION

The present invention relates to nucleic acid primers and probes for use in the identification of one or more fungal and yeast species. More specifically the invention relates to the SWI5 gene, the corresponding RNA, specific probes, primers and oligonucleotides related thereto and their use in diagnostic assays to detect and/or discriminate between fungal and yeast species.

BACKGROUND TO THE INVENTION

Yeast and fungal infections represent a major cause of morbidity and mortality among immunocompromised patients. The number of immunocompromised patients at risk of yeast and fungal infection continues to increase each year, as does the spectrum of fungal and yeast agents causing disease. Mortality from fungal infections, particularly invasive fungal infections, is 30% or greater in certain risk groups. The array of available anti-fungal agents is growing; however, so too is the recognition of both intrinsic and emerging resistance to antifungal drugs. These factors are contributing to the increased need for cost containment in laboratory testing and have led to laboratory consolidation in testing procedures.

Invasive fungal infections are on the increase. In 2003, it was estimated that there were 9 million at risk patients of which 1.2 million developed infection. *Candida* spp. and *Aspergillus* spp. now rank as the most prominent pathogens infecting immunosupressed patients. In particular, infections are common in the urinary tract, the respiratory system and the bloodstream, at the site of insertion of stents, catheters and orthopaedic joints. Approximately, 10% of the known *Candida* spp. have been implicated in human infection. Invasive candidiasis occurs when candida enters the bloodstream and it is estimated to occur at a frequency of 8/100,000 population in the US with a mortality rate of 40%. *Candida albicans* is the 4$^{th}$ most common cause of bloodstream infection. Aspergillosis usually begins as a pulmonary infection that can progress to a life-threatening invasive infection in some patients and has a mortality rate of greater than 90%. Emerging mycoses agents include *Fusarium, Scedosporium, Zygomycetes* and *Trichosporon* spp. ("*Stakeholder Insight: Invasive fungal infections*", Datamonitor, January 2004).

Immunocompromised patients including transplant and surgical patients, neonates, cancer patients, diabetics and those with HIV/AIDs are at high risk of developing invasive fungal infections (Datamonitor report: Stakeholder opinion—Invasive fungal infections, options outweigh replacements 2004). A large number of severe cases of sepsis are reported each year. Despite improvements in its medical management, sepsis still constitutes one of the greatest challenges in intensive care medicine. Microorganisms (bacteria, fungi and yeast) responsible for causing sepsis are traditionally detected in hospital laboratories with the aid of microbiological culture methods with poor sensitivity (25-82%), which are very time-consuming, generally in taking from two to five days to complete, and up to eight days for the diagnosis of fungal infections. Definitive diagnosis of infection caused by yeasts or fungi is usually based on either, the recovery and identification of a specific agent from clinical specimens or microscopic demonstration of fungi with distinct morphological features. However, there are numerous cases where these methods fail to provide conclusive proof as to the infecting agent. In these instances, the detection of specific host antibody responses can be used, although again this can be affected by the immune status of the patient. Time is critical in the detection and identification of bloodstream infections typically caused by bacteria and fungi. Effective treatment depends on finding the source of infection and making appropriate decisions about antibiotics or antifungals quickly and efficiently. Only after pathogens are correctly identified can targeted therapy using a specific antibiotic or anti-fungal begin. Many physicians would like to see the development of better in vitro amplification and direct detection diagnostic techniques for the early diagnosis of yeast and fungi ("*Stakeholder Insight: Invasive fungal infections*", Datamonitor, January 2004). Recently Roche™ launched a real time PCR based assay (Septifast™), for the detection of bacterial, fungal and yeast DNA in clinical samples. Therefore, there is a clear need for the development of novel rapid diagnostic tests for clinically significant bacterial and fungal pathogens for bioanalysis applications in the clinical sector. This has led the current inventors to identify novel fungal and yeast nucleic acid targets for application in Nucleic Acid Diagnostics (NAD) tests. Fungal and yeast nucleic acid based diagnostics have focused heavily on the ribosomal RNA (rRNA) genes, RNA transcripts, and their associated DNA/RNA regions. The rRNA genes are highly conserved in all fungal species and they also contain divergent and distinctive intergenic transcribed spacer regions. Ribosomal rRNA comprises three genes: the large sub-unit gene (28S), the small sub-unit gene (18S) and the 5.8S gene. The 28S and 18S rRNA genes are separated by the 5.8S rRNA and two internal transcribed spacers (ITS1 and ITS2). Because the ITS region contains a high number of sequence polymorphisms, numerous researchers have concentrated their efforts on these as targets (Atkins and Clark, 2004). rRNA genes are also multicopy genes with >10 copies within the fungal genome.

A number of groups are working on developing new assays for fungal and yeast infections. US2004044193 relates to, amongst a number of other aspects, the transcription factor CaTEC1 of *Candida albicans*; inhibitors thereof, and methods for the diagnosis and therapy of diseases which are connected with a *Candida* infection; and also diagnostic and pharmaceutical compositions which contain the nucleotide sequences, proteins, host cells and/or antibodies. WO0183824 relates to hybridization assay probes and accessory oligonucleotides for detecting ribosomal nucleic acids from *Candida albicans* and/or *Candida dubliniensis*. US6017699 and U.S. Pat. No. 5,426,026 relate to a set of DNA primers, which can be used to amplify and speciate DNA from five medically important *Candida* species. U.S. Pat. No. 6,747,137 discloses sequences useful for diagnosis of *Candida* infections. EP 0422872 and U.S. Pat. No. 5,658,726 disclose probes based on 18S rRNA genes, and U.S. Pat. No. 5,958,693 discloses probes based on 28S rRNA, for diagnosis of a range of yeast and fungal species.

U.S. Pat. No. 6,017,366 describes sequences based on chitin synthase gene for use in nucleic acid based diagnostics for a range of Candida species. It is clear though, that development of faster, more accurate diagnostic methods are required, particularly in light of the selection pressure caused by modern anti-microbial treatments which give rise to increased populations of resistant virulent strains with mutated genome sequences. Methods that enable early diagnosis of microbial causes of infection enable the selection of a specific narrow spectrum antibiotic or antifungal to treat the infection (Datamonitor report: Stakeholder opinion—Invasive fungal infections, options outweigh replacements 2004; Datamonitor report: Stakeholder Opinion-Sepsis, under reaction to an overreaction, 2006).

SWI5 is a transcription factor that activates genes involved in mitosis/Gap 1 (interphase) switch and is expressed in G1 phase of the cell cycle (Butler and Thiele 1991; Aerne et al., 1998; Akamatsu et al., 2003; Ellermeier et al., 2004; MacCallum et al., 2006). There are 128 SWI5 sequences available in NCBI GenBank database including sequences for 6 Aspergillus spp. SWI5 sequences and 1 SWI5 sequence for Neosartorya fischeri. PCR primers were designed and applied to generate sequence information for the SWI5 gene in Aspergillus spp. SWI5 is present in some Candida spp. e.g. C. glabrata but not others e.g. C. albicans (MacCallum et al., 2006). Therefore, the potential exists to use SWI5 for the molecular identification of selected Candida spp.

DEFINITIONS

"Synthetic oligonucleotide" refers to molecules of nucleic acid polymers of 2 or more nucleotide bases that are not derived directly from genomic DNA or live organisms. The term synthetic oligonucleotide is intended to encompass DNA, RNA, and DNA/RNA hybrid molecules that have been manufactured chemically, or synthesized enzymatically in vitro.

An "oligonucleotide" is a nucleotide polymer having two or more nucleotide subunits covalently joined together. Oligonucleotides are generally about 10 to about 100 nucleotides. The sugar groups of the nucleotide subunits may be ribose, deoxyribose, or modified derivatives thereof such as OMe. The nucleotide subunits may be joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention. A "target nucleic acid" is a nucleic acid comprising a target nucleic acid sequence. A "target nucleic acid sequence," "target nucleotide sequence" or "target sequence" is a specific deoxyribonucleotide or ribonucleotide sequence that can be hybridized to a complementary oligonucleotide.

An "oligonucleotide probe" is an oligonucleotide having a nucleotide sequence sufficiently complementary to its target nucleic acid sequence to be able to form a detectable hybrid probe:target duplex under high stringency hybridization conditions. An oligonucleotide probe is an isolated chemical species and may include additional nucleotides outside of the targeted region as long as such nucleotides do not prevent hybridization under high stringency hybridization conditions. Non-complementary sequences, such as promoter sequences, restriction endonuclease recognition sites, or sequences that confer a desired secondary or tertiary structure such as a catalytic active site can be used to facilitate detection using the invented probes. An oligonucleotide probe optionally may be labelled with a detectable moiety such as a radioisotope, a fluorescent moiety, a chemiluminescent, a nanoparticle moiety, an enzyme or a ligand, which can be used to detect or confirm probe hybridization to its target sequence. Oligonucleotide probes are preferred to be in the size range of from about 10 to about 100 nucleotides in length, although it is possible for probes to be as much as and above about 500 nucleotides in length, or below 10 nucleotides in length.

A "hybrid" or a "duplex" is a complex formed between two single-stranded nucleic acid sequences by Watson-Crick base pairings or non-canonical base pairings between the complementary bases. "Hybridization" is the process by which two complementary strands of nucleic acid combine to form a double-stranded structure ("hybrid" or "duplex"). A "fungus" or "yeast" is meant any organism of the kingdom Fungi, and preferably, is directed towards any organism of the phylum Ascomycota.

"Complementarity" is a property conferred by the base sequence of a single strand of DNA or RNA which may form a hybrid or double-stranded DNA:DNA, RNA:RNA or DNA:RNA through hydrogen bonding between Watson-Crick base pairs on the respective strands. Adenine (A) ordinarily complements thymine (T) or uracil (U), while guanine (G) ordinarily complements cytosine (C).

The term "stringency" is used to describe the temperature, ionic strength and solvent composition existing during hybridization and the subsequent processing steps. Those skilled in the art will recognize that "stringency" conditions may be altered by varying those parameters either individually or together. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid. With "high stringency" conditions, nucleic acid base pairing will occur only between nucleic acid fragments that have a high frequency of complementary base sequences (for example, hybridization under "high stringency" conditions, may occur between homologs with about 85-100% identity, preferably about 70-100% identity). With medium stringency conditions, nucleic acid base pairing will occur between nucleic acids with an intermediate frequency of complementary base sequences (for example, hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

'High stringency' conditions are those equivalent to binding or hybridization at 42° C. in a solution consisting of 5×SSPE (43.8 g/l NaCl, 6.9 g/l $NaH_2PO_4H_2O$ and 1.85 g/l EDTA, ph adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is used.

"Medium stringency' conditions are those equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0× SSPE, 1.0% SDS at 42° C., when a probe of about 500 nucleotides in length is used. 'Low stringency' conditions are those equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml:5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C., when a probe of about 500 nucleotides in length is used.

In the context of nucleic acid in-vitro amplification based technologies, "stringency" is achieved by applying temperature conditions and ionic buffer conditions that are particular to that in-vitro amplification technology. For example, in the context of PCR and real-time PCR, "stringency" is achieved by applying specific temperatures and ionic buffer strength for hybridisation of the oligonucleotide primers and, with regards to real-time PCR hybridisation of the probe/s, to the target nucleic acid for in-vitro amplification of the target nucleic acid.

One skilled in the art will understand that substantially corresponding probes of the invention can vary from the referred-to sequence and still hybridize to the same target nucleic acid sequence. This variation from the nucleic acid may be stated in terms of a percentage of identical bases within the sequence or the percentage of perfectly complementary bases between the probe and its target sequence. Probes of the present invention substantially correspond to a nucleic acid sequence if these percentages are from about 100% to about 80% or from 0 base mismatches in about 10 nucleotide target sequence to about 2 bases mismatched in an about 10 nucleotide target sequence. In preferred embodiments, the percentage is from about 100% to about 85%. In more preferred embodiments, this percentage is from about 90% to about 100%; in other preferred embodiments, this percentage is from about 95% to about 100%

By "sufficiently complementary" or "substantially complementary" is meant nucleic acids having a sufficient amount of contiguous complementary nucleotides to form, under high stringency hybridization conditions, a hybrid that is stable for detection. The terms "identical" or percent "identity," in the context of two or more nucleic acids or polypeptide sequences, refer to two or more sequences or subsequences that are the same or have a specified percentage of amino acid residues or nucleotides that are the same (i.e., 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)). A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

By "nucleic acid hybrid" or "probe:target duplex" is meant a structure that is a double-stranded, hydrogen-bonded structure, preferably about 10 to about 100 nucleotides in length, more preferably 14 to 50 nucleotides in length, although this will depend to an extent on the overall length of the oligonucleotide probe. The structure is sufficiently stable to be detected by means such as chemiluminescent or fluorescent light detection, autoradiography, electrochemical analysis or gel electrophoresis. Such hybrids include RNA:RNA, RNA:DNA, or DNA:DNA duplex molecules.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

By "preferentially hybridize" is meant that under high stringency hybridization conditions oligonucleotide probes can hybridize their target nucleic acids to form stable probe:target hybrids (thereby indicating the presence of the target nucleic acids) without forming stable probe:non-target hybrids (that would indicate the presence of non-target nucleic acids from other organisms). Thus, the probe hybridizes to target nucleic acid to a sufficiently greater extent than to non-target nucleic acid to enable one skilled in the art to accurately detect the presence of (for example *Candida*) and distinguish these species from other organisms. Preferential hybridization can be measured using techniques known in the art and described herein.

By "theranostics" is meant the use of diagnostic testing to diagnose the disease, choose the correct treatment regime and monitor the patient response to therapy. The theranostics of the invention may be based on the use of an NAD assay of this invention on samples, swabs or specimens collected from the patient.

OBJECT OF THE INVENTION

It is an object of the current invention to provide sequences and/or diagnostic assays to detect and identify one or more fungal and yeast species. The current inventors have used the SWI5 gene sequence to design primers and probes that are specific to *Aspergillus* SWI5 genes. Such primers may allow the detection of yeast and fungal species and also allow distinction between *Candida* and *Aspergillus* species, foe example. The current invention further provides for primers and probes that may allow discrimination between different *Candida* spp. and among different *Aspergillus* spp.

SUMMARY OF THE INVENTION

The present invention provides for a diagnostic kit for detection and identification of fungal rand yeast species, comprising an oligonucleotide probe capable of binding to at least a portion of the SWI5 gene or its corresponding mRNA. The oligonucleotide probe may have a sequence substantially homologous to or substantially complementary to at least a portion of the SWI5 gene or its corresponding mRNA. It will thus be capable of binding or hybridizing with a complementary DNA or RNA molecule. The SWI5 gene may be a fungal SWI5 gene. The SWI5 gene may be yeast SWI5 gene. The nucleic acid molecule may be synthetic. The kit may comprise more than one such probe. In particular, the kit may comprise a plurality of such probes. In addition the kit may comprise additional probes for other organisms, such as, for example, bacterial species or viruses.

The identified sequences are suitable not only for in vitro DNA/RNA amplification based detection systems but also for signal amplification based detection systems. Furthermore, the sequences of the invention identified as suitable targets provide the advantages of having significant intragenic sequence heterogeneity in some regions, which is advantageous and enables aspects of the invention to be directed towards group or species-specific targets, and also having significant sequence homogeneity in some regions, which enables aspects of the invention to be directed towards genus-specific fungal and yeast primers and probes for use in direct nucleic acid detection technologies, signal amplification nucleic acid detection technologies, and nucleic acid in vitro amplification technologies for fungal and yeast diagnostics. The SWI5 sequences allow for multi-test capability and automation in diagnostic assays.

One of the advantages of the sequences of the present invention is that the intragenic SWI5 nucleotide sequence diversity between closely related fungi and yeast enables specific primers and probes for use in diagnostics assays for the detection of fungi and yeast to be designed. The SWI5 nucleotide sequences, both DNA and RNA can be used with direct detection, signal amplification detection and in vitro amplification technologies in diagnostics assays. The SWI5 sequences allow for multi-test capability and automation in diagnostic assays.

The kit may further comprise a primer for amplification of at least a portion of the SWI5 gene. Suitably, the kit comprises a forward and a reverse primer for a portion of the SWI5 gene.

The portion of the SWI5 gene may be equivalent to a region of SWI5 equivalent to by positions 1-2319.

Equivalent positions to base pair position 1 to base pair position 2319 in *A. fumigatus* can be found in other organisms, but not necessarily in the same position.

The portion of the SWI5 gene may be equivalent to two regions of the SWI5 gene in *Aspergillus* spp. equivalent to base pair position 38 to base pair position 472 in *A. fumigatus* (region 1) and from base pair position 1423 to 1627 base pair position in *A. fumigatus* (region 3).

Equivalent positions to base pair position 38 to base pair position 472 and from base pair position 1423 to 1627 in *A. fumigatus* can be found in other organisms, but not necessarily in the same position.

The kit may also comprise additional probes.

The probe may have a sequence selected from the group SEQ ID NO 17, 18, 42, 45, 48, 51, 54, 61, 64, or 67 or a sequence substantially homologous to or substantially complementary to those sequences which can also act as a probe for the SWI5 gene.

The kit may comprise at least one forward in vitro amplification primer and at least one reverse in vitro amplification primer. Such primers may include a forward primer which preferentially hybridizes to the same nucleotide sequence as is preferentially hybridized by SEQ ID NOs: 1, 3, 5, 7, 9, 11, 13, 15, 36, 38, 40, 43, 46, 49, 52, 55, 58, 59, 62 or 65 and/or a reverse primer which preferentially hybridizes to the same nucleotide sequence as is preferentially hybridized by SEQ ID NOs: 2, 4, 6, 8, 10, 12, 14, 16, 37, 39, 41, 44, 47, 50, 53, 56, 57, 60, 63 or 66, or a sequence being substantially homologous or complementary thereto which can also act as a forward or reverse amplification primer. The diagnostic kit may be based on direct nucleic acid detection technologies, signal amplification nucleic acid detection technologies, and nucleic acid in vitro amplification technologies is selected from one or more of Polymerase Chain Reaction (PCR), Ligase Chain Reaction (LCR), Nucleic Acids Sequence Based Amplification (NASBA), Strand Displacement Amplification (SDA), Transcription Mediated Amplification (TMA), Branched DNA technology (bDNA) and Rolling Circle Amplification Technology (RCAT)), or other in vitro enzymatic amplification technologies.

The invention also provides a nucleic acid molecule selected from the group consisting of SEQ ID NO.1 to SEQ ID NO. 95 and sequences substantially homologous thereto, or substantially complementary to a portion thereof and having a function in diagnostics based on the SWI5 gene. The nucleic acid molecule may comprise an oligonucleotide having a sequence substantially homologous to or substantially complementary to a portion of a nucleic acid molecule of SEQ ID NO.1 to SEQ ID NO. 95. The invention also provides a method of detecting a target organism in a test sample comprising the steps of:
(i) Mixing the test sample with at least one oligonucleotide probe as defined above under appropriate conditions; and
(ii) hybridizing under high stringency conditions any nucleic acid that may be present in the test sample with the oligonucleotide to form a probe:target duplex; and
(iii) determining whether a probe:target duplex is present; the presence of the duplex positively identifying the presence of the target organism in the test sample.

The nucleic acid molecule and kits of the present invention may be used in a diagnostic assay to detect the presence of one or more fungal and/or yeast species, to measure fungal and/or yeast titres in a patient or in a method of assessing the efficacy of a treatment regime designed to reduce yeast and/or fungal titre in a patient or to measure fungal and/or yeast contamination in an environment. The environment may be a hospital, or it may be a food sample, an environmental sample e.g. water, an industrial sample such as an in-process sample or an end product requiring bioburden or quality assessment.

The kits and the nucleic acid molecule of the invention may be used in the identification and/or characterization of one or more disruptive agents that can be used to disrupt the SWI5 gene function. The disruptive agent may be selected from the group consisting of antisense RNA, PNA, and siRNA.

In some embodiments of the invention, a nucleic acid molecule comprising a species-specific probe can be used to discriminate between species of the same genus.

The oligonucleotides of the invention may be provided in a composition for detecting the nucleic acids of fungal and yeast target organisms. Such a composition may also comprise buffers, enzymes, detergents, salts and so on, as appropriate to the intended use of the compositions. It is also envisioned that the compositions, kits and methods of the invention, while described herein as comprising at least one synthetic oligonucleotide, may also comprise natural oligonucleotides with substantially the same sequences as the synthetic nucleotide fragments in place of, or alongside synthetic oligonucleotides.

The invention also provides for an in vitro amplification diagnostic kit for a target fungal and/or yeast organism comprising at least one forward in vitro amplification primer and at least one reverse in vitro amplification primer, the forward amplification primer being selected from the group consisting of one or more of or a sequence being substantially homologous or complementary thereto which can also act as a forward amplification primer, and the reverse amplification primer being selected from the group consisting of one or more of or a sequence being substantially homologous or complementary thereto which can also act as a reverse amplification primer.

The invention also provides for a diagnostic kit for detecting the presence of candidate fungal and/or yeast species, comprising one or more DNA probes comprising a sequence substantially complementary to, or substantially homologous to the sequence of the SWI5 gene of the candidate fungal and/or species.

A kit useful for detecting an *Aspergillus* or *Candida glabrata* SWI5 polynucleotide comprises an oligonucleotide probe selected from SEQ ID NOs: 17, 18, 42, 45, 48, 51, 54, 61, 64, or 67 or a probe which preferentially hybridizes to the same nucleotide sequence as is preferentially hybridized by SEQ ID NOs: 17, 18, 42, 45, 48, 51, 54, 61, 64, or 67. The kit may further comprise a forward primer selected from SEQ ID NOs: 1, 3, 5, 7, 9, 11, 13, 15, 36, 38, 40, 43, 46, 49, 52, 55, 58, 59, 62 or 65 or a probe which preferentially hybridizes to the same nucleotide sequence as is preferentially hybridized by SEQ ID NOs: 1, 3, 5, 7, 9, 11, 13, 15, 36, 38, 40, 43, 46, 49, 52, 55, 58, 59, 62 or 65 and/or a reverse primer selected from SEQ ID NOs: 2, 4, 6, 8, 10, 12, 14, 16, 37, 39, 41, 44, 47, 50, 53, 56, 57, 60, 63 or 66 or a probe which preferentially hybridizes to the same nucleotide sequence as is preferentially hybridized by SEQ ID NOs: 2, 4, 6, 8, 10, 12, 14, 16, 37, 39, 41, 44, 47, 50, 53, 56, 57, 60, 63 or 66.

A kit for detecting or identifying a *Aspergillus fumigatus* SWI5 polynucleotide comprises an oligonucleotide probe selected from SEQ ID NO: 17 or 18 or 42 and 54 or a sequence which preferentially hybridizes to the same nucleotide sequence as is preferentially hybridized by SEQ ID NO: 17 or 18 or 42 and 54 and further comprises a forward primer selected from SEQ ID NO: 43, 55, 58 or a sequence which preferentially hybridizes to the same nucleotide sequence as is preferentially hybridized by SEQ ID NO: 43, 55, 58 and a reverse primer which is selected from SEQ ID NO: 44, 56, 57 or a sequence which preferentially hybridizes the same nucleotide sequence as is preferentially hybridized by SEQ ID NO: 44, 56, 57.

A kit for detecting or identifying a *Aspergillus flavus* SWI5 polynucleotide comprises an oligonucleotide probe selected from SEQ ID NO: 45, 61 and sequences which preferentially hybridizes to the same nucleotide sequence as is preferentially hybridized by SEQ ID NO: 45, 61 and further comprises a forward primer selected from SEQ ID NO: 46, 59 and sequences which preferentially hybridizes to the same nucleotide sequence as is preferentially hybridized by SEQ ID NO: 46, 59 and a reverse primer selected from SEQ ID NO: 47, 60 and sequences which preferentially hybridizes to the same nucleotide sequence as is preferentially hybridized by SEQ ID NO: 47, 60.

A kit for detecting or identifying a *Aspergillus niger* SWI5 polynucleotide comprises an oligonucleotide probe selected from SEQ ID NO: 48, 67 and sequences which preferentially hybridizes to the same nucleotide sequence as is preferentially hybridized by SEQ ID NO: 48, 67 and further comprises a forward primer selected from SEQ ID NO: 48, 65 and sequences which preferentially hybridizes to the same nucleotide sequence as is preferentially hybridized by SEQ ID NO: 48, 65 and a reverse primer selected from SEQ ID NO: 49, 66 and sequences which preferentially hybridizes to the same nucleotide sequence as is preferentially hybridized by SEQ ID NO: 49, 66.

A kit for detecting or identifying a *Aspergillus terreus* SWI5 polynucleotide comprises an oligonucleotide probe selected from SEQ ID NO: 51, 64 and sequences which preferentially hybridizes to the same nucleotide sequence as is preferentially hybridized by SEQ ID NO: 51, 64 and further comprises a forward primer selected from SEQ ID NO: 52, 62 and sequences which preferentially hybridizes to the same nucleotide sequence as is preferentially hybridized by SEQ ID NO: 52, 62 and a reverse primer selected from SEQ ID NO: 53, 63 and sequences which preferentially hybridizes to the same nucleotide sequence as is preferentially hybridized by SEQ ID NO: 53, 63.

The present invention also provides for one or more synthetic oligonucleotides having a nucleotide sequence substantially homologous to or substantially complementary to one or more of the group consisting of the SWI5 gene or mRNA transcript thereof, the fungal SWI5 gene or mRNA transcript thereof, the yeast SWI5 gene or mRNA transcript thereof, one or more of SEQ ID NO 1-SEQ ID NO 95.

The nucleotide may comprise DNA. The nucleotide may comprise RNA. The nucleotide may comprise a mixture of DNA, RNA and PNA. The nucleotide may comprise synthetic nucleotides. The sequences of the invention (and the sequences relating to the methods, kits compositions and assays of the invention) may be selected to be substantially homologous to a portion of the coding region of the SWI5 gene. The gene may be a gene from a target fungal and/or yeast organism. The sequences of the invention are preferably sufficient so as to be able to form a probe:target duplex to the portion of the sequence.

The invention also provides for a diagnostic kit for a target fungal or yeast organism comprising an oligonucleotide probe substantially homologous to or substantially complementary to an oligonucleotide of the invention (which may be synthetic). It will be appreciated that sequences suitable for use as in vitro amplification primers may also be suitable for use as oligonucleotide probes: while it is preferable that amplification primers may have a complementary portion of between about 15 nucleotides and about 30 nucleotides (more preferably about 15-about 23, most preferably about 20 to about 23), oligonucleotide probes of the invention may be any suitable length. The skilled person will appreciate that different hybridization and or annealing conditions will be required depending on the length, nature & structure (eg. Hybridization probe pairs for LightCycler, Taqman 5' exonuclease probes, hairpin loop structures etc. and sequence of the oligonucleotide probe selected.

Kits and assays of the invention may also be provided wherein the oligonucleotide probe is immobilized on a surface. Such a surface may be a bead, a membrane, a column, dipstick, a nanoparticle, the interior surface of a reaction chamber such as the well of a diagnostic plate or inside of a reaction tube, capillary or vessel or the like. The target fungal organism may be selected from the group consisting of *A. fumigatus, N. fischeri, A. clavatus, A. niger, A. terreus, A. flavus, A. versicolor* and *A. nidulans*. The target yeast organisms may be the *Candida* species *C. glabrata*.

Under these circumstances, the amplification primers and oligonucleotide probes of the invention may be designed to a gene specific or genus specific region so as to be able to identify one or more, or most, or substantially all of the desired organisms of the target yeast organism grouping.

The target fungal organisms may be an *Aspergillus* species for given set of primers already experimentally demonstrated, and more preferably, selected from the group consisting of *A. fumigatus, A. clavatus, A. niger, A. terreus, A. flavus, A. versicolor* and *A. nidulans*.

The test sample may comprise cells of the target fungal and/or yeast organism. The method may also comprise a step for releasing nucleic acid from any cells of the target fungal or yeast organism that may be present in said test sample. Ideally, the test sample is a lysate of an obtained sample from a patient (such as a swab, or blood, urine, saliva, a bronchial lavage, dental specimen, skin specimen, scalp specimen, transplant organ biopsy, stool, mucus, or discharge sample). The test samples may be a food sample, a water sample, an environmental sample, an end product, end product or in-process industrial sample.

The invention also provides for the use of any one of SEQ ID NO.1 to SEQ ID NO. 35 in a diagnostic assay for the presence of one or more yeast or fungal species. The species may be selected from the group consisting of *C. glabrata, A. fumigatus, N. fischeri, A. clavatus, A. niger, A. terreus, A. flavus, A. versicolor* and *A. nidulans*. The invention also provides for kits for use in clinical diagnostics, theranostics, food safety diagnostics, industrial microbiology diagnostics, environmental monitoring, veterinary diagnostics, bio-terrorism diagnostics comprising one or more of the synthetic oligonucleotides of the invention. The kits may also comprise one or more articles selected from the group consisting of appropriate sample collecting instruments, reagent containers, buffers, labelling moieties, solutions, detergents and supplementary solutions. The invention also provides for use of the sequences, compositions, nucleotide fragments, assays, and kits of the invention in theranostics, Food safety diagnostics, Industrial microbiology diagnostics, Environmental monitoring, Veterinary diagnostics, Bio-terrorism diagnostics.

The nucleic acid molecules, composition, kits or methods may be used in a diagnostic nucleic acid based assay for the detection of fungal and/or yeast species.

The nucleic acid molecules, composition, kits or methods may be used in a diagnostic assay to measure fungal and/or yeast titres in a patient. The titres may be measured in vitro.

The nucleic acid molecules, composition, kits or methods may be used in a method of assessing the efficacy of a treatment regime designed to reduce fungal and/or yeast titre in a patient comprising assessing the fungal and/or yeast titre in the patient (by in vivo methods or in vitro methods) at one or more key stages of the treatment regime. Suitable key stages may include before treatment, during treatment and after treatment. The treatment regime may comprise an antifungal agent, such as a pharmaceutical drug. The nucleic acid molecules, composition, kits or methods may be used in a diagnostic assay to measure potential fungal and/or yeast contamination, for example, in a hospital. The nucleic acid molecules, composition, kits or methods may be used in the identification and/or characterization of one or more disruptive agents that can be used to disrupt the SWI5 gene function. Suitable disruptive agents may be selected from the group consisting of antisense RNA, PNA, siRNA.

BRIEF DESCRIPTION OF THE FIGURES

FIG. 1: Selected primer binding sites in the SWI5 gene of *Aspergillus fumigatus* SEQ ID NO 29. The regions (1, 2 and 3) of interest are underlined (Position of Region 1: 38 to 472. Position of Region 2: 1034-1241. Position of Region 3: 1423-1627).

FIG. 2: Binding site of *A. fumigatus* probe P1-AspSWI5-1, SEQ ID NOs 17 (underlined and bolded) in the amplified fragment of SWI5 (Region 1 of interest). PCR primes AspSWI5-1-F (SEQ ID NO. 1)/AspSWI5-1-R (SEQ ID NO. 2) are highlighted.

FIG. 3: Binding site of *A. fumigatus* probe P1-AspSWI5-3, SEQ ID NO. 18. (underlined and bolded) in the amplified fragment of SWI5 (Region 3 of interest). PCR primers AspSWI5-3-F (SEQ ID NO. 5)/AspSWI5-3-R (SEQ ID NO. 6) are highlighted.

The results show the LOD for the *A. terreus* Aterr_SWI5_1 assay.

The thermocycling conditions included annealing at 95° C. for 5 seconds and 60° C. for 10 seconds for 50 cycles. An LOD of $10^5$ cell equivalents per reaction was obtained.

Figure 9:
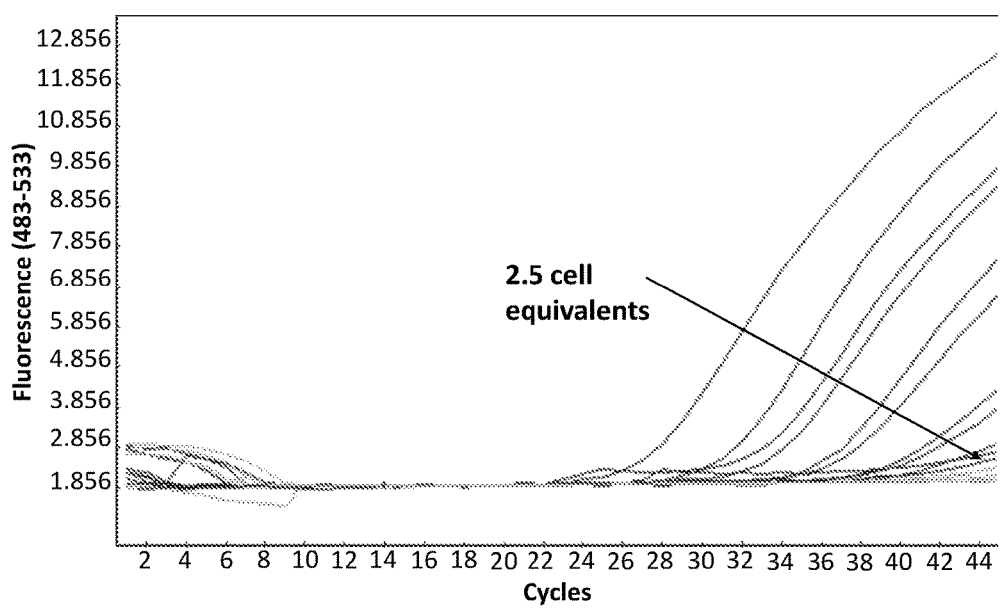
Figure 9:
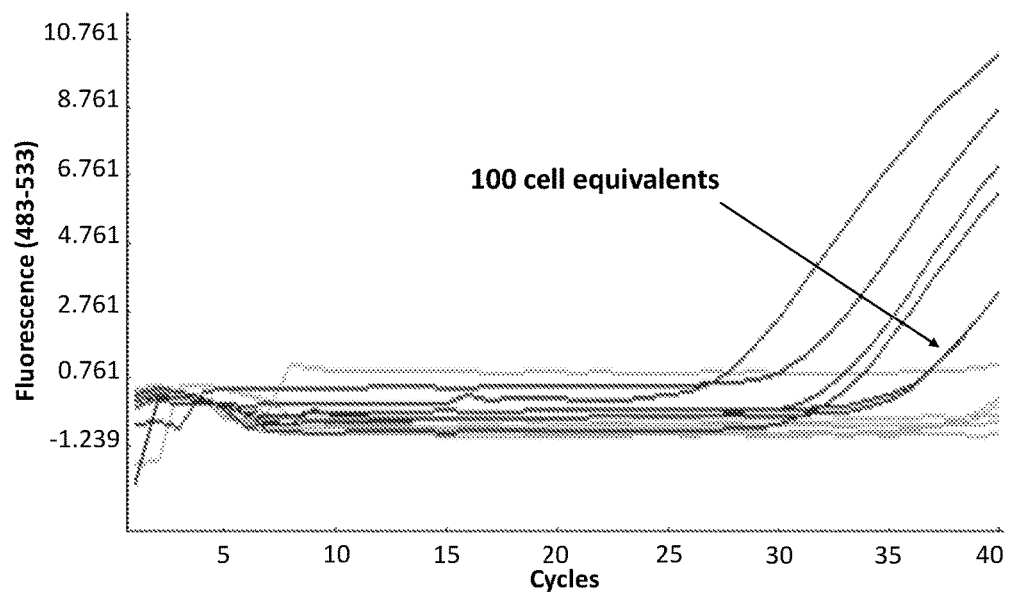

FIG. 9: Limit of detection of *A. fumigatus* Afum_SWI5_2:

Graphs show the results obtained for the LOD assays preformed on *A. fumigatus* Afum_SWI5_2 assay. Results shown in graph a were obtained following denaturation and annealing annealing for 95° C. for 10 secs and 60° C. for 30 secs for 50 cycles respectively. The results shown in graph b were obtained following denaturation and annealing at 95° C. for 5 secs and 60° C. for 20 secs, for 40 cycles. The LOD obtained was 100 cell equivalent.

Figure 10:
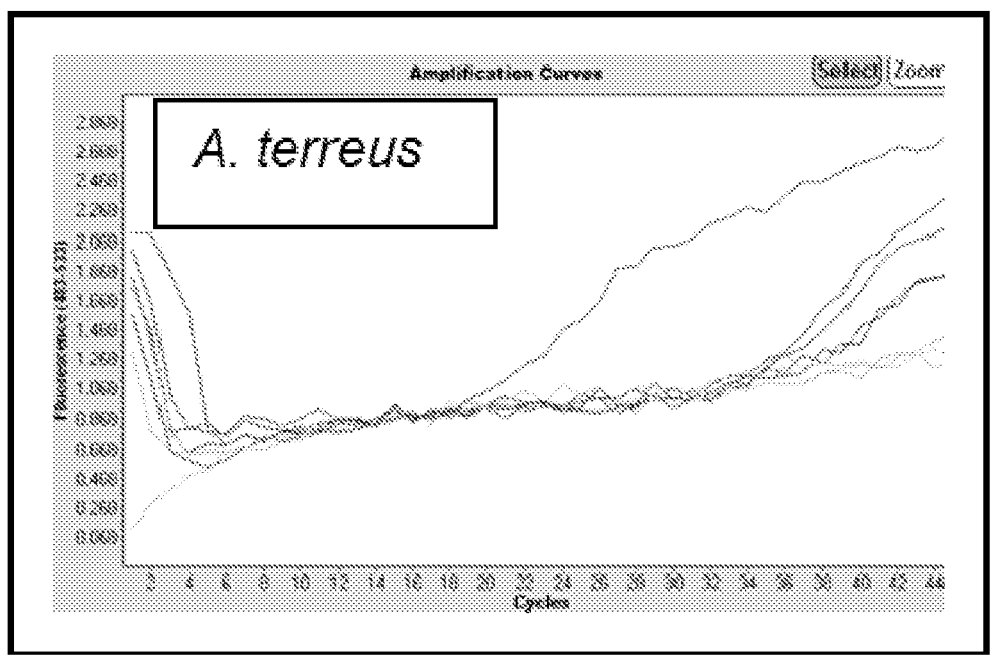
Figure 10:
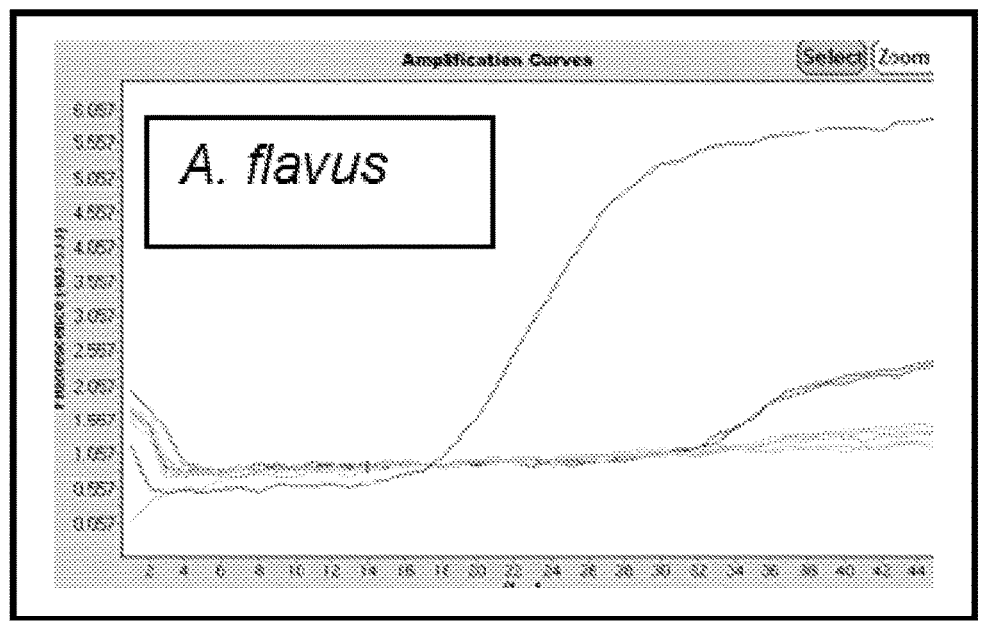
Figure 10:
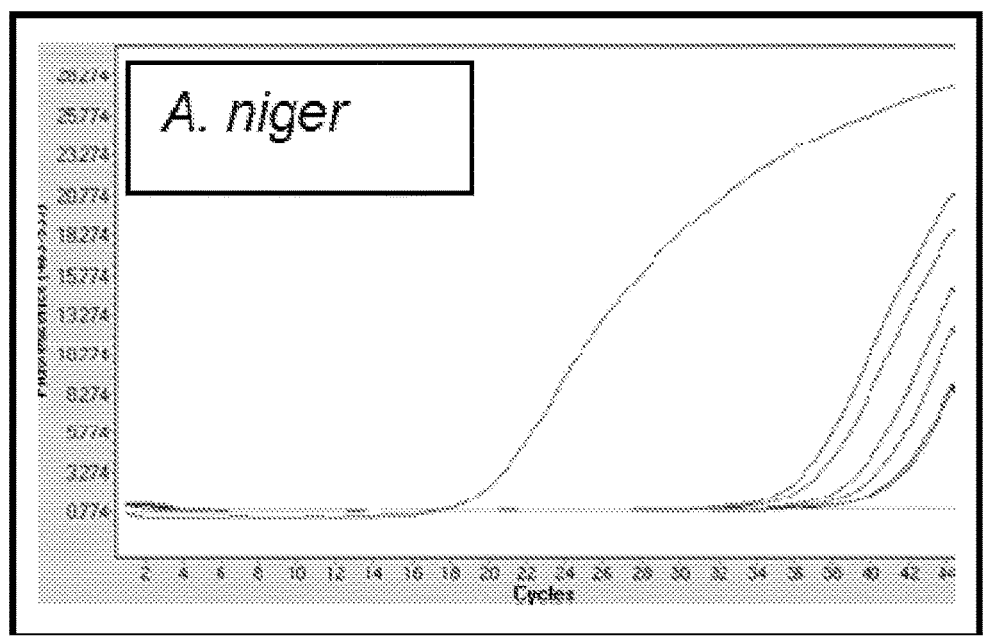

FIG. 10: Limit of detection for the SWI5_2 assays for *A. flavus*, *A. niger* and *A. terreus*.

Annealing was 95° C. for 5 secs and 60° C. for 10 secs, for 45 cycles. *A. niger* assay shown in graph c was the only successful assay with a LOD of 10 cell equivalents.

Figure 11:
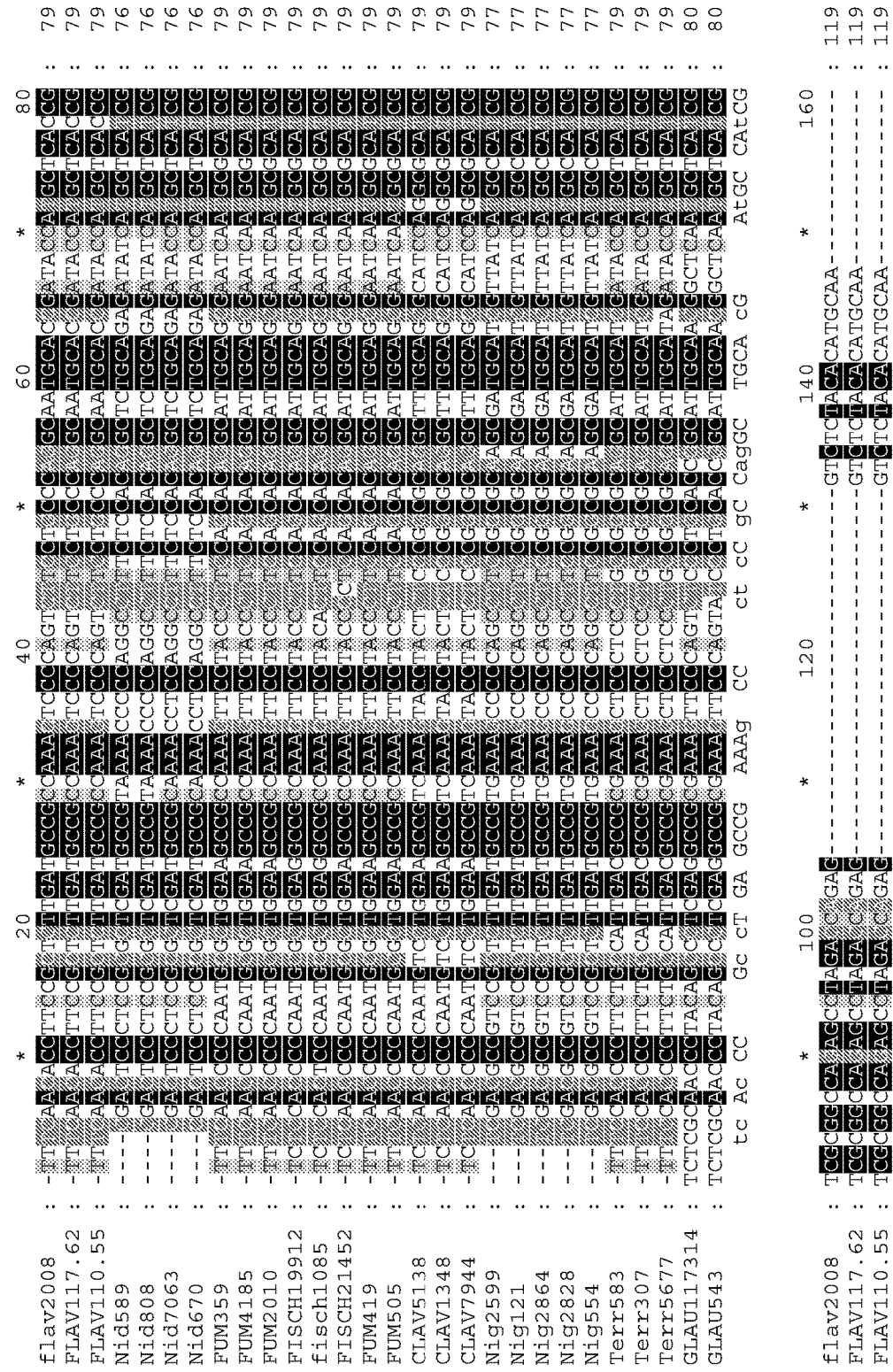

FIG. 11 Master alignment of SWI5 sequence information.

DETAILED DESCRIPTION OF THE INVENTION

Example 1

Materials and Methods

Cell Culture

*Aspergillus* species were cultured in Sabouraud broth (4% wt/vol glucose, 1% wt/vol peptone, 1.5% agar) or agar for 3-4 days at 25° C.

DNA Extraction

*Aspergillus* spp. were pre-treated with lyticase or zymolase enzymes prior to DNA isolation. DNA was isolated from *Apergillus* spp. using the MagNA Pure System (Roche Molecular Systems) in combination with the MagNA pure Yeast and Bacterial isolation kit III according to the manufacturers protocol.

DNA Sequencing of SWI5 Gene Regions in *Aspergillus* spp.

The publicly available sequences of the SWI5 genes for *Aspergillus* species were acquired from the NCBI GenBank database and aligned using Clustal W. Combinations of PCR primers were used to amplify sub-regions of SWI5 in *Aspergillus* species equivalent by 1 to by 2319 of *Aspergillus fumigatus*. For example, PCR Primers AspSWI5-1-F/Asp SWI5-1-R were designed to amplify a region in *Aspergillus* spp. equivalent to by position 38 to 472 in *A. fumigatus* XM_749401.1 (Region 1, FIG. 1). PCR primers AspSWI5-2-F/AspSWI5-2-R were designed to amplify a region in *Aspergillus* spp. equivalent to by position 1034 to 1241 in *A. fumigatus* (Region 2, FIG. 1). AspSWI5-3-F/AspSWI5-3-R were designed to amplify a region in *Aspergillus* spp. equivalent to by position 1423 to 1627 in *A. fumigatus* XM_749401.1 (Region 3, FIG. 1). The SWI5 gene regions were amplified in a range of *Aspergillus* spp. iCycler BioRad PCR machine or the PTC200 Peltier thermocycler (MJ Research) using the reagents outlined in Table 2 and the thermocycling conditions described in Table 3 or modifications thereof. The PCR reaction products were purified with Roche High Pure PCR Product Purification kit or with the ExoSAP-IT kit (USB) according to the manufacturers' instructions sent for sequencing to Sequiserve, Germany and sequenced using the forward amplification primer AspSWI5-1-F or AspSWI5-3-F. DNA sequence information was generated as follows: *Aspergillus* region 1 sequence information was generated for 5 *Aspergillus* species (*A. fumigatus*, *A. nidulans*, *A. clavatus*, *A. niger*, *A. flavus*) and *Neosartorya fischeri*. *Aspergillus* region 3 sequence information was generated for 3 *Aspergillus* species (*A. fumigatus*, *A. nidulans*, *A. niger*) and *Neosartorya fischeri*.

TABLE 1

PCR primers designed to amplify SWI5 gene regions in *Aspergillus* spp.

| | Primer Name | Primer Sequence |
|---|---|---|
| SEQ ID NO. 1 | AspSWI5-1-F | ATCGACAACATCGTCGGCAGA |
| SEQ ID NO. 2 | AspSWI5-1-R | GCTGTTGCTGTTGCATCAGATT |
| SEQ ID NO. 3 | AspSWI5-2-F | TAGCCGCCATGCCAAGC |
| SEQ ID NO. 4 | AspSWI5-2-R | CCAGTCTCTTTGATAGAAGCA |
| SEQ ID NO. 5 | AspSWI5-3-F | CGTGGACATGACCTG AAGC |
| SEQ ID NO. 6 | AspSWI5-3-R | GTCTCTCCTCCAACTCTGG |
| SEQ ID NO. 7 | 1F | ATGTTAGCCAATCCAC |
| SEQ ID NO. 8 | 1R | ATTCCAGGCACCG |
| SEQ ID NO. 9 | 2F | CTTGAGGGCCAAATC |
| SEQ ID NO. 10 | 2R | CTCGTCCTTTCAATCC |
| SEQ ID NO. 11 | 3F | ACTATGCCTCGTCG |
| SEQ ID NO. 12 | 3R | AGCGAATACATTGCC |
| SEQ ID NO. 13 | 4F | ACAAACCATATGAATGTC |
| SEQ ID NO. 14 | 4R | GCAGGCTCGGTT |
| SEQ ID NO. 15 | 5F | CCTCGAGAAGATCGT |
| SEQ ID NO. 16 | 5R | CTAGCAGTCCATGAAG |

TABLE 2

PCR reagents used to amplify the SWI5 gene regions in *Aspergillus* spp

| PCR Reaction Mix | SAMPLE x 1 |
|---|---|
| 10 x Buffer (100 mM Tris HCl, 15 mM MgCl$_2$, 500 mM KCl pH 8.3) | 5 µl |
| dNTP's Mix, Roche (10 mM dNTP) | 1 µl |
| Primer Forward primer (10 µM) | 1 µl |
| Primer Reverse primer (10 µM) | 1 µl |
| Polymerase TaqPol, Roche 1 U/µl | 1 µl |
| H$_2$O Amgen/Accugene | 36-39 µl |
| Genomic DNA Template | 2-5 µl |
| TOTAL VOLUME | 50 µl |

TABLE 3

PCR reaction conditions applied to amplify the SWI5 gene regions in *Aspergillus* spp.
PCR Thermal profile   Lid preheating was ON

| Step | Temp | Time | |
|---|---|---|---|
| 1 | 94° C. | 1 min | X 35 |
| 2 | 50° C.-59° C. | 1 min | |
| 3 | 72° C. | 1 min | |
| 4 | 72° C. | 7 min | |
| 5 | 8° C. | Hold | |

TABLE 5

Real-time PCR reagents

| Preparation of PCR Reaction Mix LightCycler ® FastStartDNA Master HybProbe, Roche Cat. 03 003 248 00 | SAMPLE x 1 |
|---|---|
| HybProb mix 10 x conc. (Red cap) | 2 µl |
| MgCl$_2$ stock solution (Blue cap) (Final conc. in reaction is 3 mM) | 1.6 µl |
| Probe P1-AspSWI5 or P1-AspSWI5-3 | 2 µl |
| Primer Forward AspSWI5-1-F or AspSWI5-3-F | 1 µl |
| Primer Reverse AspSWI5-1-R or AspSWI5-3-R | 1 µl |
| H$_2$O PCR-grade | 10.4 µl |
| Template | 2 µl |
| TOTAL VOLUME | 20 µl |

TABLE 4

TaqMan probes (5'-FAM and 3'-BHQ1 labels) based on the SWI5 gene regions in *A. fumigatus*.

| | Probe Name | Probe Sequence |
|---|---|---|
| SEQ ID NO. 17 | P1-AspSWI5-1 | CCAAAGTTCCTACCCTTCCAGCAC |
| SEQ ID NO. 18 | P1-AspSWI5-3 | CTGACTCGGCACAGACAACGAGGA |

TABLE 6

Real-time PCR thermocycling conditions
PCR Thermal profile

| Cycle | Step | Temp | Time | |
|---|---|---|---|---|
| Activation | 1 | 95° C. | 10 min | X 50 |
| Amplification | 1 | 95° C. | 10 sec | |
| | 2 | 62-65° C. | 20 sec | |
| | 3 | 70° C. | 10 sec | |
| Cooling | 1 | 40° C. | Hold | |

Results

Primer and Probe Design

The publicly available sequence information available for the SWI5 gene in *Aspergillus* spp. was aligned with the newly generated sequence information for the SWI5 gene in *Aspergillus* spp. and analysed using bioinformatics tools. Species-specific probes were designed based on the compiled SWI5 sequence information for *Aspergillus fumigatus* (regions 1 and 3) (Table 4). FIGS. 2 and 3 show the relative positions of the PCR primers and TaqMan DNA probes for the amplification and detection of *A. fumigatus*.

Real-Time PCR

The specificity of the TaqMan probes for the identification of *A. fumigatus* was demonstrated in real-time PCR assays on the LightCycler using the reagents and thermocycling conditions outlined in Tables 5 and 6. For the *A. fumigatus* assay based on the SWI5 gene region 1, PCR primers AspSWI5-1-F/AspSWI5-1-R were combined in with TaqMan probe, P1-AspSWI5-1. For the *A. fumigatus* assay based on the SWI5 gene region 3, PCR primers AspSWI5-3-F/AspSWI5-3-R were combined with TaqMan probe, P1-AspSWI5-3.

The specificity of the assays for the detection of *A. fumigatus* was confirmed by including DNA from a range of closely related *Aspergillus* species and *C. albicans* in the *A. fumigatus* real-time PCR assays. The assays detected *A. fumigatus* but did not detect or cross-react with DNA from *C. albicans* or any other *Aspergillus* species tested. FIGS.

4-5 show the *A. fumigatus* real-time PCR assays based on SWI5 regions 1 and 3 and the specificity of the assays for *A. fumigatus*.

Example 2

Additional primers to amplify *A. nidulans, A. niger* and *A. terreus* were designed. These primers produced PCR products from these species which were sequenced. The primer sequences are outlined in Table 7. AnigSWI5 primer set were designed to amplify positions 43 to 512 to produce a PCR product of 469 bp in length, AterrSWI5 primer set amplified positions 44 to 450 producing a PCR product of 469 bp and AnidSWI5 primer amplified positions 40 to 510 creating PCR products of 406 bp.

Thirty strains representing 8 *Aspergillus* species (Table 8) have been successfully sequenced with four different primer sets.

TABLE 7

PCR primers designed to amplify SWI5 gene regions in *Aspergillus* spp.

| | | |
|---|---|---|
| SEQ ID NO. 36 | AnigSWI5_1F | CAACACAGGCGGC |
| SEQ ID NO. 37 | AnigSWI5_1R | TCTGTTGTTGTTGCATC |
| SEQ ID NO. 38 | AterrSWI5_1F | AACATCGAAGGCAGA |
| SEQ ID NO. 39 | AterrSWI5_3R | CTGCATCATGTTGAGG |
| SEQ ID NO. 40 | AnidSWI5_1F | CGTCAACATCGACG |
| SEQ ID NO. 41 | AnidSWI5_1R | TGCTGTTGAATGAGATT |

TABLE 8

Initial panel used to generate SWI5 sequences

| Species name | Number of strains | Strain numbers |
|---|---|---|
| *A. fumigatus* | 5 | 505 + 359 + 2010 + 4185 + 419 |
| *A. flavus* | 3 | 2008 + 117.62 + 110.55 |
| *A. niger* | 5 | 5184 + 329399 + 2864 + 554 + 2828 + 2599 + 121 |
| *A. terreus* | 3 | 383 + 5677 + 307 |
| *A. candidus* | 0 | — |
| *A. clavatus* | 3 | 5138 + 1348 + 7944 |
| *A. glaucus* | 2 | 117314 + 542 |
| *A. nidulans* | 4 | 589 + 7063 + 808 + 670 |
| *A. versicolor* | 0 | — |
| *N. fischeri* | 3 | 19912 + 1085 + 241525 |

Thirty sequences representing 8 species of *Aspergillus* were generated. These sequences are listed in Appendix 1. Alignments were produced using the Clustal W software and homology and sequence differences were identified (FIG. 11).

Results
Primer and Probe Design:

The sequence information generated was aligned using Clustal W. Potential primers and probes for real-time PCR assays were designed to amplify and detect *A. fumigatus, A. flavus, A. niger* and *A. terreus*. These primers and probes are outlined in Table 9. These assays were evaluated on the LC480.

Figure 4:
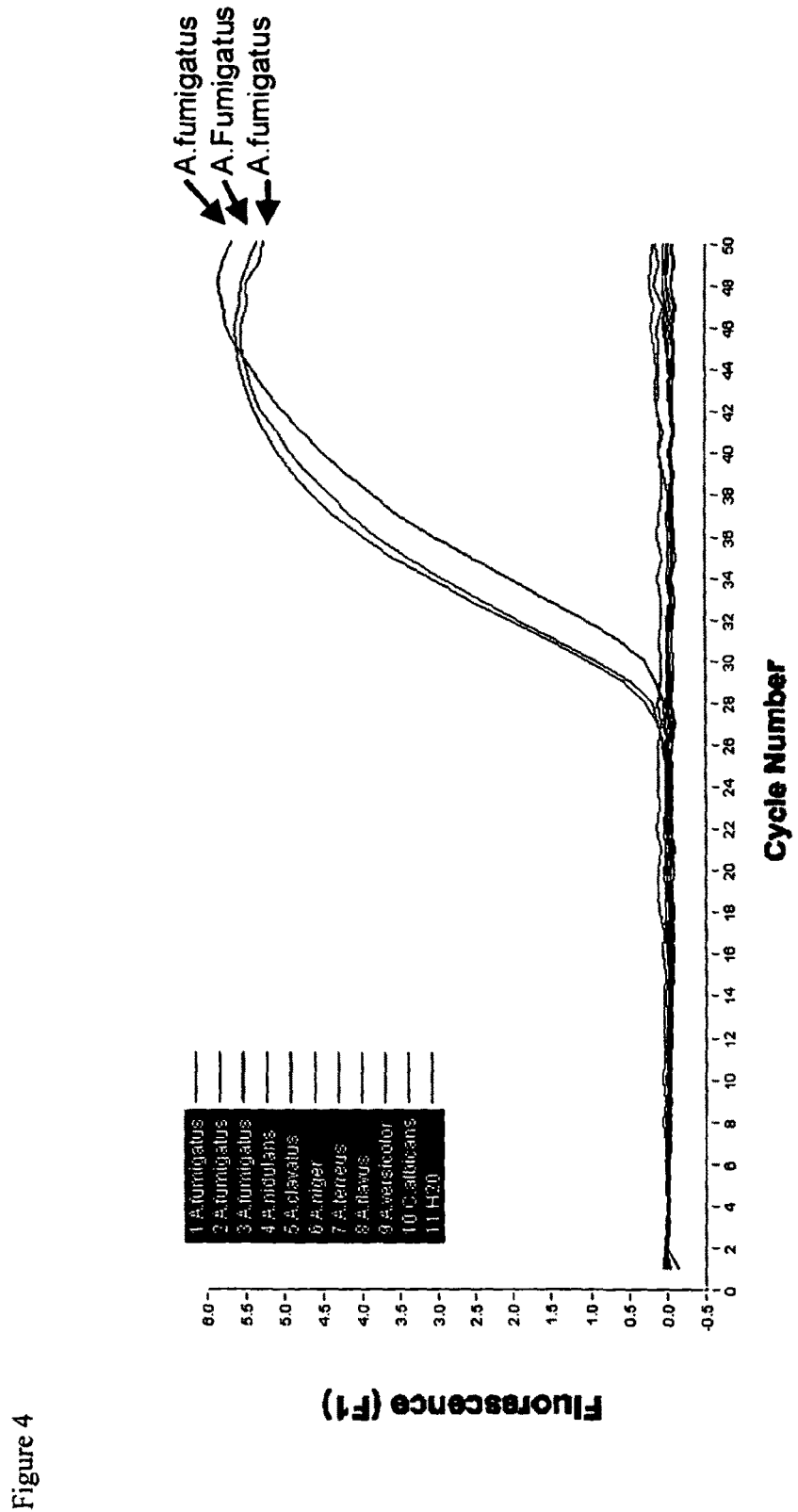
FIG. 4: Resulting amplification plot from real-time PCR assay for *A. fumigatus* based on region 1 of the SWI5 gene with TaqMan probe P1-AspSWI5-1. Specificity of the assay was tested against a panel of DNA from 6 closely related *Aspergillus* species and *C. albicans*. The 3 *A. fumigatus* strains tested were detected and no cross-reaction was observed with DNA from the other species tested.
Figure 5:
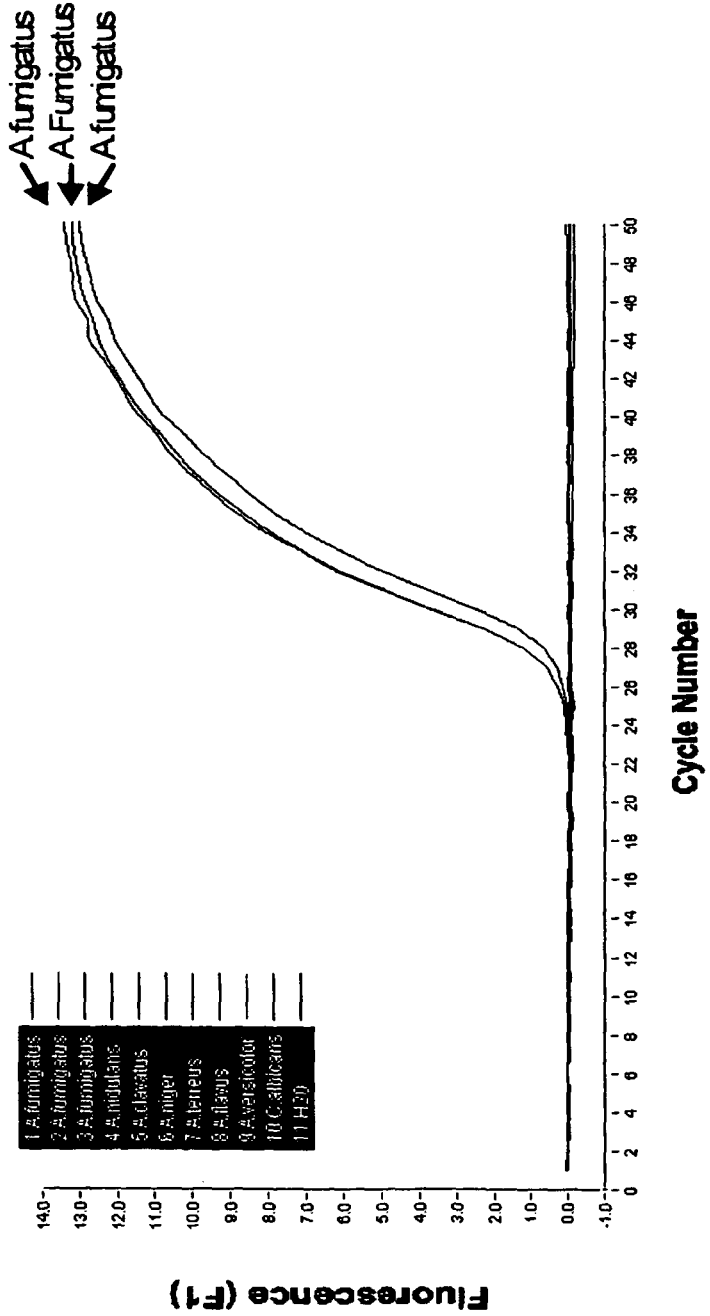
FIG. 5: Resulting amplification plot from real-time PCR assay for *A. fumigatus* based on region 3 of the SWI5 gene with TaqMan probe P1-AspSWI5-3. Specificity of the assay was tested against a panel of DNA from 6 closely related *Aspergillus* species and *C. albicans*. The 3 *A. fumigatus* strains tested were detected and no cross-reaction was observed with DNA from the other species tested.
Figure 6:
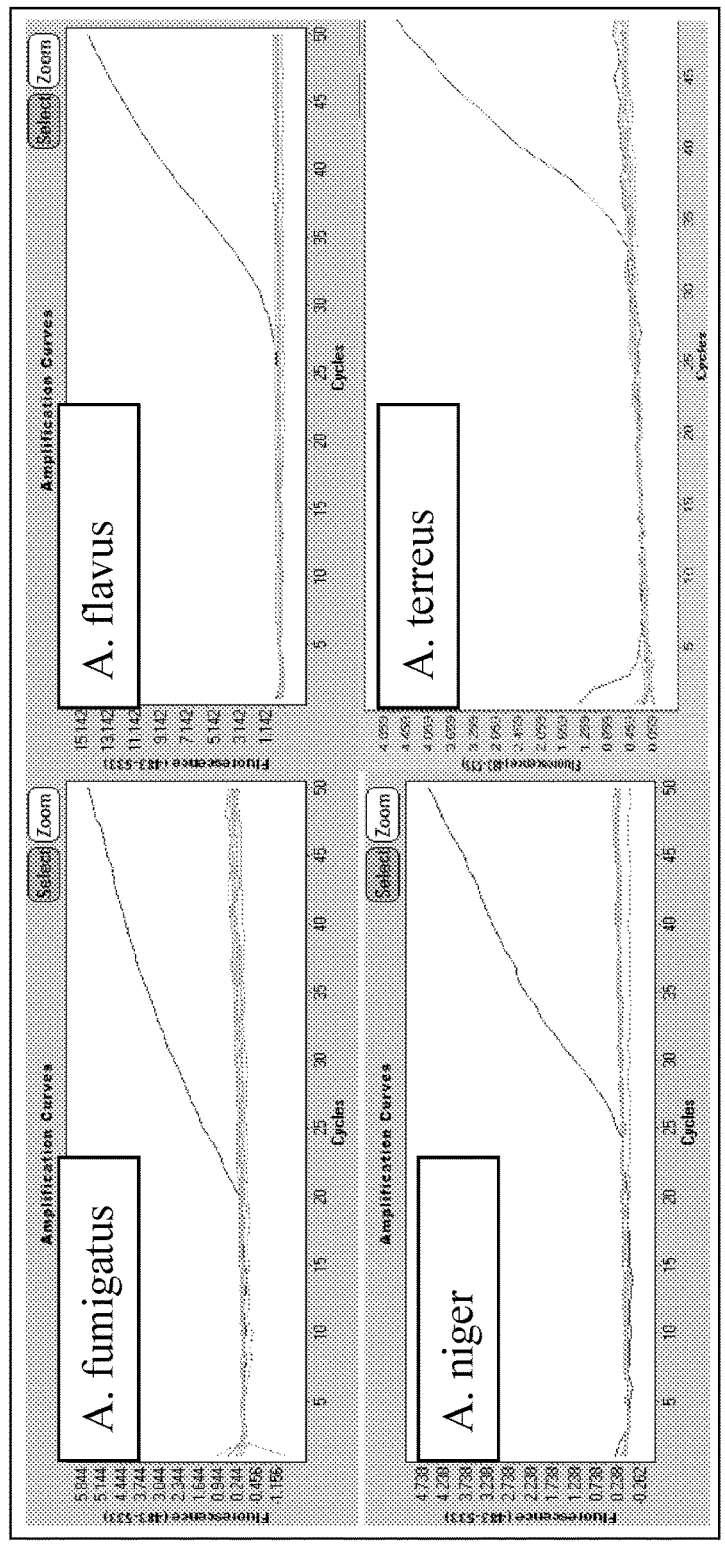
FIG. 6: Exclusivity of the SWi5 assays for *A. fumigatus*, *A. flavus*, *A. niger* and *A. terreus*. Exclusivity assays were preformed with thermocycling conditions which included denaturation and annealing at 95° C. for 5 seconds and 60° C. for 10 seconds for 50 cycles. The probes detected only the species for which they were designed, with no cross-reaction observed.

The assays which included the probes Afum_SWI5_1, Aflav_SWI5_1, Anig_SWI5_1 and Aterr_SWI5_1 proved to be specific, under thermocycling conditions which included annealing at 95° C. for 10 seconds and 60° C. for 30 seconds for 50 cycles (FIG. 6). The species tested in the assays were *A. fumigatus A. flavus A. niger A. terreus A. candidus A. clavatus A. glaucus A. nidulans A. versicolor N. fischeri*.

Figure 7:
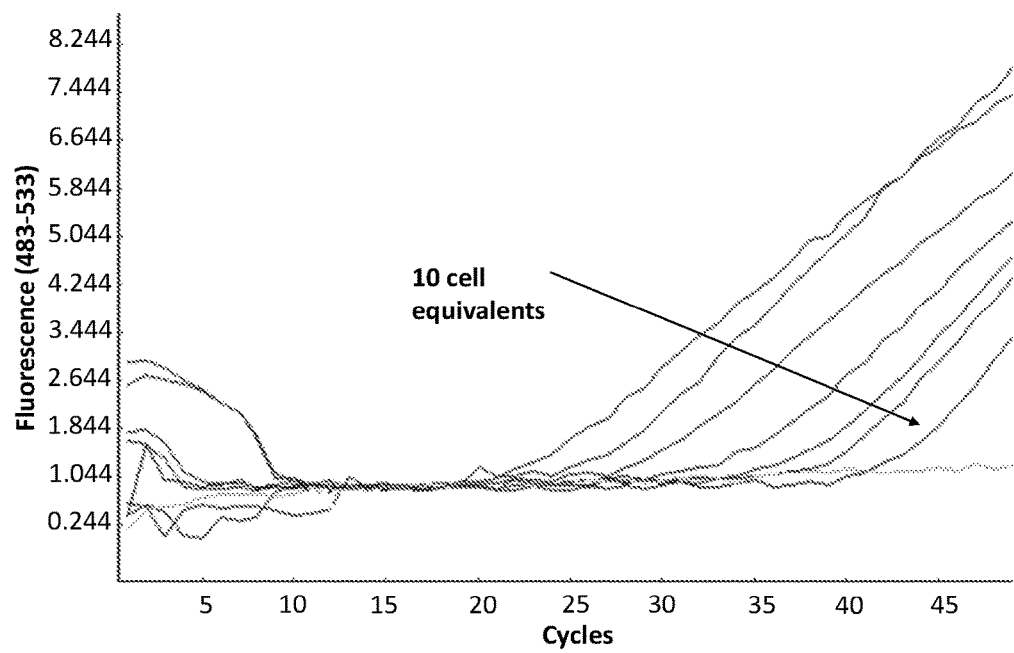
FIG. 7: Limit of detection of the *A. fumigatus* Afum_SWI5_1 assay The LOD of the *A. fumigatus* assay Afum_SWI5_1 was preformed with annealing at 95° C. for 5 seconds and 60° C. for 10 seconds for 50 cycles.
Figure 8:
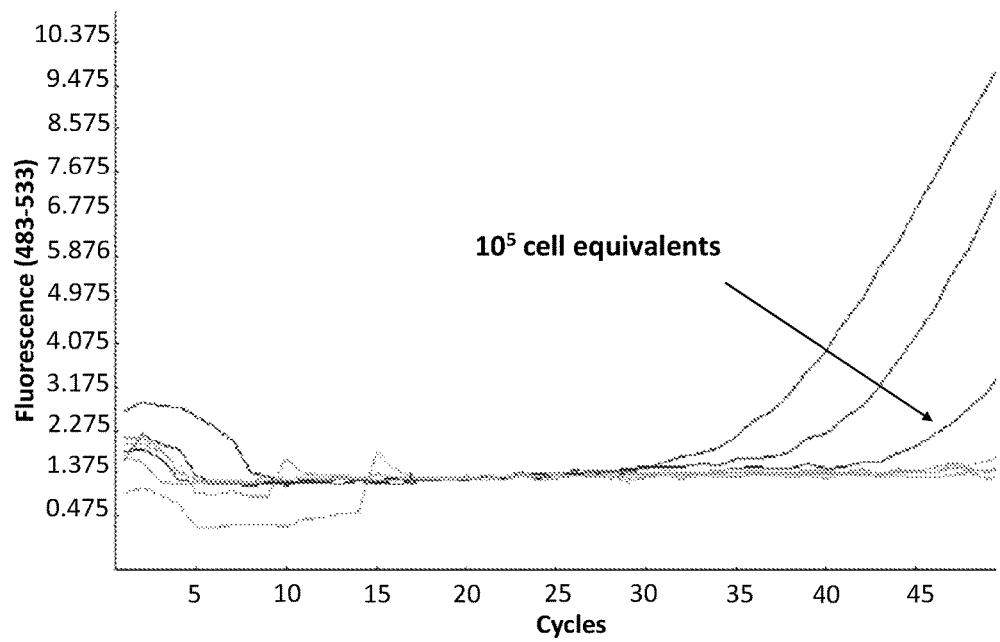
FIG. 8: Limit of detection of the SWI5 *A. terreus*, Aterr_SWI5_1 assay

To investigate the LOD of these assays cycling conditions of 95° C. for 5 seconds and 60° C. for 10 seconds for 50 cycles were tested. This was done in an effort to reduce the overall assay time. A LOD of 10 cell equivalents was obtained for the *A. fumigatus*, Afum_SWI5 assay (FIG. 7). However, the other three assays did not perform as well. The *A. terreus*, Aterr_SWI5_1 assay produced a LOD of $10^5$ cell equivalents. (FIG. 8). *A. niger* and *A. flavus* assays did not produce a LOD. (Data not shown).

To improve the assays, new primers and probes (Table 9) were designed for the detection of the SWI5 target in the species of interest. The detection limit for the new *A. fumigatus* assay Afum_SWI5_2 was found to be 2.5 cell equivalents per reaction under thermocycling conditions which included annealing at 95° C. for 10 seconds and 60° C. for 30 seconds for 50 cycles. (FIG. 9*a*).

When the annealing times of the Afum_SWI5_2 assay were reduced, an LOD of 100 cells per reaction (FIG. 9*b*) was obtained. The *A. niger* assay Anig_SWI5_2 showed potential with a detection limit of 5 cells per reaction (FIG. 10).

TABLE 9

Probes and primers for real-time PCR assays for the detection of the SWI5 target.

| | Oligo name | Sequence 5'-3' |
|---|---|---|
| SEQ ID NO. 42 | Afum_SWI5_1 | ccgtctttgacctcagaaaga |
| SEQ ID NO. 43 | Afum_SWI5_1F | cccaattctcgcaat |
| SEQ ID NO. 44 | Afum_SWI5_1R | ccggatgattcgca |
| SEQ ID NO. 45 | Aflav_SWI5_1 | tgcaacagcaacactatgct |
| SEQ ID NO. 46 | Aflav_SWI5_1F | agaccgtgcaagat |
| SEQ ID NO. 47 | Aflav_SWI5_1R | ggtttgcaattcttca |
| SEQ ID NO. 48 | Anig_SWI5_1 | cctgtgtgtagcgcagc |
| SEQ ID NO. 49 | Anig_SWI5_1F | acagtaccgcagc |
| SEQ ID NO. 50 | Anig_SWI5_1R | cttccggggtgaa |
| SEQ ID NO. 51 | Aterr_SWI5_1 | cgatctctacatgttcaacgac |
| SEQ ID NO. 52 | Aterr_SWI5_1F | cgaaagctccct |
| SEQ ID NO. 53 | Aterr_SWI5_1R | ccgtctgcggtc |
| SEQ ID NO. 54 | Afum_SWI5_2 | attccttgctggaggagaaca |
| SEQ ID NO. 55 | Afum_SWI5_2F | gcacgatgggaccgt |
| SEQ ID NO. 56 | Afum_SWI5_2R | gattgcgagaattggg |
| SEQ ID NO. 57 | Afum_SWI5_3R | ccgattgcgagaattggg |
| SEQ ID NO. 58 | Afum_SWI5_3F | acgatgggaccgt |
| SEQ ID NO. 59 | Aflav_SWI5_2F | gtctctacacatgcaacgatcgc |
| SEQ ID NO. 60 | Aflav_SWI5_2R | tgcattaccaggggacctgtt |
| SEQ ID NO. 61 | Aflav_SWI5_2 | tgtgcaagatggtaaccttctaaat |
| SEQ ID NO. 62 | Aterr_SWI5_2F | gaccatgcacgatggtaacgtt |

TABLE 9-continued

Probes and primers for real-time PCR assays for the detection of the SWI5 target.

| | Oligo name | Sequence 5'-3' |
|---|---|---|
| SEQ ID NO. 63 | Aterr_SWI5_2R | gtgggtccgaaacgttgca |
| SEQ ID NO. 64 | Aterr_SWI5_2 | agacggtgatgggagaagt |
| SEQ ID NO. 65 | Anig_SWI5_2F | atccatgcaagatggtac |
| SEQ ID NO. 66 | Anig_SWI5_2R | ctacacacaggtatcgtt |
| SEQ ID NO. 67 | Anig_SWI5_2 | tgctcgggacagcca |

TABLE 10

Thermocycling conditions
LC480 thermocycling conditions

| Step | Temp | Time | |
|---|---|---|---|
| UNG | 50° C. | 2 min | 40-50 cycles |
| Denaturation | 95° C. | 1 min | |
| Cycling | 95° C. | 5-10 secs | |
| | 60° C. | 10-30 secs | |
| Cooling | 40° C. | 1-2 mins | |

TABLE 11

Initial exclusivity panel for the SWI5 assays
Species name

A. fumigatus 2078
A. flavus 117
A. niger 2599
A. terreus 2729
A. candidus 567.65
A. clavatus 2391
A. glaucus 117314
A. nidulans 7063
A. versicolor 2916
N. fischeri 214525

Discussion

The number of yeast and fungal infections among immunocomprised patients is escalating. Contributing to this increase is the growing resistance of many yeast and fungal species to antifungal drugs. There is therefore a need to develop a fast, accurate diagnostic method to enable early diagnosis of fungal and yeast species. Early diagnosis will enable the selection of a specific narrow spectrum antibiotic or antifungal to treat the infection. The current invention provides for sequences and/or diagnostic assays to detect and identify one or more fungal and yeast species. The current inventors have exploited the sequence of the SWI5 gene in *Aspergillus* species to design primers and probes specific for regions of this gene. The SWI5 gene encodes a zinc finger DNA-binding protein required transcriptional activation of genes expressed in G1-phase and at the G1/M boundary. The sequence is conserved among closely related yeast and fungal species. The SWI5 sequence has significant intragenic sequence heterogeneity in some regions, while having significant homogeneity in others, a trait which makes SWI5 an ideal candidate for the design of primers and probes directed towards the detection of yeast and fungal species specific targets and for the detection of genus specific diagnostic targets respectively. The current invention allows the detection of yeast and fungal species.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention provides sequences and/or diagnostic assays to detect and identify one or more yeast or fungal species. The current inventors have used the SWI5 gene sequence to design primers and probes that are specific to *Aspergillus* and *Candida glabrata* SWI5 polynucleotide sequences. Such primers not only allow the detection of yeast and fungal species but also allow identification of *Aspergillus* species and discrimination between *Aspergillus* species and *Candida glabrata*. The current invention further provides for primers and probes that allow identification of *Aspergillus* species and *Candida glabrata*.

All patents, patent applications, publications, and accession numbers cited herein are incorporated by reference in their entireties.

In so far as any sequence disclosed herein differs from its counterpart in the attached sequence listing in PatentIn3.3 software, the sequences within this body of text are to be considered as the correct version.

SEQ IDs

N or x=any nucleotide; w=a/t, m=a/c, r=a/g, k=g/t, s=c/g, y=c/t, h=a/t/c, v=a/g/c, d=a/g/t, b=g/t/c. In some cases, specific degeneracy options are indicated in parenthesis: e.g.: (a/g) is either A or G.

```
SEQ ID NO 1: AspSWI5-1-F
ATCGACAACATCGTCGGCAGA

SEQ ID NO 2: AspSWI5-1-R
GCTGTTGCTGTTGCATCAGATT

SEQ ID NO 3: AspSWI5-2-F
TAGCCGCCATGCCAAGC

SEQ ID NO 4: AspSWI5-2-R
CCAGTCTCTTTGATAGAAGCA

SEQ ID NO 5: AspSWI5-3-F
CGTGGACATGACCTG AAG C

SEQ ID NO 6: AspSWI5-3-R
GTCTCTCCTCCAACTCTGG
```

SEQ ID NO 7: 1F
ATGTTAGCCAATCCAC

SEQ NO 8: 1R
ATTCCAGGCACCG

SEQ NO 9: 2F
CTTGAGGGCCAAATC

SEQ NO 10: 2R
CTCGTCCTTTCAATCC

SEQ NO 11: 3F
ACTATGCCTCGTCG

SEQ NO 12: 3R
AGCGAATACATTGCC

SEQ NO 13: 4F:
ACAAACCATATGAATGTC

SEQ NO 14: 4R
GCAGGCTCGGTT

SEQ NO 15: 5F
CCTCGAGAAGATCGT

SEQ NO 16: 5R
CTAGCAGTCCATGAAG

SEQ ID NO 17: P1-AspSWI5-1
CCAAAGTTCCTACCCTTCCAGCAC

SEQ ID NO 18: P1-AspSWI5-3
CTGACTCGGCACAGACAACGAGGA

SEQ ID NO 19:
>AF419.64-SWI51\(AspSWI5-1F) SWI5 sequences generated for A. fumigatus
TTTCAACCCCCAATGCGCTGGAAGCCGCCAAAGTTCCTACCCTTCCAGCACAGGCATTGCAGCGAATCAA

TGCGCATCGCCGTGGACAGAGTCTCGACCAACGACCTTTGCACGATGGGACCGTTTCCATTACTAACGCA

ACAGCAACTCAGCAGCACCAAATCCTTGCTGGAGGAGAACAGCATCCCCAATTCTCGCAATCGGCACATT

TCCCCCAGCACTCCTCTCCCATGCCCGTGATGCCTGAATGCCCGTCTTTGACCTCAGAAGACTTGCAAGC

ATTATCCAATTCTACCAGCAATGCGAATCATCCGGGCATGGCTTACATGAATTCGAGCTTCATTGCTATG

GGAAATCCGAGCTTGGGACTTCGACCAATGGATAACAATCTGAATCTGATGCAACAGCAACAGC

SEQ ID NO 20:
>NF1085-SWI51\(AspSWI5-1F) SWI5 sequences generated for N. fischeri
TCTCCACTCCCAATGCGCTGGAGGCCGCCAAAGTTCCTACACTTCCAGCACAGGCATTGCAGCGAATCAA

TGCGCATCGCCGTGGGCAGAGTCTCGACCAACGTCCTCGACCTATGCACGATGGGGCCGTTTCCATTACT

AACGCAACAGCAACTCAGCAGTCCCGAATCCTTGCCGGGGGAGCGCATCATCCCCGATTCTCGCAATCGG

CGCATTTCCCTCAGCATTCCTCTCCCATGCCTGTGATGCCTGAATGCCCGTCTCTGACCTCGGAAGACTT

GGAAGCACTATCCAATTCTACCAGCAACGCGAACGATCCAGGCATGGCTTACATGAATTCGAGCTTCATT

CCCATGGGAAACCCGAGCTTGGGGAATCGACCAATGGACAGCAATCTCAATCTGATGCAACAGCAACAGC

SEQ ID NO 21:
>AN670.78A-SWI51\(AspSWI5-1F) SWI5 sequences generated for A. nidulans
TCTCGACTCCCTCCGCGCTCGATGCCGCAAAACCTCCAGGCCTTTCTCCACAGGCTCTGCAGAGATACCA

TGCTCATCGCCGCGGCCAAAGTCTGGACCAGCGAGCTGTGCAAGCTCAAGCTCAGCGACAACAGCTCGTG

CAAGATGCGTCAAGTACTAACCAAACAGCACCCCAATTCGCGCCTAACTCAACCCTCGTCCCTTTAATGC

CTGACTCCCAGATCTTCGGCCAAGACGACATGCAGGCTTCAAGTCACGCCAATTACCAGACGCCTCACAG

TCTACCCTACTTGCACACGAACTTTGTCAAGGCCGATGATCAGGCTCGGGATGCTCGACCTGTCAATCAC

CACCTCAATCTGATGCAACAGCAACAGC

-continued

SEQ ID NO 22:
>AC5138-SWI51\(AspSWI5-1F) SWI5 sequences generated for A. clavatus
TCTCAACCCCCAATGTCCTGGAAGCCGTCAAAGTACCTACTCTCCCGGCGCAGGCTTTGCAGCGCATCCA

GGCGCATCGTCGGGGACAGAGTCTCGATCAGCGATCTGTGCATGCCCAACGATCTCGTCCCATGCAAGAT

GGTGGTCCTTCCATTACTAACCCAGCAGTGCCTCAGCAACCCCAGATGGTTGCCGGGGGAGCGCCTCATC

AGCAATTCCCTCAATCGTCGCAATTCCCCCAGCAACTTACCCCCATGCCTATGATGCCCGAATGTCAGTC

GTTTCCCTCCGACGAGTTGCAGGCGTTGTCCGGACAGAGCATCAACGTGAATCAACCGGACATGGCTTAT

ATGATTCCAGACTTCGTCAACATCGGAAATCATTGCGTTGGGAACCGACCCATGGTCAGCAACCTCAATC

TGATGCAACAGCAACAGC

SEQ ID NO 23:
>AN329399-SWI51\(AspSWI5-1F) SWI5 sequences generated for A. niger
TCTCGACGCCGTCCGCTCTTGATGCCGTGAAAGCCCCCAGCCTTCCGGCGCAAGCGATGCATCGTTATCA

TGCCCATCGTCGAGGACAGAGCTTTGACAACAGAGCTTTGCGCGTCCAGCGATCGCAATCCATGCAAGAT

GGTACAAATCATACTACTAACTCTACAGTACCGCAGCAGCACCATTCGAATATGCTCGGGGACAGCCAAC

ACCAACGATACCTGTGTGTAGCGCAGCCGTCGTTTCCCCAGCAATCAGCCCCCATGCCCATGATCCCCGA

CTGTTTCACCCCGGAAGAGGTGCAAAACCTTCAAAGTCACAATGGCCAGGACAGTCAACCAAGCATGGCC

TACCTGAATGCGCCCTTCGCAAAGGACGTTCCGCACATGAACATGCAGTTCAATCTGATGCAACAGCAAC

AGC

SEQ ID NO 24:
>AF2008-SWI51\(AspSWI5-1F) SWI5 sequences generated for A. flavus
TTTCAACACCTTCCGCTCTTGATGCCGCCAAAGTCCCCAGTCTTCCTGCCCAGGCAATGCACCGATACCA

TGCTCACCGTCGCGGCCAGAGCCTAGACCAGAGGTCTCTACACATGCAACGATCGCAGACCGTGCAAGAT

GGTAACCTTCTAAATACTAACGCAACAGGTCCCCTGGTAATGCAACAGCAACACTATGCTCGTTCGGCGC

AACCGACACCCATGCCCATGATGCCTGAGTGCCAGACTTTCAGTCCTGAAGAATTGCAAACCCAACCAAG

TATGGGATACATGAGCCCAGCCTTCGCCAAGGCCGAGACCCCGGCGCTGGAGAGTCGGCCGATGAACCTC

CATCTCAATCTGATGCAACAGCAACAGC

SEQ ID NO 25:
>AF416.64-SWI53\(AspSWI5-3F) SWI5 sequences generated for A. fumigatus
GTCACGCCAAGATTCACACTGGAGACAAACCATATGAATGTCTTTGTGGCAATGTATTCGCTAGGCACGA

TGCTCTGACTCGGCACAGACAACGAGGAATGTGCATCGGCGGTTACAAGGGTATTGTGCGCAAGACAACC

AAGCGTGGCCGTCCAAAGAAACATCGACCAGAGTTGGAGGAGAGAC

SEQ ID NO 26:
>NF1085-SWI53\(AspSWI5-3F) SWI5 sequences generated for N. fischeri
GTCACGCCAAGATTCACACTGGAGACAAGCCATATGAATGTCTCTGTGGCAACGTATTCGCTAGGCACGA

TGCTCTGACTCGGCACAGGCAACGAGGAATGTGCATCGGCGGTTACAAGGGTATTGTGCGCAAGACAACA

AAACGTGGTCGTCCGAAGAAACATCGACCAGAGTTGGAGGAGAGAC

SEQ ID NO 27:
>AN670.78-SWI53\(AspSWI5-3F) SWI5 sequences generated for A. nidulans
GCCACGCGAAGATCCACACAGGAGACAAGCCGTACGAATGTCTATGCGGTAATGTTTTTGCCCGGCACGA

TGCCCTAACTCGACACCGCCAGAGGGGAATGTGCATTGGTGGTTACAAGGGAATTGTGCGTAAGACAACG

AAACGTGGCCGTCCTAAGAAGCACCGCCCATAGTTGGAGGAGAGAC

SEQ ID NO 28:
>AN1329399-SWI53\(AspSWI5-3F) SWI5 sequences generated for A. niger
GTCATGCTAAGATCCATACCGGCGACAAGCCTTACGAGTGCCTCTGTGGAAATGTATTTGCGAGACACGA

CGCCTTGACTCGACACAGACAGCGGGGTATGTGCATTGGCGGCTACAAGGGAATTGTGCGCAAGACAACG

AAACGGGGTCGTCCGAAGAAGCACCGACCAGAGTTGGAGGAGAGAC

SEQ ID NO 29:
>A. fumigatus gi|70999549|ref|XM_749401.1| Aspergillus fumigatus Af293
C2H2 transcription factor (Swi5), putative (AFUA_3G11250) mRNA,
complete cds
ATGTTAGCCAATCCACATAGTAATCTGCACGAGCGTTATCGACAACATCGTCGGCAGATTTCAACCCCCA

ATGCGCTGGAAGCCGCCAAAGTTCCTACCCTTCCAGCACAGGCATTGCAGCGAATCAATGCGCATCGCCG

TGGACAGAGTCTCGACCAACGACCTTTGCACGATGGGACCGTTTCCATTACTAACGCAACAGCAACTCAG

CAGCACCAAATCCTTGCTGGAGGAGAACAGCATCCCCAATTCTCGCAATCGGCACATTTCCCCCAGCACT

CCTCTCCCATGCCCGTGATGCCTGAATGCCCGTCTTTGACCTCAGAAGACTTGCAAGCATTATCCAATTC

TACCAGCAATGCGAATCATCCGGGCATGGCTTACATGAATTCGAGCTTCTTTGCTATGGGGAATCCGAGC

TTGGGACTTCGACCAATGGATAACAATCTGAATCTGATGCAACAGCAACAGCAGCAAAATGCCCACGTCT

CATGCGTCAATAGCCTTGAGGGCAAATCCTCGACAACGGTGCCTGGAATTTCTACCAGCAAGGCCAGCT

CCCTACGACGCTTCGGTCTCAAGTCAACAATCTTTCGGCCGATGGGAGACGACAGTCTGTTCAGTCAGAT

ATCACCCCCTCGCAACGACCACATACCCCCAAGCAAGCAAATACGCACTACTTTCCCATAACGCCAGCGA

CAACTCCGTTTAAGAAACCGGCGGAACTTGCTCAGTATAGTACGGACATGCAGTCCACCCCCACCAAGGA

GACAGGCCGCTCTGCACCCGCATCAGCCCAGTCGGTATACATGCAACGAGCCAAATCCCTCCAAGGAGTT

GCGGGGTCTACCTTTTCCAACTCCAAAATCGAGATGCCCTCCCCCCCGAACACGGCTTCATTTGAAATTG

ACAATTTTGATGCGTTTAGCAGTCAGCAGGGTTCCAGTTTCGAGATTTCCGAGTCAGAGAATTTATCGCA

GAGTCACTATGCCTCGTCGTCAGCAACCTCGTCCTTTCAATCCTCCCCAGAGCTAGCCGCCATGCCAAGC

CCCGAAGACAATCACGAGAAGGCTCATAAGCTGCCCATCTTCCCTGCCGCGTCCAATCGGCCAGCGCACA

GGAAGGCGCTGAGTACCAGCTCCAGTTCCACCTTGACGAAACCCGGCTCTCTCCAAGAGTGGCTTCAAT

TGATAGCCTTAACCTTGATGCTAGGGTTCATGCTTCTATCAAAGAGACTGGGATCACCATCGATGAGATC

GCCTCCTACATCTCTGGCCCTGACCCGGAGGATGGAAAGTGGGTTTGCCTTCACCCCGGCTGCGAGCGGC

GGTTCGGAAGAAAAGAAAATATCAAGTCCCACGTCCAAACCCACCTTGGTGATCGCAATATAAGTGTGA

TCATTGCAACAAGTGCTTCGTTCGTGGACATGACCTGAAGCGTCACGCCAAGATTCACACTGGAGACAAA

CCATATGAATGTCTTTGTGGCAATGTATTCGCTAGGCACGATGCTCTGACTCGGCACAGACAACGAGGAA

TGTGCATCGGCGGTTACAAGGGTATTGTGCGCAAGACAACCAAGCGTGGCCGTCCAAAGAAACATCGACC

AGAGTTGGAGGAGAGACAGGATAAGGCAGCCAAGACACGCCAGAGAGTCGCCGAAAAGTCATCCCATGAC

TCCTCGTCCGGGTGTGTTGATTCCCCCAACTCGCCGCCTTCCGAAATCCTTGAAAATATGAGTCTTCACG

GGGGATCGAGCCCTAAAGAGAATATGCCCGCGTTCATTCAGCCCAACTTTTCCTTGCCTCCATCGGCGTT

TACTTTCACGCCTCCTGCGTCTCCCCGACAGAGTCTTGGAAACCAGCCATCGCCCGCTCAGAGTCGCCGC

TCACTCACGCCCAGTAGCGAGGATGAAATGCTGCCTTTGTCTCCCTCCAAGCGCCCCCTCGAGAAGATCG

TTGAAGAACCGAGCCTGCCTTTCACTTCGAGTGCCGACCCATACACCGATATTGCTGCCTCCACCGCGGA

GCTGTCTTCTCCACATACGGCTCCCACCTTGGCTGATTCGTCTCACGGCTCCGACCTCGATATTTTCATC

AGCACGGATAGCTCCGCCAATTTCAAGCATGAATTTCCCGATCTGAGTGACCCCGACATGGCCGCTTTCC

CCGACTATGTCAATGGGTCTACCTTCGAACCCGGAATGGATCTGTTCTCGAGCAAGACATTCTCTGCCGG

TACCTCGATGAACGAGGACTTCTTTTCACTCCAATTCCAGGTTGATGATATGACCAAAGAATTCTTCATG

GACTGCTAG

SEQ ID NO 30:
>N. fischeri gi|119491684|ref|XM_001263336.1| Neosartorya fisch-
eri NRRL
181 C2H2 transcription factor (Swi5), putative (NFIA_066040) mRNA,
complete cds
ATGTTAGCCAATCCACATAGCAATCTGCACGAGCGTTATCGACAACATCGTCGGCAGATCTCAACCCCCA

ATGCGCTGGAAGCCGCCAAAGTTCCTACCCTTCCAGCACAGGCATTGCAGCGAATCAATGCGCATCGCCG

TGGACAGAGTCTCGACCAACGACCTTTGCACGTCCAACGTCCTCGACCTATGCACGATGGGGCCGTTTCC

ATTACTAACGCAACAGCAACTCAGCAGCACCAAATCCTTGCCGGGGAGCGCAGCATCCCCGATTCTCGC

AATCGGCGCATTTCCCCCAGCACTCCTCTCCCATGCCCGTGATGCCTGAATGCCCGTCTTTGACCTCGGA

AGACTTGCAAGCATTATCCAATTCTACCAGCAATGCGAACCATCCGGGCATGGCTTACATGAATTCGAGC

TTCATTACCATGGGAAATCCGAGCTTGGGGATTCGACCAATGGATAACAATCTAAATCTGATGCAACAGC

AGCAGCTGCAAAATGCTCACGTCTCATGCGTCAATAGCCTTGATGGCCAAATCCTCGACAACGGTGCCTG

GAATTTCTACCAGCAAGGCCAGCTCCCTACGACGCTTCGGTCTCAAGTCAACAACCTTTCGACCGATGGG

AGACGACAGTCTGTTCAGTCAGATATCACCCCCTCGCAACGACCGCATACCCCCAAGCAGGCAAATACGC

GTAAGTTATCCGTTCAGTCATACTGGTCATTTTTCTCCCAGCCACTAACGACCGATCCAGACTACTTTCC

ATAACGCCAGCGACAACTCCGTTCAAGAAACCAGCGGAACTTGCTCAGTATAGTACGGACATGCAGTCC

ACCCCCTCCAAGGAGACAGGCCGCTCTGCACCCGCATCAGCCCAGTCGGCATACATGCAACGAGCCAAAT

CCCTCCAAGGAGTTGCCGGGTCTACCTTTTCCAACTCCAAAATCGAGATGCCCTCCCCCCCGAACACTGC

TTCATTTGAAATTGACAATTTTGATGCGTTTAGCAGTCAGCAGGGTTCCAGTTTCGAAATTTCCGAGTCA

GAGAATTTATCGCAGAGTCACTATGCCTCGTCGTCAGCAACCTCGTCCTTTCAATCCTCCCCAGAGCTAG

CCGCCATGCCAAGCCCAGAAGACAATCATGAGAAGGCTCATAAACTGCCCATCTTCCCTGCCGCGTCGAG

TCGGGCAACCCACAGGAAGGCGCTGAGTACCAGCTCCAGTTCCTCCTTGACGAAACCCCGGCTCTCTCCA

AGAGTGGCTTCAATTGATAGCCTTAACCTTGATGCTAGGGTTCATGCTTCTATCAAAGAGACTGGGATCA

CCATCGATGAGATAGCCTCCTACATCTCTGGCCCCGACCCGGAGGATGGAAAGTGGGTTTGCCTTCACCC

CGGCTGCGAACGGCGGTTCGGAAGAAAAGAGAATATTAAGTCACACGTCCAAACCCACCTTGGTGATCGC

CAATATAAATGTGATCATTGCAACAAGTGCTTCGTTCGTGGACATGACCTGAAGCGTCACGCCAAGATTC

ACACTGGAGACAAACCATATGAATGTCTTTGTGGCAACGTATTCGCTAGGCACGATGCTCTGACTCGGCA

CAGACAACGAGGAATGTGCATCGGCGGTTACAAGGGTATTGTGCGCAAGACAACAAAACGTGGTCGTCCA

AAGAAACATCGACCAGAGTTGGAGGAGAGACAGGACAAGGCAGCCAAGACACGCCAGAGAGTCGCCGGGA

AGTCATCCCTTGACTCCTCGTCCGGGTGTGTTGATACCCCCAACTCGCCGCCTTCCGAAATCCTTGAGAA

TATGAGTCTTCACGGTGGATCGAGCCCCAAAGAGGATATGCCCGTGTTCATCCAACCCAACTTTTCCTTG

CCTCCATCGGCGTTTACTTTCACGCCTCCTGCGTCTCCGCGACAGAGTCTTGGAAACCAGCCATCGCCCG

CTCAGAGTCGCCGCTCACTCACACCCAGTAGCGAGGATGAAATGCTGCCTTTGTCGCCCTCCAAGCGCCC

CCTCGAGAAGATTGTTGAAGAACCGAGCCTGCCTTTCATTTCGAATGCCGACCCATATACCGATATTGCT

ACCTCCACCGCCGAGCTGTCTTCTCCACATACGGCTCCCACCTTGGCTGATTCGTCTCACGGCTCCGACC

TCGATATCTTCATCAGCACGGACAGCTCCGCCAACTTCAAGCATGAATTTCCCGATCTGAGTGACCCCGA

CATGGCCGCTTTCCCCGACTATGTCAATGGGTCTACTTTCGAGCCCGGACTGGATCGTTCTCGAGCAAG

ACATTCTCTGCCGGTACCTCGATGAACGAGGACTTCTTTTCACTCCAATTCCAGGTTGATGATATGACCA

AAGAATTCTTCATGGACTGCTAG

SEQ ID NO 31:
>A. clavatus gi|121705723|ref|XM_001271124.1| Aspergillus clava-
tus NRRL
1 C2H2 transcription factor (Swi5), putative (ACLA_039140) mRNA,
complete cds
ATGTTTGCCAATCCGCACAGTAACCTTCACGAGCGGTATCGACAACATCGCCGGCAGATCTCAACCCCCA

ATGTCCTGGAAGCCGTCAAAGTACCTACTCTCCCGGCGCAGGCTTTGCAGCGCATCCAGGCGCATCGTCG

GGGACAGAGTCTCGATCAGCGATCTGTGCATGCCCAACGATCTCGTCCCATGCAAGATGGTGGTCCTTCC

ATTACTAACCCAGCAGTGCCTCAGCAACCCCAGATGGTTGCCGGGGGAGCGCCTCATCAGCAATTCCCTC

AATCGTCGCAATTCCCCCAGCAACTTACCCCCATGCCTATGATGCCCGAATGTCAGTCGTTTCCCTCCGA

CGAGTTGCAGGCGTTGTCCGGACAGAGCATCAACGTGAATCAACCGGACATGGCTTATATGATTCCAGAC

TTCGTCAACATCGGAAATCATTGCGTTGGGAACCGACCCATGGTCAGCAACCTCAATCTGATTCAACAGC

AGCAACTGCACAATCCCCATATCATTGCAAACAGTGCGCTCGATGGCCAGATTCTCGACAACAGCGCTTT

CAATATCTATCAGCATGGCCTTCGACCCCAGACAAACAATCTTTCAGTGGATACACGACGATTGTCAGTT

CACTCGGATGTAAGCCCCTCGCATCAGCCACATACGCCCAAGCAGACGAATTCGCGTAAGTCCACTGTCT

CTCCATGGCGAATCCTGAGTCCATCAACTCCCGACTCACGACTGGAATCAGAATATTTCCCGATTACCCC

AGCAACAACTCCTTTCAAGAAAACAGCCGAACTTGCTCAGTATAGCACGGACGTCCAGACAACTCCCTCC

AAGGAGCAACGCTTTTCGGCCGCTCAGGCGGCCTACATGCAGCGGGCCAAGTCCCTTCAGGGCGTGGCCG

GAACTACCTTTTCTCAACCAAAGATCGAGATGCTTTCCCCCCATAACACAGGTTCGTTTGAAATTGAGAG

TTTTAATACTTTTGGCAGTCAGCAGGGTTCCACTTTTGAATTTTCCGAGTCAGAGAATTTGTCGCAAGGC

CAGTATGCCTCGTCGTCAGCAACGTCATCCTTCCAATCCTCCCCAGAGCTAGCGGCCATGCCAAGCCCCG

AGGACCATAACGAAAAGGCGCACAAGATCCCCATCTTCCCAGCCGTATCCAGCCGTATCAGTCACAAGAA

GACTTTGAGTCTTCCCGCTAGCACTTCGCCGGCGAAACCCAAGCTTTCTCCCAGAGTGGCGTCCATAGAC

AACCTGAACCTCGATGCCCGTGTGCACGCCTCAATCAAAGAGACCGGTGTCACCATTGACGAGATTGCTT

CCTACATCTCCGGCCCGGATCCAGAGGATGGAAAGTGGGTTTGCATTCACCCTGGTTGCGAGCGGCGGTT

TGGAAGAAAAGAAAACATCAAGTCACACGTCCAAACACATCTGGGAGATCGCCAGTATAAATGTGACCAT

TGCAACAAGTGTTTCGTCCGCGGACATGACCTGAAGCGTCATGCTAAGATCCACACTGGAGACAAACCGT

ACGAATGCCTTTGCGGGAACGTTTTCGCTAGACACGATGCTTTGACCCGCCACCGACAGCGAGGCATGTG

CATCGGTGGTTACAAGGGAATTGTGCGCAAGACAACAAAACGCGGTCGTCCTAAGAAACACCGGCCGGAG

ATGGATGAAAGGCAGGACAAAGCCGCCAAAACACGCCAGCGAGTCGCTGATAAGACATCCTTTGACTCCT

TGTCTGGGACAGATGTTGCGCCGAATTCACCACCATCCGAAGTTCTTGAGAACATGAGCCTACACGGGGA

TCCAAGCCCAAAAGAAGAGATGCCCGCGTTCAACCAGCCCGATTACTCGTTACCACCCTCTGTTTTCACC

TTCACGCCTCCTGCATCGCCAGGGCACAACCTTGGAAACCGGCCATCACCGAATCAGAGTTACCGGTCTC

TCACGCCCAGTAGTGAAGATGAAATGCTGCCTTCGTCGCCTATCAAGCGGCCTCTAGAGAGGATCGCCGA

AGAGTCGGGGTTGCCTTATATCGAACATGCAGATCTCTATACTGAGATCGCCACTTCTGCTGCTGATCTG

TCGTCTCCACACACCGCTCCTACCTTGGCCGATTCATGTCACGGCTCTGATCTCGATATCTTCATCAGCC

CTGACAGCTCTGCGAACTTCAAACATGAATTCCCTGAGCTGAGTGACATGGCCGCTTTCCCTGACTATAC

GAATACCTCTACCTTCGACGCCGGACTGGACCTCTTCTCAAGCAAGAACTTCTCCACTGTTCCTTCAATG

AATGACGATTTCTTCTCCTTCCAATTCCAGGCTGACGACCAACCCTTGGATGTCATGGCCAAGGAGTTCT

TCGCCGACTGA

SEQ ID NO 32:
>A. terreus gi|115396393|ref|XM_001213836.1| Aspergillus terreus
NIH2624 conserved hypothetical protein (ATEG_04658) mRNA, complete cds
ATGCTATCCACCCAGCACCGAAATTCGCATGACCGGCACCGGCAACATCGAAGGCAGATTTCCACCCCTT

CTGCCATTGACGCCGCGAAAGCTCCCTCCCTGCCGGCGCAGGCATTGCATCGATACCATGCTCATCGCCG

AGGCCAGAGTTTCGACCAACGATCTCTACATGTTCAACGACCGCAGACCATGCACGATGGTAACGTTTCA

GCTACTAACAACACAGGACCGCAGACGGTGATGGGAGAAGTGCAGCAGCTGCAACGTTTCGGACCCACAG

GACACTCAGGCTATCACCAACACTCGGCTTCTATGCCGGTAATGCCCGAGTGCCAACCATTGAGCCAGGA

AGACTTCCAGACCCTGGGCAATCGCAATGTCCCAGACAACCAGACCGCCATGACCTATATGACGCCCGCG

CTGCACCTCAACATGATGCAGCAGCAGCAGCAGCTTCAACACGCAAGAGTGCATTCCAACAATGCGCTTG

ATGGTCAGCTTCTCGAGAATGGTCCGTGGGACATGTATCAGCACGACAACCTTGCTGCGCCGCTCCCACA

GCAACCCAACACCATTCCCGCGGGCTTAAGGCGTCTGTCAGCTCAATCAGAGACCACTCCTGCGCAACGA

-continued

```
CCACTCACTCCGAAGCATAACAATACCAATTACCTTCCTATCACCCCTGCCACAACGCCCTTTAAAAAAT

CAGTGGATCTTGCCCAGTACAGCGGCGAACTCCATTCAACTCCCACCAAGGACCAGAGCCTTTCCGCACC

CGGCTCTTCCCAATCGTTCATGCAACGTACGAATTCACTCCAAGGAGTGGCTGGAACAACATTCTCCCAA

CCCAAGCTTGAAGTCCCCTCCCCCCCAAACACTGCGTCATTTGATGTGGACAGCTTCGATGCTTTTGACT

ATCAACAGGAATCCAGTTATGAAATCCCCAAGTCTGAGAGCCTCAACCATTATGCCTCGTCGTTGGCGTC

GTCATCATTCAACTCATCCCCGGAACTCGCGGCTATGCCGTGTCCACAAGACGGCGGTAGAGCGCAAAAG

CTCCCCATCTACCCGGTCACACCAAGTCGCACAAACATGAAGAAGTCTCCCAGCGTCACCTCCAACTCGT

CCGCGTCGAAGCCAAAGCTCTCTCCAAGGGTCGCAACCATTGACAGCCTCAACCTGGATGCCAGAGTCCA

TGCATCCATCAAAGAAACTGGCGTCACAATCGACGAGATTGCCTCGTACATAAGCGGCCCTGATCCAGAG

GACGGAAAATGGGTGTGTCTGCACCCAGGATGCGAGCGTCGGTTTGGAAGAAAAGAAAACATCAAGTCCC

ATGTTCAGACCCATCTGGGTGACCGTCAGTACAAGTGCGACCACTGCAACAAATGTTTTGTCCGCGGCCA

CGATCTCAAACGCCATGCCAAAATCCATACCGGTGACAAGCCGTACGAGTGTCTCTGCGGTAATGTGTTC

GCTCGACACGACGCATTGACGCGCCACCGACAACGGGGCATGTGCATCGGTGGTTACAAGGGAATCGTTC

GCAAGACAACGAAACGTGGTCGCCCCAAGAAACATCGGCCCGAGATGGACGAGAGACAAGATAAGGCATC

TAGAACCCGCCAGCGGCTCGCCGAGAAGACATCTTTCGACTCCTCCAGCTCAGATATCTCTCGCAATTCT

CCCCCATCGGAGGTACTGGAACAAATGAGCCTTCACGGCTCTAGCCCCGCCGAACAGATGCCGGTATTCC

ATAATCCAAACTACTCGCTGCCTCCGGAGGTCTTTACGTTCACTCCTCCTGCATCCCTGGCGGTAGCGC

TGGAAACAACCCTTCTCCAAGCCACAGCCAACGCTCCCTCACGCCTAGCACCGAGGACGAAATGCCACCT

TTGTCACCTTCCAAGCAACCTCTGTCAAAGATTGTGGAAGAATCTGGCTTGCCTCTTATGCCCGATTGTG

CATACACCAATGCCACCAACTCAACCATCAATGCTTTGTCGTCCCCGCATACCGCACCCACCCTGAGTGA

TGCTTCAAACGGCTCCGATCTTGACATCTTTATCAGCCAAGATCCGTCCACCGGCTTCGGCAAGCATGAG

TTTTCCGACCTCACTGATTCCGACATGGCGGCATTCCCTGACTATGTGAACGGCTCTTCCTTCGAAGGCG

GAATGGACCTCTTCCAAGGAAAGGGGTTCTCCAATGCTCCCCCAATGAGCGACGACTTCTTCTCCTTCCA

ATTTCAAGTTGACGAGCAACCATCCGATGTTATGACCCGCGATTTCTTCATGGATTAA

SEQ ID NO 33:
>A. niger gi|145232922|ref|XM_001399797.1| Aspergil-
lus niger CBS 513.88
hypothetical protein (An02g07000) mRNA, complete cds
ATGCTGTCCACGGCGCACAGCAACCTTCATGAGCGACATCGACAACACAGGCGGCAGATCTCGACGCCGT

CCGCTCTTGATGCCGTGAAAGCCCCCAGCCTTCCGGCGCAAGCGATGCATCGTTATCATGCCCATCGTCG

AGGACAGAGTTTTGACAACAGAGCTTTGCGCGTCCAGCGATCGCAATCCATGCAAGATGGTACAAATCAT

ACTACTAACTCTACAGTACCGCAGCAGCACCATTCGAATATGCTCGGGGACAGCCAACACCAACGATACC

TGTGTGTAGCGCAGCCGTCGTTTCCCCAGCAATCAGCCCCCATGCCCGTGATCCCCGACTGTTTCACCCC

GGAAGAGGTGCAAAACCTTCAAAGTCACAATGGCCAGGACAGTCAACCAAGCATGGCCTACCTGAATGCG

CCCTTCGCAAAGGACGTTCCGCACATGAACATGCAGTTCGACCTGATGCAACAACAACAGATGCACAGCA

CTAAGGTTCCGTGCGGGTCTGGAACGGAAGGTCATTTTTTCGAGACGGGACTTTGGGACTTTTACCAGCC

AACTTTCCCCCCTCACGCTGATGTAAGGAAGTTATCGGTGCAGTCGGATGCTACTCCGTCTCAGCACCCG

CATACGCCTAAGCACGGCAATACACAGTATGCCCCGATTACACCAGCAACAACACCATTCAAGCAAACCG

TGGGCCTAGCTCAGTACGGTGGGACATCCAGTCAGGATCCACCAAAGATCAGGGTAGCGCGATGCCCGG

ATCAGCCCAGTCGTCGTACATGCAGCGAGCAAAGTCTCTCCAAGGCGTGGCTGGAACTACTTTCACGCAG

CAGAAGTTTGATGTTTCTACCCCCCCGAACACAGCATCATTTGAAGTGGATAACTTTGATACTTTTAACT

ATGAGCAGGGTTCTAGCTTTGAGGTTCCTAAATCGGAAAGTCTGTCACAAAGCCAGTATGCATCGTCGTC
```

-continued

GTCGGCATCATCATCATCCTTCATGTCATCTCCCGAGCTTGCGGCTATGCCTTGCCCCGAAGATGGAGGT

GCAAAGACCCCCAAAATCCCTATCTATCCCGCCACTCCCAGCCGTCCGCATCACAGAAAGACGCCCAGTG

CAACACCTAGCTCATCGGCCAAGCCAAAGCTTTCTCCGCGCGTTGCGTCTATCGATAACCTGAACCTCGA

CGCTCGCGTGCAAGCATCAATCAAAGAAACGGGTGTCACCATTGACGAGATTGCTTCGTACATTCATGGG

CCTGACCCGGAGGACGGGAAATGGGTATGCCTGCACCCCGGCTGCGAGCGCCGCTTTGGAAGAAAGGAGA

ATATCAAGTCACATGTCCAGACTCACCTGGGCGACCGCCAGTACAAGTGCGATCATTGCAACAAATGCTT

TGTTCGCGGTCATGACCTTAAGCGTCATGCTAAGATCCATACCGGCGACAAGCCTTACGAGTGCCTCTGT

GGAAATGTATTTGCGAGACACGACGCCTTGACTCGACACAGACAGCGGGGTATGTGCATTGGCGGCTACA

AGGGCATTGTGCGCAAGACAACGAAACGGGGTCGTCCGAAGAAGCACCGACCAGAGATGGATGAGAGACA

GGACAAAGCATCGAGAACGCGTCAGAGGATTGCAGAGAAGTCATCTTTCGACTCGTCCACATCCGAGTCC

TCACGCAACACGCCTCCTTCCGAAGTCTTCGAAAACATGAGCCTGCATGGTTCTAGCCCGGCGGAAGAGA

TGCCAGTGTTCAACAACCCCAACTACTCGTTGCCACCAGAGGTTTTCACATTCACGCCTCCTGCATCTCC

CGGTTACAGCGTGGGAATCAAGCCATCGCCTTCTCGGGACGAGCGATCGATCACCCCCAGCTCAGAAGAT

GAAATGCTTCCTTCCTCACCATCAAAGCAGCACCTCGAGAGCCTCGTCACAGACTCCAGCTTGCCTTACA

TGTCTGATCCGGAGACATGCCCGTATACAGATGCTTCCGGCGCTGCTAGCCATTCTCTATCTTCACCCCA

TGCCGCTCCCACCCTGTCCGAATCATCTAACGGCTCTGATCTCGACATTTTTATTAGCCAGGATTCGACC

TCTGGTTTTGGAAAGCCCGAATTCGGAGACCTGGCTGATCCCGACATGGCCCCGTTCCCAGACTATGTGA

ACACGACGTCCTTTGAAGGTGGTCTGGAACTGTTCCCCAACAAGCCCTTCTCCTCGGGCCCCGTCATGGC

CGACGACTTCTTCTTCCAATTTCAAGTGGACGAACAAGCCTCGGATGTTATGACTAAAGAATTCTTCATG

GACTAA

SEQ ID NO 34:
>A. nidulans gi|67537405|ref|XM_657385.1| Aspergillus nidulans FGSC A4
hypothetical protein (AN4873.2), mRNA
ATGCTTTCTAATCCACAAAGTACCCTTCACGGGCGCCATCGTCAACATCGACGGCAGATCTCGACTCCCT

CCGCGCTCGATGCCGTAAAACCCCCAGGCCTTTCTCCACAGGCTCTGCAGAGATATCATGCTCATCGCCG

CGGCCAAAGTCTGGACCAGCGAGCTGTACAAGCTCAAGCTCAGCGACAACAGCTCGTGCAAGATGCGTCA

AGTACTAACCAAACAGCACCGCAATTCGCGCCTAACTCAACCCTCGTCCCCTTAATTCCTGACTCCCAGA

TCTTCGGCCAAGACGACATGCAGGCTTCAAGTCACGCCAATTACCAGACGCCTCACAGCCTACCCTACTT

GCACACGAATTTTGTCAAGGCCGATGATCAGGCTCGGGATGCTCGACCTGTCAATCACCATCTCAATCTC

ATTCAACAGCAGCAGCAACAACTGCACAATGCTAAGCTCAACTGCCACGATACACACGATGATCAGCTGC

TCGACAACGACGCGTGGGATACATACAAACCCGACATCGCGTCCTCGCTTCAACAAACGACCACCGATAT

GAGACGACAATCTGTCCATTCAAACCCAAGTAGCTCATACCATCCGCACACTCCGAAAAAAACAAACTCA

CCAACGACGCCGTTCGACAAAACAGATTTTGCTCAGTACTGCGCGGAGACGCAAATCGTCCCAGCAAAAG

ACCAAAATGCTGCTGATGCCAGCTCCCAGTCGGCCTATATGCAACGCGCCAAGTCCCTTCAAGGAGTAGC

GGGGACTAGCTTCTCACAGCAAAAGATTGAAATGCCCTCTCCCCCTAGCACTGATTCGTTTGCAGTTGAT

GGTTTTGATACGTTTGACTACCAGCAGTGTTCCAGTTTTGATAACCTCGCTACCACCAGCCACAGCCAGT

ACTCTACGTCGTCCAACTCACCAGAAGTCGCTGCCATTCCAAGCTCTGGAGATCACACCGAAAAGAAGTC

CAAGCTCCCTATTTGTCCTGCCACGCCCAGCCGTCTCAGCCCAAGGAAACAGCTCGCTACGCCAAGCGCG

GCTTCTTTAGTGAAGGCAAAACTTTCTCCGCGTGTCGCATCTATCGATAACCTCAACCTGGACTCCCGGG

TGCATGCCTCTATCAAAGAAACTGGTGTTAGCATTGATGAAATAGCGTCCTATATCCACGGTCCAGACCC

CGAAGACGGAAAGTGGGTGTGCCTGCACCCCGGCTGTGAGCGACGCTTTGGCCGCAAGGAAAACATCAAG

TCACATGTGCAAACCCACCTAGGTGATCGCCAGTACAAGTGCGATCATTGTGATAAGTGTTTCGTTCGTG

-continued
```
GGCATGATCTGAAGCGCCACGCGAAGATCCACACAGGAGACAAGCCGTACGAATGTCTATGCGGTAATGT

TTTTGCCCGGCACGATGCCCTAACTCGGCACCGCCAGAGGGGAATGTGCATTGGTGGTTACAAGGGAATT

GTGCGTAAGACAACGAAACGTGGCCGTCCTAAGAAGCACCGCCCAGAGATGGATGAGAGACGTGACAAGG

CAACCAAGACCCGACAGAGGATCGCTGAGAAATCATTATTCAATTCTTCCGAATCGGACACTTCTCGTCG

TACGCCGCCCTCGGAGGTGTTTGAGAACATGAGCCTTCATGGCTCCAGCTCAGCAGACGAGATGGTGACA

TTTGACAGCCAAAATTACTTGCCGCCAGAAGTGTTCACTTTCACTCCGCCCGAATCTCCAAATTACGGTA

CAGCAAGCAAGCCTGCCAGCCCGCGATCTCTCACGCCGAGCTCCGAAGACGAGATGCTACCTTTGTCATC

ATCCAAACGACCACTGGAAAACATTCTTGAGCATTCGGGCCTCCCCCTTCTCACTGATGCCGGCACATGC

TCTTTCTCCTCTGTTTCAAGTTCAAGCAGCCATGCACTATCTTCTCCGCACACCGCGCCTACCCTAAGCG

ACCCTTCGCAACCATCCGATCTCGATATCTTCATCAACAGTGAACCTTCCTCTGCCTTTGGCAAACAAGA

TTTCGGCTTGGGTGATTCGGACATGGCTGCATTCCCAGACTACGTCAACGGCTCTGCGTTTGACAGCAGC

TTGGATTTGCTCCAAGGGAAGAATTTCTCCACAGGGCCCTCTATGGGCGATGACTTCTTTTCCTTCCAGT

TCCAAGTCGACGAACAAGCGTCGGACGTCATGTCAAGGGAGTTTTTCCTCGACTAA
```

SEQ ID NO 35
>gi|169770716|ref|XM-001819776.1| Aspergillus oryzea (AO090003000678)
mRNA, complete cds
```
ATGTTATCGAACCCACATCGCAATCTACAGGAACGACATCGACAACATCGGCGGCAGATTTCAACACCTT

CCGCTCTTGATGCCGCCAAAGTCCCCAGTCTTCCTGCCCAGGCAATGCACCGATACCATGCTCACCGTCG

CGGCCAGAGCCTAGACCAGAGGTCTCTACACATGCAACGATCGCAGACCGTGCAAGATGGTAACCTTCTA

AATACTAACGCAACAGGTCCCCTGGTAATGCAACAGCAACACTATGCTCGTTCGGCGCAACCGACACCCA

TGCCCATGATGCCTGAGTGCCAGACTTTCAGTCCTGAAGAATTGCAAACCCAACCAAGTATGGGATACAT

GAGCCCAGCCTTCGCCAAGGCCGAGACCCCGGCGCTGGAGAGTCGGCCGATGAACCTCCATCTCAATCTG

ATTCAGCAACAGCAGTTGCAGCAAGCACAGCTCATGGAGAATGGCGCTTGGGATTTCTACCCACACGACA

ACCTCCCAACGGGACTTCCGCACCAGACCAACGCAATCCCTGCAGATATGAGACGACTATCAGTGCAGTC

GGATGTCAGTCCCGCGCAAAGACCACATACGCCGAAACCTGCACGTAAGTGCCCTGATATTACTTACAGG

AGACAAGCCCCACTGATGAAACTTAAAGACTACCTTCCCATTACCCCTGCGACAACACCATTCAAGAAAA

CAGTGGATCTTGTGCAGTATGGTGGCGACATGCAGCCAACCCCCACCAAGGAGCAGAGATTGTCTGTTCC

CGTTTCAGCCCAGCCGTCGTACATGCAACGTGCTAAGTCTCTTCAAGGAGTGGCTGGGACGACCTTCTCC

CAGCAAAAGATTGATATGCCCTCTCCCCCAAATACAGCATCCTTCGAGGTGGATAGTTTCGATGTGTTTA

ACTGCCAGCAGGGTTCCAGTTTTGAAATGTCAAAGTCTGAAAGTTTTTCATCTAGCCACTCTTCAACATC

GTCGTCGTCAGCAACATCCCCTTTCAATTCGTCACCAGACCTTGCCTCCATGCCGCACCTTGCAGACAGT

GGTAAGGCGCAGAAGATTCCTATTTACCCTGCAACACCTAGCCGTATGACTCCAAAGAAGACCCCAAGTG

CGCCCCCGAGCTCGGCCAAACCCAAGCTTTCTCCAAGGGTAGCATCTATTGACAGCCTTAATCTTGACGC

CCGGGTCCATGCCTCTATTAAAGAAACTGGTGTCACCATTGACGAGATAGCGTCATACATTCATGGCCCT

GACCCAGAAGATGGAAAATGGGTATGCCTACACCCCGGTTGCGAACGCCGGTTCGGAAGGAAAGAGAACA

TCAAGTCCCATGTCCAAACACATCTTGGAGATCGCCAGTACAAGTGTGATCACTGCGATAAATGCTTCGT

CCGCGGACACGACCTTAAGCGCCACGCCAAGATACATACCGGTGACAAACCATATGAATGCCTCTGTGGT

AATGTGTTCGCCCGACATGATGCCTTGACTCGGCATCGGCAACGCGGCATGTGTATTGCGGCTACAAGG

GTATCGTGCGCAAGACCACCAAACGCGGTCGTCCGAGAAAGCACCGGCCTGAAATGGATGAAAGACAAGA

GAAATCCTCCAGGACGCGCCAGAGAATCGCCGAAAAGTCGTCATTTGACTCTTCTGGATCAGACACTTCG

CACAATTCGCCGCCCTCGGAAGTCTTCGAAAACATGAGCCTGCAGGGTTCTAGTCCGGTGGGAGAAATGC

CAATGTTCAGCAATGTTAATTATTCATTGCCCCCTGAGGTCCTGACTTTCACACCTCCCGCCTCTCCTGG
```

-continued

CGGTAGCATAAGAAACAGACCATCACCTGCCCACAGCCAGCGATCGATTACACCCAGCACTGAGGATGAA

ATGCCACCATTGTCTCCATCTAAACGACCTCTGGAAAGGATCATTGAAGAATCCGGTCTACCTTTAATTT

CGGACCCTGAAGCCTGCCCCTACACAAACGCTACAAACTCAACAACTCATGCCCTATCTTCTCCACACAC

CGTGCCCACTTTGACCGAATCATCAAATGGCTCAGACCTAGACATCTTCATCAACCAAGATCCATCTACA

AGCTTCAGCAAGCACGAGTTCCCTGGCTTAACCGACCCTGACATGGCGGCATTCCCTGATTACGTGAACG

GTCCCGCTTTTGACAACGGCATGGATTTGTTTCAAAGCAAAGGTTTCTCTAACGGTCCCTCAATGAGTGA

CGATTTCTTTGCTTTCCAGTTCCAGATGGACGAACAACCATCGGACGTTATGACAAGGGAATTCTTCTTG

GAGTGA

SEQ ID NO 36: AnigSWI5_1F
CAACACAGGCGGC

SEQ ID NO 37: AnigSWI5_1R
TCTGTTGTTGTTGCATC

SEQ ID NO 38: AterrSWI5_1F
AACATCGAAGGCAGA

SEQ ID NO 39: AterrSWI5_3R
CTGCATCATGTTGAGG

SEQ ID NO 40: AnidSWI5_1F
CGTCAACATCGACG

SEQ ID NO 41: AnidSWI5_1R
TGCTGTTGAATGAGATT

SEQ ID NO 42: Afum_SWI5_1
CCGTCTTTGACCTCAGAAAGA

SEQ ID NO 43: Afum_SWI5_1F
CCCAATTCTCGCAA

SEQ ID NO 44: Afum_SWI5_1R
CCGGATGATTCGCA

SEQ ID NO 45: Aflav_SWI5_1
TGCAACAGCAACACTATGC

SEQ ID NO 46: Aflav_SWI5_1F
AGACCGTGCAAGAT

SEQ ID NO 47: Aflav_SWI5_1R
GGTTTGCAATTCTTCA

SEQ ID NO 48: Anig_SWI5_1
CCTGTGTGTAGCGCAGC

SEQ ID NO 49: Anig_SWI5_1F
ACAGTACCGCAGC

SEQ ID NO 50: Anig_SWI5_1R
CTTCCGGGGTGAA

SEQ ID NO 51: Aterr_SWI5_1
CGATCTCTACATGTTCAACGAC

SEQ ID NO 52: Aterr_SWI5_1F
CGAAAGCTCCCT

SEQ ID NO 53: Aterr_SWI5_1R
CCGTCTGCGGTC

SEQ ID NO 54: Afum_SWI5_2
ATTCCTTGCTGGAGGAGAACA

SEQ ID NO 55: Afum_SWI5_2F
GCACGATGGGACCGT

SEQ ID NO 56: Afum_SWI5_2R
GATTGCGAGAATTGGG

SEQ ID NO 57: Afum_SWI5_3R
CCGATTGCGAGAATTGGG

SEQ ID NO 58: Afum_SWI5_3F
ACGATGGGACCGT

SEQ ID NO 59: Aflav_SWI5_2F
GTCTCTACACATGCAACGATCGC

SEQ ID NO 60: Aflav_SWI5_2R
TGCATTACCAGGGGACCTGTT

SEQ ID NO 61: Aflav_SWI5_2
TGTGCAAGATGGTAACCTTCTAAAT

SEQ ID NO 62: Aterr_SWI5_2F
GACCATGCACGATGGTAACGTT

SEQ ID NO 63: Aterr_SWI5_2R
GTGGGTCCGAAACGTTGCA

SEQ ID NO 64: Aterr_SWI5_2
AGACGGTGATGGGAGAAGT

SEQ ID NO 65: Anig_SWI5_2F
ATCCATGCAAGATGGTAC

SEQ ID NO 66: Anig_SWI5_2R
CTACACACAGGTATCGTT

SEQ ID NO 67: Anig_SWI5_2
TGCTCGGGGACAGCCA

*A. fumigatus* sequence information
SEQ ID NO 68: >Fum505
TTTCAACCCCCAATGCGCTGGAAGCCGCCAAAGTTCCTACCCTTCCAGCACAGGCATTGCAGCGAATCAA

TGCGCATCGCCGTGGACAGAGTCTCGACCAACGACCTTTGCACGATGGGACCGTTTCCATTACTAACGCA

ACAGCAACTCAGCAGCACCAAATCCTTGCTGGAGGAGAACAGCATCCCCAATTCTCGCAATCGGCACATT

TCCCCCAGCACTCCTCTCCCATGCCCGTGATGCCTGAATGCCCGTCTTTGACCTCAGAAGACTTGCAAGC

ATTATCCAATTCTACCAGCAATGCGAATCATCCGGGCATGGCTTACATGAATTCGAGCTTCATTGCTATG

GGAAATCCGAGCTTGGGACTTCGACCAATGGATAACAATCTGAATCTGATGCAACAGCAACAGC

SEQ ID NO 69>Fum359
TTTCAACCCCCAATGCGCTGGAAGCCGCCAAAGTTCCTACCCTTCCAGCACAGGCATTGCAGCGAATCAA

TGCGCATCGCCGTGGACAGAGTCTCGACCAACGACCTTTGCACGATGGGACCGTTTCCATTACTAACGCA

ACAGCAACTCAGCAGCACCAAATCCTTGCTGGAGGAGAACAGCATCCCCAATTCTCGCAATCGGCACATT

TCCCCCAGCACTCCTCTCCCATGCCCGTGATGCCTGAATGCCCGTCTTTGACCTCAGAAGACTTGCAAGC

ATTATCCAATTCTACCAGCAATGCGAATCATCCGGGCATGGCTTACATGAATTCGAGCTTCTTTGCTATG

GGAAATCCGAGCTTGGGACTTCGACCAATGGATAACAATCTGAATCTGATGCAACAGCAACAGC

SEQ ID NO 70>Fum2010
TTTCAACCCCCAATGCGCTGGAAGCCGCCAAAGTTCCTACCCTTCCAGCACAGGCATTGCAGCGAATCAA

TGCGCATCGCCGTGGACAGAGTCTCGACCAACGACCTTTGCACGATGGGACCGTTTCCATTACTAACGCA

ACAGCAACTCAGCAGCACCAAATCCTTGCTGGAGGAGAACAGCATCCCCAATTCTCGCAATCGGCACATT

TCCCCCAGCACTCCTCTCCCATGCCCGTGATGCCTGAATGCCCGTCTTTGACCTCAGAAGACTTGCAAGC

ATTATCCAATTCTACCAGCAATGCGAATCATCCGGGCATGGCTTACATGAATTCGAGCTTCTTTGCTATG

GGAAATCCGAGCTTGGGACTTCGACCAATGGATAACAATCTGAATCTGATGCAACAGCAACAGC

SEQ ID NO 71>FUM4185
TTTCAACCCCCAATGCGCTGGAAGCCGCCAAAGTTCCTACCCTTCCAGCACAGGCATTGCAGCGAATCAA

TGCGCATCGCCGTGGACAGAGTCTCGACCAACGACCTTTGCACGATGGGACCGTTTCCATTACTAACGCA

ACAGCAACTCAGCAGCACCAAATCCTTGCTGGAGGAGAACAGCATCCCCAATTCTCGCAATCGGCACATT

TCCCCCAGCACTCCTCTCCCATGCCCGTGATGCCTGAATGCCCGTCTTTGACCTCAGAAGACTTGCAAGC

```
SEQ ID NO 72 >Fum419
TTTCAACCCCCAATGCGCTGGAAGCCGCCAAAGTTCCTACCCTTCCAGCACAGGCATTGCAGCGAATCAA

TGCGCATCGCCGTGGACAGAGTCTCGACCAACGACCTTTGCACGATGGGACCGTTTCCATTACTAACGCA

ACAGCAACTCAGCAGCACCAAATCCTTGCTGGAGGAGAACAGCATCCCCAATTCTCGCAATCGGCACATT

TCCCCCAGCACTCCTCTCCCATGCCCGTGATGCCTGAATGCCCGTCTTTGACCTCAGAAGACTTGCAAGC

ATTATCCAATTCTACCAGCAATGCGAATCATCCGGGCATGGCTTACATGAATTCGAGCTTCATTGCTATG

GGAAATCCGAGCTTGGGACTTCGACCAATGGATAACAATCTGAATCTGATGCAACAGCAACAGC
```

*A. flavus* sequence information
```
SEQ ID NO 73 >flav2008
TTTCAACACCTTCCGCTCTTGATGCCGCCAAAGTCCCCAGTCTTCCTGCCCAGGCAATGCACCGATACCA

TGCTCACCGTCGCGGCCAGAGCCTAGACCAGAGGTCTCTACACATGCAACGATCGCAGACCGTGCAAGAT

GGTAACCTTCTAAATACTAACGCAACAGGTCCCCTGGTAATGCAACAGCAACACTATGCTCGTTCGGCGC

AACCGACACCCATGCCCATGATGCCTGAGTGCCAGACTTTCAGTCCTGAAGAATTGCAAACCCAACCAAG

TATGGGATACATGAGCCCAGCCTTCGCCAAGGCCGAGACCCCGGCGCTGGAGAGTCGGCCGATGAACCTC

CATCTCAATCTGATGCAACAGCAACAGC

SEQ ID NO 74 >FLAv117.62
TTTCAACACCTTCCGCTCTTGATGCCGCCAAAGTCCCCAGTCTTCCTGCCCAGGCAATGCACCGATACCA

TGCTCACCGTCGCGGCCAGAGCCTAGACCAGAGGTCTCTACACATGCAACGATCGCAGACCGTGCAAGAT

GGTAACCTTCTAAATACTAACGCAACAGGTCCCCTGGTAATGCAACAGCAACACTATGCTCGTTCGGCGC

AACCGACACCCATGCCCATGATGCCTGAGTGCCAGACTTTCAGTCCTGAAGAATTGCAAACCCAACCAAG

TATGGGATACATGAGCCCAGCCTTCGCCAAGGCCGAGACCCCGGCGCTGGAGAGTCGGCCGATGAACCTC

CATCTCAATCTGATGCAACAGCAACAGC

SEQ ID NO 75 >FLAV110.55
TTTCAACACCTTCCGCTCTTGATGCCGCCAAAGTCCCCAGTCTTCCTGCCCAGGCAATGCACCGATACCA

TGCTCACCGTCGCGGCCAGAGCCTAGACCAGAGGTCTCTACACATGCAACGATCGCAGACCGTGCAAGAT

GGTAACCTTCTAAATACTAACGCAACAGGTCCCCTGGTAATGCAACAGCAACACTATGCTCGTTCGGCGC

AACCGACACCCATGCCCATGATGCCTGAGTGCCAGACTTTCAGTCCTGAAGAATTGCAAACCCAACCAAG

TATGGGATACATGAGCCCAGCCTTCGCCAAGGCCGAGACCCCGGCGCTGGAGAGTCGGCCGATGAACCTC

CATCTCAATCTGATGCAACAGCAACAGC
```

*A. niger* sequence information
```
SEQ ID NO 76 >Nig2864
TCGACGCCGTCCGCTCTTGATGCCGTGAAAGCCCCCAGCCTTCCGGCGCAAGCGATGCATCGTTATCATG

CCCATCGTCGAGGACAGAGTTTTGACAACAGAGCTTTGCGCGTCCAGCGATCGCAATCCATGCAAGATGG

TACAAATCATACTACTAACTCTACAGTACCGCAGCAGCACCATTCGAATATGCTCGGGGACAGCCAACAC

CAACGATACCTGTGTGTAGCGCAGCCGTCGTTTCCCCAGCAATCAGCCCCCATGCCCGTGATCCCCGACT

GTTTCACCCCGGAAGAGGTGCAAAACCTTCAAAGTCACAATGGCCAGAACAGTCAACCAAGCATGGCCTA

CCTGAATGCGCCCTTCGCAAAGGACGTTCCGCACATGAACATGCAGTTCGACCTGATGCAACAACAACAG

A

SEQ ID NO 77 >Nig554
TCGACGCCGTCCGCTCTTGATGCCGTGAAAGCCCCCAGCCTTCCGGCGCAAGCGATGCATCGTTATCATG

CCCATCGTCGAGGACAGAGCTTTGACAACAGAGCTTTGCGCGTCCAGCGATCGCAATCCATGCAAGATGG

TACAAATCATACTACTAACTCTACAGTACCGCAGCAGCACCATTCGAATATGCTCGGGGACAGCCAACAC
```

```
CAACGATACCTGTGTGTAGCGCAGCCGTCGTTTCCCCAGCAATCAGCCCCCATGCCCATGATCCCCGACT

GTTTCACCCCGGAAGAGGTGCAAAACCTTCAAAGTCACAATGGCCAGGACAGTCAACCAAGCATGGCCTA

CCTGAATGCGCCCTTCGCAAAGGACGTTCCGCACATGAACATGCAGTTCGATCTGATGCAACAACAACAG

A

SEQ ID NO 78>Nig2828
TCGACGCCGTCCGCTCTTGATGCCGTGAAAGCCCCCAGCCTTCCGGCGCAAGCGATGCATCGTTATCATG

CCCATCGTCGAGGACAGAGTTTTGACAACAGAGCTTTGCGCGTCCAGCGATCGCAATCCATGCAAGATGG

TACAAACCATACTACTAACTCTACAGTACCGCAGCAGCACCATTCGAATATGCTCGGGGACAGCCAACAC

CAACGATACCTGTGTGTAGCGCAGCCGTCGTTTCCCCAGCAATCAGCCCCCATGCCCGTGATCCCCGACT

GTTTCACCCCGGAAGAGGTGCAAAACCTTCAAAGTCACAATGGCCAGGACAGTCAACCAAGCATGGCCTA

CCTGAATGCGCCCTTCGCAAAGGACGTTCCGCACATGAACATGCAGTTCGACCTGATGCAACAACAACAG

A

SEQ ID NO 79>Nig2599
TCGACGCCGTCCGCTCTTGATGCCGTGAAAGCCCCCAGCCTTCCGGCGCAAGCGATGCATCGTTATCATG

CCCATCGTCGAGGACAGAGTTTTGACAACAGAGCTTTGCGCGTCCAGCGATCGCAATCCATGCAAGATGG

TACAAATCATACTACTAACTCTACAGTACCGCAGCAGCACCATTCGAATATGCTCGGGGACAGCCAACAC

CAACGATACCTGTGTGTAGCGCAGCCGTCGTTTCCCCAGCAATCAGCCCCCATGCCCGTGATCCCCGACT

GTTTCACCCCGGAAGAGGTGCAAAACCTTCAAAGTCACAATGGCCAGGACAGTCAACCAAGCATGGCCTA

CCTGAATGCGCCCTTCGCAAAGGACGTTCCGCACATGAACATGCAGTTCGACCTGATGCAACAACAACAG

A

SEQ ID NO 80>Nig121
TCGACGCCGTCCGCTCTTGATGCCGTGAAAGCCCCCAGCCTTCCGGCGCAAGCGATGCATCGTTATCATG

CCCATCGTCGAGGACAGAGTTTTGACAACAGAGCTTTGCGCGTCCAGCGATCGCAATCCATGCAAGATGG

TACAAATCATACTACTAACTCTACAGTACCGCAGCAGCACCATTCGAATATGCTCGGGGACAGCCAACAC

CAACGATACCTGTGTGTAGCGCAGCCGTCGTTTCCCCAGCAATCAGCCCCCATGCCCGTGATCCCCGACT

GTTTCACCCCGGAAGAGGTGCAAAACCTTCAAAGTCACAATGGCCAGGACAGTCAACCAAGCATGGCCTA

CCTGAATGCGCCCTTCGCAAAGGACGTTCCGCACATGAACATGCAGTTCGACCTGATGCAACAACAACAG

A

A. terreus sequence information
SEQ ID NO 81>Terr583
TTTCCACCCCTTCTGCCATTGACGCCGCGAAAGCTCCCTCCCTGCCGGCGCAGGCATTGCATCGATACCA

TGCTCATCGCCGAGGCCAGAGTTTCGACCAACGATCTCTACATGTTCAACGACCGCAGACCATGCACGAT

GGTAACGTTTCAGCTACTAACAACACAGGACCGCAGACGGTGATGGGAGAAGTGCAGCAGCTGCAACGTT

TCGGACCCACAGGACACTCAGGCTATCACCAACACTCGGCTTCTATGCCGGTAATGCCCGAGTGCCAACC

ATTGAGCCAGGAAGACTTCCAGACCCTGGGCAATCGCAATGTCCCAGACAACCAGACCGCCATGACCTAT

ATGACGCCCGCGCTGCACCTCAACATGATGCAG

SEQ ID NO 82>Terr5677
TTTCCACCCCTTCTGCCATTGACGCCGCGAAAGCTCCCTCCCTGCCGGCGCAGGCATTGCATAGATACCA

TGCTCATCGCCGAGGCCAGAGTTTCGACCAACGATCTCTACATGTTCAACGACCGCAGACCATGCACGAT

GGTAACGTTTCAGCTACTAACAACTCAGGACCGCAGACGGTGATGGGAGAAGTGCAGCAGCTGCAACGTT

TCGGACCCACAGGACACTCAGGCTATCACCAACACTCGGCTTCTATGCCGGTAATGCCCGAGTGCCAACC

ATTGAGCCAGGAAGACTTCCAGACCCTGGGCAATCGCAATGTCCCAGACAACCAGACCGCCATGACCTAT

ATGACGCCCGCGCTGCACCTCAACATGATGCAG
```

SEQ ID NO 83>Terr307
TTTCCACCCCTTCTGCCATTGACGCCGCGAAAGCTCCCTCCCTGCCGGCGCAGGCATTGCATCGATACCA

TGCTCATCGCCGAGGCCAGAGTTTCGACCAACGATCTCTACATGTTCAACGACCGCAGACCATGCACGAT

GGTAACGTTTCAGCTACTAACAACACAGGACCGCAGACGGTGATGGGAGAAGTGCAGCAGCTGCAACGTT

TCGGACCCACAGGACACTCAGGCTATCACCAACACTCGGCTTCTATGCCGGTAATGCCCGAGTGCCAACC

ATTGAGCCAGGAAGACTTCCAGACCCTGGGCAATCGCAATGTCCCAGACAACCAGACCGCCATGACCTAT

ATGACGCCCGCGCTGCACCTCAACATGATGCAG

*N. fischeri* sequence information
SEQ ID NO 84>FISCH19912
TCTCCACCCCCAATGCGCTGGAGGCCGCCAAAGTTCCTACCCTTCCAGCACAGGCATTGCAGCGAATCAA

TGCGCATCGCCGTGGGCAGAGTCTTGACCAACGTCCTCGACCTATGCACGATGGGGCCGTTTCCATTACT

AACGCAACAGCAACTCAGCAGTCCCGAATCCTTGCCGGGGGAGCGCATCATCCCCGATTCTCGCAATCGG

CGCATTACCCTCACCATTCCTCTCCCATGCCTGTGATGCCTGAATGCCCGTCTCTGACTTCGGAAGACTT

GGAAGCATTATCCAATTCTACCAGCAACGCGACCCATCCAGGCATGGCTTACATGAATTCGAGCTTCGTT

ACCATGGGAAACCCGAGCTTGGGGAATCGACCAATGGATAACAATCTCAATCTGATGCAACAGCAACAGC

SEQ ID NO 85>2-1085 *N. fischeri*
TCTCCACTCCCAATGCGCTGGAGGCCGCCAAAGTTCCTACACTTCCAGCACAGGCATTGCAGCGAATCAA

TGCGCATCGCCGTGGGCAGAGTCTCGACCAACGTCCTCGACCTATGCACGATGGGGCCGTTTCCATTACT

AACGCAACAGCAACTCAGCAGTCCCGAATCCTTGCCGGGGGAGCGCATCATCCCCGATTCTCGCAATCGG

CGCATTTCCCTCAGCATTCCTCTCCCATGCCTGTGATGCCTGAATGCCCGTCTCTGACCTCGGAAGACTT

GGAAGCACTATCCAATTCTACCAGCAACGCGAACGATCCAGGCATGGCTTACATGAATTCGAGCTTCATT

CCCATGGGAAACCCGAGCTTGGGGAATCGACCAATGGACAGCAATCTCAATCTGATGCAACAGCAACAGC

SEQ ID NO 86>FISCH214525
TCTCAACCCCCAATGCGCTGGAAGCCGCCAAAGTTCCTACCCCTCCAGCACAGGCATTGCAGCGAATCAA

TGCGCATCGCCGTGGACAGAGTCTCGACCAACGACCTTTGCACGTCCGACGTCCTCGACCTATGCACGAT

GGGGCCGTTTCCATTACTAACGCAACAGCAACTCAGCAAACCCAAATCCTTGCCGGGGGAGCGCAACATC

CCCGATTCTCGCAATCGGCGCATTTTCCCCAGCATTCCTCTCCCATGCCTGTAATGCCTGAGTGCCCATC

TTTGACCTCGGAAGACTTGCAAGCATTGTCCAATTCTACCAGCAATGCGAACCATCCGGGCATGGCTTAC

ATGAATTCGAGCTTCATTACCATGGGAAACCCGAGCTTGGGGATCCGACCAATGGACAACAATCTCAATC

TGATGCAACAGCAACAGC

*A. clavatus* sequence information
SEQ ID NO 87>CLAV5138
TCTCAACCCCCAATGTCCTGGAAGCCGTCAAAGTACCTACTCTCCCGGCGCAGGCTTTGCAGCGCATCCA

GGCGCATCGTCGGGACAGAGTCTCGATCAGCGATCTGTGCATGCCCAACGATCTCGTCCCATGCAAGAT

GGTGGTCCTTCCATTACTAACCCAGCAGTGCCTCAGCAACCCCAGATGGTTGCCGGGGGAGCGCCTCATC

AGCAATTCCCTCAATCGTCGCAATTCCCCCAGCAACTTACCCCCATGCCTATGATGCCCGAATGTCAGTC

GTTTCCCTCCGACGAGTTGCAGGCGTTGTCCGGACAGAGCATCAACGTGAATCAACCGGACATGGCTTAT

ATGATTCCAGACTTCGTCAACATCGGAAATCATTGCGTTGGGAACCGACCCATGGTCAGCAACCTCAATC

TGATGCAACAGCAACAGC

SEQ ID NO 88>CLAV1348
TCTCAACCCCCAATGTCCTGGAAGCCGTCAAAGTACCTACTCTCCCGGCGCAGGCTTTGCAGCGCATCCA

GGCGCATCGTCGGGACAGAGTCTCGATCAGCGATCTGTGCATGCCCAACGATCTCGTCCCATGCAAGAT

GGTGGTCCTTCCATTACTAACCCAGCAGTGCCTCAGCAACCCCAGATGGTTGCCGGGGGAGCGCCTCATC

AGCAATTCCCTCAATCGTCGCAATTCCCCCAGCAACTTACCCCCATGCCTATGATGCCCGAATGTCAGTC

-continued

GTTTCCCTCCGACGAGTTGCAGGCGTTGTCCGGACAGAGCATCAACGTGAATCAACCGGACATGGCTTAT

ATGATTCCAGACTTCGTCAACATCGGAAATCATTGCGTTGGGAACCGACCCATGGTCAGCAACCTCAATC

TGATGCAACAGCAACAGC

SEQ ID NO 89>CLAV7944
TCTCAACCCCCAATGTCCTGGAAGCCGTCAAAGTACCTACTCTCCCGGCGCAGGCTTTGCAGCGCATCCA

GGCGCATCGTCGGGGACAGAGTCTCGATCAGCGATCTGTGCATGCCCAACGATCTCGTCCCATGCAAGAT

GGTGGTCCTTCCATTACTAACCCAGCAGTGCCTCAGCAACCCCAGATGGTTGCCGGGGGAGCGCCTCATC

AGCAATTCCCTCAATCGTCGCAATTCCCCCAGCAACTTACCCCCATGCCTATGATGCCCGAATGTCAGTC

GTTTCCCTCCGACGAGTTGCAGGCGTTGTCCGGACAGAGCATCAACGTGAATCAACCGGACATGGCTTAT

ATGATTCCAGACTTCGTCAACATCGGAAATCATTGCGTTGGGAACCGACCCATGGTCAGCAACCTCAATC

TGATGCAACAGCAACAGC

A. nidulans sequence information

SEQ ID NO 90>Nid589
CGACTCCCTCCGCGCTCGATGCCGTAAAACCCCCAGGCCTTTCTCCACAGGCTCTGCAGAGATATCATGC

TCATCGCCGCGGCCAAAGTCTGGACCAGCGAGCTGTACAAGCTCAAGCTCAGCGACAACAGCTCGTGCAA

GATGCGTCAAGTACTAACCAAACAGCACCGCAATTCGCGCCTAACTCAACCCTCGTCCCCTTAATTCCTG

ACTCCCAGATCTTCGGCCAAGACGACATGCAGGCTTCAAGTCACGCCAATTACCAGACGCCTCACAGCCT

ACCCTACTTGCACACGAATTTTGTCAAGGCCGATGATCAGGCTCGGGATGCTCGACCTGTCAATCACCAT

CTCAATCTCATTCAACAGCA

SEQ ID NO 91>Nid7063
CGACTCCCTCCGCGCTCGATGCCGCAAAACCTCCAGGCCTTTCTCCACAGGCTCTGCAGAGATACCATGC

TCATCGCCGCGGCCAAAGTCTGGACCAGCGAGCTGTGCAAGCTCAAGCTCAGCGACAACAGCTCGTGCAA

GATGCGTCAAGTACTAACCAAACAGCACCGCAATTCGCGCCTAACTCAACCCTCGTCCCTTTAATGCCTG

ACTCCCAGATCTTCGGCCAAGACGACATGCAGGCTTCAAGTCACGCCAATTACCAGACGCCTCACAGTCT

ACCCTACTTGCACACGAACTTTGTCAAGGCCGATGATCAGGCTCGGGATGCTCGACCTGTCAATCACCAC

CTCAATCTCATTCAACAGCA

SEQ ID NO 92>Nid808
CGACTCCCTCCGCGCTCGATGCCGTAAAACCCCCAGGCCTTTCTCCACAGGCTCTGCAGAGATATCATGC

TCATCGCCGCGGCCAAAGTCTGGACCAGCGAGCTGTACAAGCTCAAGCTCAGCGACAACAGCTCGTGCAA

GATGCGTCAAGTACTAACCAAACAGCACCGCAATTCGCGCCTAACTCAACCCTCGTCCCCTTAATTCCTG

ACTCCCAGATCTTCGGCCAAGACGACATGCAGGCTTCAAGTCACGCCAATTACCAGACGCCTCACAGCCT

ACCCTACTTGCACACGAATTTTGTCAAGGCCGATGATCAGGCTCGGGATGCTCGACCTGTCAATCACCAT

CTCAATCTCATTCAACAGCA

SEQ ID NO 93>Nid670
CGACTCCCTCCGCGCTCGATGCCGCAAAACCTCCAGGCCTTTCTCCACAGGCTCTGCAGAGATACCATGC

TCATCGCCGCGGCCAAAGTCTGGACCAGCGAGCTGTGCAAGCTCAAGCTCAGCGACAACAGCTCGTGCAA

GATGCGTCAAGTACTAACCAAACAGCACCCCAATTCGCGCCTAACTCAACCCTCGTCCCTTTAATGCCTG

ACTCCCAGATCTTCGGCCAAGACGACATGCAGGCTTCAAGTCACGCCAATTACCAGACGCCTCACAGTCT

ACCCTACTTGCACACGAACTTTGTCAAGGCCGATGATCAGGCTCGGGATGCTCGACCTGTCAATCACCAC

CTCAATCTCATTCAACAGCA

A. glaucus sequence information
SEQ ID NO 94>GLAU117314
TCTCGCAACCCTACAGCCCTCGAGGCCGCGAAAGTTCCCAGTCTCCCTGCACCGGCATTGCAACGGCTCA

ATGCTCATCGACGAGGCCAGAGCCTCGACACACGGGCCTTCCAGATGCAACAACGAGCACAGGCCATGCA

```
GGATGGGAATCTTTCTTTTACTAACCAAGGAACAGTACACCAACAACCACAACCACACAATGTCTTGCGC

GAGGCCCAACAACAGCGATTGGCTAGACAGGGACATCAGATGTATCCCGCTAATTCAACATCTGTACCCC

TGATGCCCGACTGCCACGCGTTCAGCCAAGGGGACCTGCATATGCCTGCGAACCAAGACAACAATGAGAA

CCACCAAAGCGCGGCGTATATTGAAGCACAGCTGAATCTGAACTTCAATCTGATGCAACAGCAACAGC

SEQ ID NO 95>GLAU543
TCTCGCAACCCTACAGCCCTCGAGGCCGCGAAAGTTCCCAGTATCCCTGCACCGGCATTGCAACGGCTCA

ATGCTCATCGACGAGGCCAGAGCCTCGACACACGGGCCTTCCAGATGCAACAACGAGCACAGGCCATGCA

GGATGGGAATCTTTCTTTTACTAACCAAGGAACAGTACACCAACAACCACAACCACACAATGTCTTGCGC

GAGGTCCAACAACAGCGATTGGCTAGACAGGGACATCAGATGTATCCCGCTAATTCAACATCTGTACCCC

TGATGCCCGACTGCCACGCGTTCAGCCAAGGGGACCTGCATATGCCTGCGAACCAAGACAACAATGAGAA

CCACCAAAGCGCGGCGTATATTGAAGCACAGCTGAATCTGAACTTCAATCTGATGCAACAGCAACAGC
```

REFERENCES

Aerne B L, Johnson A L, Toyn J H, Johnston L H.
 Swi5 controls a novel wave of cyclin synthesis in late mitosis. Mol Biol Cell. 1998 April; 9(4):945-56.

Akamatsu Y, Dziadkowiec D, Ikeguchi M, Shinagawa H, Iwasaki H.
 Two different Swi5-containing protein complexes are involved in mating-type switching and recombination repair in fission yeast. Proc Natl Acad Sci USA. 2003 Dec. 23; 100(26):15770-5. Epub 2003 Dec. 8.

Butler G, Thiele D J.
 ACE2, an activator of yeast metallothionein expression which is homologous to SWI5. Mol Cell Biol. 1991 January; 11(1):476-85.

MacCallum D M, Findon H, Kenny C C, Butler G, Haynes K, Odds F C.
 Different consequences of ACE2 and SWI5 gene disruptions for virulence of pathogenic and nonpathogenic yeasts. Infect Immun. 2006 September; 74(9):5244-8.

Ellermeier C, Schmidt H, Smith G R.
 Swi5 acts in meiotic DNA joint molecule formation in *Schizosaccharomyces pombe*. Genetics. 2004 December; 168(4):1891-8. Epub 2004 Sep. 30.

The invention claimed is:

1. A diagnostic kit for a fungal or yeast species comprising an deoxyoligonucleotide probe comprising SEQ ID NO: 54, or a probe having a sequence at least 95% sequence identity thereto, and wherein the probe is from about 21 to about 100 nucleotides and capable of binding to at least a portion of the *Aspergillus* spp. SWI5 gene ("SWI5 gene") or its corresponding mRNA and wherein the detectable moiety comprises a radioisotope, a fluorescent moiety, chemiluminescent label, a nanoparticle, an enzyme or a ligand.

2. The kit of claim 1 wherein the portion of the SWI5 gene is a portion of the region of the gene from base pair position 1 to base pair position 2319 of SEQ ID NO: 29 of the *Aspergillus* SWI5 gene.

3. The kit of claim 1 wherein the portion of the SWI5 gene is a portion of the region of the gene from base pair position 38 to base pair position 472 of SEQ ID NO: 29 of, or from base pair position 1423 to base pair position 1627 of SEQ ID NO: 29 of the *Aspergillus* SWI5 gene.

4. The kit of claim 1 comprising a probe for a portion of the region of the gene from base pair position 1 to base pair position 2319 of SEQ ID NO: 29 of, from base pair position 38 to base pair position 472 of SEQ ID NO: 29, and from base pair position 1423 to base pair position 1627 of SEQ ID NO: 29 of the *Aspergillus* SWI5 gene.

5. The kit of claim 1 further comprising a probe comprising an oligonucleotide having a sequence selected from SEQ ID NO 17, 18, 42, 45, 48, 51, 61, 64, or 67 or sequences having at least 90% sequence identity thereto and which and wherein the probe is from about 10 to about 100 nucleotides and capable of binding to at least a portion of the *Aspergillus* spp. SWI5 gene ("SWI5 gene") or its corresponding mRNA.

6. The kit of claim 1 further comprising a primer for amplification of at least a portion of the SWI5 gene.

7. The kit of claim 1 comprising a forward and a reverse primer for a portion of the SWI5 gene.

8. The kit of claim 1 further comprising at least one forward in vitro amplification primer and at least one reverse in vitro amplification primer, the forward amplification primer being selected from the group consisting of SEQ ID NO 1, 3, 5, 7, 9, 11, 13, 15, 36, 38, 40, 43, 46, 49, 52, 55, 58, 59, 62 or 65, or sequences having at least 90% sequence identity thereto and which can also act as a forward amplification primer and the reverse amplification primer being selected from the group consisting of SEQ ID NO 2, 4, 6, 8, 10, 12, 14, 16, 37, 39, 41, 44, 47, 50, 53, 56, 57, 60, 63 or 66, sequences having at least 90% sequence identity thereto and which can also act as a reverse amplification primer.

9. A diagnostic kit as claimed in claim 8, based on direct nucleic acid detection technologies, signal amplification nucleic acid detection technologies, and nucleic acid in vitro amplification technologies is selected from one or more of Polymerase Chain Reaction (PCR), Ligase Chain Reaction (LCR), Nucleic Acids Sequence Based Amplification (NASBA), Strand Displacement Amplification (SDA), Transcription Mediated Amplification (TMA), Branched DNA technology (bDNA) and Rolling Circle Amplification Technology (RCAT) or other enzymatic in vitro amplification based technologies.

10. The kit of claim 1, further comprising at least one reverse in vitro amplification primer of SEQ ID NO 55, or sequences having at least 90% sequence identity thereto and which can also act as a forward amplification primer and a reverse amplification primer of SEQ ID NO 56, or sequences having at least 90% sequence identity thereto and which can also act as a reverse amplification primer.

11. The kit of claim 1, wherein the probe consists of SEQ ID NO 54 and further comprising primers consisting of SEQ ID NOs 55 and 56, or sequences having at least 90% sequence identity thereto.

12. A diagnostic kit for a fungal or yeast species comprising an deoxyoligonucleotide probe comprising SEQ ID NO: 54; wherein the probe is from about 21 to about 100 nucleotides and capable of binding to at least a portion of the *Aspergillus* spp. SWI5 gene ("SWI5 gene") or its corresponding mRNA and wherein the probe is attached to a detectable moiety to detect or confirm probe hybridization to the portion of the SWI5 gene or its corresponding mRNA.

13. A diagnostic kit of claim 12, further comprising SEQ ID NO: 17, 48, 51, 61, 64, or 67.

* * * * *

SEQUENCE LISTING

```
<160> NUMBER OF SEQ ID NOS: 95

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
atcgacaaca tcgtcggcag a                                                 21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gctgttgctg ttgcatcaga tt                                                22

<210> SEQ ID NO 3
<211> LENGTH: 17
<212> TYPE: DNA
<213> ORGANISM: Artificial Sequence
<220> FEATURE:
<223> OTHER INFORMATION: Primer

<400> SEQUENCE: 3
tagccgccat gccaagc                                                      17

<210> SEQ ID NO 4
```

```
<211> LENGTH: 21
<212> TYPE: DNA
<213> ORGANISM: Artificial Sequence
<220> FEATURE:
<223> OTHER INFORMATION: Primer

<400> SEQUENCE: 4
ccagtctctt tgatagaagc a                                              21

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
cgtggacatg acctgaagc                                                 19

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
gtctctcctc caactctgg                                                 19

<210> SEQ ID NO 7
<211> LENGTH: 16
<212> TYPE: DNA
<213> ORGANISM: Artificial Sequence
<220> FEATURE:
<223> OTHER INFORMATION: Primer

<400> SEQUENCE: 7
atgttagcca atccac                                                    16

<210> SEQ ID NO 8
<211> LENGTH: 13
<212> TYPE: DNA
<213> ORGANISM: Artificial Sequence
<220> FEATURE:
<223> OTHER INFORMATION: Primer

<400> SEQUENCE: 8
attccaggca ccg                                                       13

<210> SEQ ID NO 9
<211> LENGTH: 15
<212> TYPE: DNA
<213> ORGANISM: Artificial Sequence
<220> FEATURE:
<223> OTHER INFORMATION: Primer

<400> SEQUENCE: 9
cttgagggcc aaatc                                                     15

<210> SEQ ID NO 10
<211> LENGTH: 16
<212> TYPE: DNA
<213> ORGANISM: Artificial Sequence
<220> FEATURE:
<223> OTHER INFORMATION: Primer

<400> SEQUENCE: 10
```
ctcgtccttt caatcc                                                    16

<210> SEQ ID NO 11
<211> LENGTH: 14
<212> TYPE: DNA
<213> ORGANISM: Artificial Sequence
<220> FEATURE:
<223> OTHER INFORMATION: Primer

<400> SEQUENCE: 11
actatgcctc gtcg                                                      14

<210> SEQ ID NO 12
<211> LENGTH: 15
<212> TYPE: DNA
<213> ORGANISM: Artificial Sequence
<220> FEATURE:
<223> OTHER INFORMATION: Primer

<400> SEQUENCE: 12
agcgaataca ttgcc                                                     15

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
acaaaccata tgaatgtc                                                  18

<210> SEQ ID NO 14
<211> LENGTH: 12
<212> TYPE: DNA
<213> ORGANISM: Artificial Sequence
<220> FEATURE:
<223> OTHER INFORMATION: Primer

<400> SEQUENCE: 14
gcaggctcgg tt                                                        12

<210> SEQ ID NO 15
<211> LENGTH: 15
<212> TYPE: DNA
<213> ORGANISM: Artificial Sequence
<220> FEATURE:
<223> OTHER INFORMATION: Primer

<400> SEQUENCE: 15
cctcgagaag atcgt                                                     15

<210> SEQ ID NO 16
<211> LENGTH: 16
<212> TYPE: DNA
<213> ORGANISM: Artificial Sequence
<220> FEATURE:
<223> OTHER INFORMATION: Primer

<400> SEQUENCE: 16
ctagcagtcc atgaag                                                    16

<210> SEQ ID NO 17
<211> LENGTH: 24
<212> TYPE: DNA

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ccaaagttcc taccctccca gcac					24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
ctgactcggc acagacaacg agga					24

<210> SEQ ID NO 19
<211> LENGTH: 414
<212> TYPE: DNA
<213> ORGANISM: Aspergillus fumigatus

<400> SEQUENCE: 19
tttcaacccc caatgcgctg gaagccgcca agttcctac ccttccagca caggcattgc     60
agcgaatcaa tgcgcatcgc cgtggacaga gtctcgacca cgacctttg cacgatggga    120
ccgtttccat tactaacgca acagcaactc agcagcacca atccttgct ggaggagaac    180
agcatcccca attctcgcaa tcggcacatt tcccccagca ctcctctccc atgcccgtga    240
tgcctgaatg cccgtctttg acctcagaag acttgcaagc attatccaat tctaccagca    300
atgcgaatca tccgggcatg gcttacatga attcgagctt cattgctatg gaaatccga    360
gcttgggact cgaccaatg gataacaatc tgaatctgat gcaacagcaa cagc           414

<210> SEQ ID NO 20
<211> LENGTH: 420
<212> TYPE: DNA
<213> ORGANISM: Neosartorya fischeri

<400> SEQUENCE: 20
tctccactcc caatgcgctg gaggccgcca agttcctac acttccagca caggcattgc     60
agcgaatcaa tgcgcatcgc cgtgggcaga gtctcgacca cgtcctcga cctatgcacg    120
atggggccgt ttccattact aacgcaacag caactcagca gtcccgaatc cttgccgggg    180
gagcgcatca tccccgattc tcgcaatcgg cgcatttccc tcagcattcc tctcccatgc    240
ctgtgatgcc tgaatgcccg tctctgacct cggaagactt ggaagcacta tccaattcta    300
ccagcaacgc gaacgatcca ggcatggctt acatgaattc gagcttcatt cccatgggaa    360
acccgagctt ggggaatcga ccaatggaca gcaatctcaa tctgatgcaa cagcaacagc    420

<210> SEQ ID NO 21
<211> LENGTH: 378
<212> TYPE: DNA
<213> ORGANISM: Aspergillus nidulans

<400> SEQUENCE: 21
tctcgactcc ctccgcgctc gatgccgcaa aacctccagg cctttctcca caggctctgc     60
agagatacca tgctcatcgc cgcggccaaa gtctggacca gcgagctgtg caagctcaag    120
ctcagcgaca cagctcgtg caagatgcgt caagtactaa ccaaacagca ccccaattcg    180
cgcctaactc aaccctcgtc cctttaatgc ctgactccca gatcttcggc caagacgaca    240

```
tgcaggcttc aagtcacgcc aattaccaga cgcctcacag tctaccctac ttgcacacga    300
actttgtcaa ggccgatgat caggctcggg atgctcgacc tgtcaatcac cacctcaatc    360
tgatgcaaca gcaacagc                                                  378
```

<210> SEQ ID NO 22
<211> LENGTH: 438
<212> TYPE: DNA
<213> ORGANISM: Aspergillus clavatus

<400> SEQUENCE: 22

```
tctcaacccc caatgtcctg gaagccgtca aagtacctac tctcccggcg caggctttgc     60
agcgcatcca ggcgcatcgt cggggacaga gtctcgatca gcgatctgtg catgcccaac    120
gatctcgtcc catgcaagat ggtggtcctt ccattactaa cccagcagtg cctcagcaac    180
cccagatggt tgccggggga gcgcctcatc agcaattccc tcaatcgtcg caattccccc    240
agcaacttac ccccatgcct atgatgcccg aatgtcagtc gtttccctcc gacgagttgc    300
aggcgttgtc cggacagagc atcaacgtga atcaaccgga catggcttat atgattccag    360
acttcgtcaa catcggaaat cattgcgttg ggaaccgacc catggtcagc aacctcaatc    420
tgatgcaaca gcaacagc                                                  438
```

<210> SEQ ID NO 23
<211> LENGTH: 423
<212> TYPE: DNA
<213> ORGANISM: Aspergillus niger

<400> SEQUENCE: 23

```
tctcgacgcc gtccgctctt gatgccgtga agcccccag ccttccggcg caagcgatgc      60
atcgttatca tgcccatcgt cgaggacaga gctttgacaa cagagctttg cgcgtccagc    120
gatcgcaatc catgcaagat ggtacaaatc atactactaa ctctacagta ccgcagcagc    180
accattcgaa tatgctcggg gacagccaac accaacgata cctgtgtgta gcgcagccgt    240
cgtttcccca gcaatcagcc ccatgcccca tgatccccga ctgtttcacc ccggaagagg    300
tgcaaaacct tcaaagtcac aatggccagg acagtcaacc aagcatggcc tacctgaatg    360
cgcccttcgc aaaggacgtt ccgcacatga acatgcagtt caatctgatg caacagcaac    420
agc                                                                  423
```

<210> SEQ ID NO 24
<211> LENGTH: 378
<212> TYPE: DNA
<213> ORGANISM: Aspergillus flavus

<400> SEQUENCE: 24

```
tttcaacacc ttccgctctt gatgccgcca agtccccag tcttcctgcc caggcaatgc      60
accgatacca tgctcaccgt cgcggccaga gcctagacca gaggtctcta cacatgcaac    120
gatcgcagac cgtgcaagat ggtaaccttc taaatactaa cgcaacaggt ccctggtaa    180 tgcaacagca acactatgct cgttcggcgc aaccgacacc catgcccatg atgcctgagt    240
gccagacttt cagtcctgaa gaattgcaaa ccccaaccaag tatgggatac atgagcccag    300
ccttcgccaa ggccgagacc ccggcgctgg agagtcggcc gatgaacctc catctcaatc    360
tgatgcaaca gcaacagc                                                  378
```

<210> SEQ ID NO 25

```
<211> LENGTH: 186
<212> TYPE: DNA
<213> ORGANISM: Aspergillus fumigatus

<400> SEQUENCE: 25
gtcacgccaa gattcacact ggagacaaac catatgaatg tctttgtggc aatgtattcg      60
ctaggcacga tgctctgact cggcacagac aacgaggaat gtgcatcggc ggttacaagg     120
gtattgtgcg caagacaacc aagcgtggcc gtccaaagaa acatcgacca gagttggagg     180
agagac                                                                186

<210> SEQ ID NO 26
<211> LENGTH: 186
<212> TYPE: DNA
<213> ORGANISM: Neosartorya fischeri

<400> SEQUENCE: 26
gtcacgccaa gattcacact ggagacaagc catatgaatg tctctgtggc aacgtattcg      60
ctaggcacga tgctctgact cggcacaggc aacgaggaat gtgcatcggc ggttacaagg     120
gtattgtgcg caagacaaca aaacgtggtc gtccgaagaa acatcgacca gagttggagg     180
agagac                                                                186

<210> SEQ ID NO 27
<211> LENGTH: 186
<212> TYPE: DNA
<213> ORGANISM: Aspergillus nidulans

<400> SEQUENCE: 27
gccacgcgaa gatccacaca ggagacaagc cgtacgaatg tctatgcggt aatgttttg       60 cccggcacga tgccctaact cgacaccgcc agagggaat gtgcattggt ggttacaagg      120
gaattgtgcg taagacaacg aaacgtggcc gtcctaagaa gcaccgccca tagttggagg     180
agagac                                                                186

<210> SEQ ID NO 28
<211> LENGTH: 186
<212> TYPE: DNA
<213> ORGANISM: Aspergillus niger

<400> SEQUENCE: 28
gtcatgctaa gatccatacc ggcgacaagc cttacgagtg cctctgtgga aatgtatttg      60
cgagacacga cgccttgact cgacacagac agcggggtat gtgcattggc ggctacaagg     120
gaattgtgcg caagacaacg aaacggggtc gtccgaagaa gcaccgacca gagttggagg     180
agagac                                                                186

<210> SEQ ID NO 29
<211> LENGTH: 2319
<212> TYPE: DNA
<213> ORGANISM: Aspergillus fumigatus

<400> SEQUENCE: 29
atgttagcca atccacatag taatctgcac gagcgttatc gacaacatcg tcggcagatt      60
tcaaccccca atgcgctgga agccgccaaa gttcctaccc ttccagcaca ggcattgcag     120
cgaatcaatg cgcatcgccg tggacagagt ctcgaccaac gacctttgca cgatgggacc     180
gtttccatta ctaacgcaac agcaactcag cagcaccaaa tccttgctgg aggagaacag     240
catccccaat tctcgcaatc ggcacatttc ccccagcact cctctcccat gcccgtgatg     300
```

```
cctgaatgcc cgtctttgac ctcagaagac ttgcaagcat tatccaattc taccagcaat    360
gcgaatcatc cgggcatggc ttacatgaat tcgagcttct tgctatggg gaatccgagc     420
ttgggacttc gaccaatgga taacaatctg aatctgatgc aacagcaaca gcagcaaaat    480
gcccacgtct catgcgtcaa tagccttgag ggccaaatcc tcgacaacgg tgcctggaat    540
ttctaccagc aaggccagct ccctacgacg cttcggtctc aagtcaacaa tctttcggcc    600
gatgggagac gacagtctgt tcagtcagat atcaccccct cgcaacgacc acatacccc    660
aagcaagcaa atacgcacta ctttcccata cgccagcga caactccgtt taagaaaccg    720
gcggaacttg ctcagtatag tacgacatg cagtccaccc ccaccaagga gacaggccgc    780
tctgcacccg catcagccca gtcggtatac atgcaacgag ccaaatccct ccaaggagtt    840
gcggggtcta ccttttccaa ctccaaaatc gagatgccct cccccccgaa cacggcttca    900
tttgaaattg acaattttga tgcgtttagc agtcagcagg gttccagttt cgagatttcc    960
gagtcagaga atttatcgca gagtcactat gcctcgtcgt cagcaacctc gtcctttcaa   1020
tcctccccag agctagccgc catgccaagc cccgaagaca atcacgagaa ggctcataag   1080
ctgcccatct tccctgccgc gtccaatcgg ccagcgcaca ggaaggcgct gagtaccagc   1140
tccagttcca ccttgacgaa accccggctc tctccaagag tggcttcaat tgatagcctt   1200
aaccttgatg ctagggttca tgcttctatc aaagagactg ggatcaccat cgatgagatc   1260
gcctcctaca tctctggccc tgaccccgag gatggaaagt gggtttgcct tcaccccggc   1320
tgcgagcggc ggttcggaag aaaagaaaat atcaagtccc acgtccaaac ccaccttggt   1380
gatcgccaat ataagtgtga tcattgcaac aagtgcttcg ttcgtggaca tgacctgaag   1440
cgtcacgcca agattcacac tggagacaaa ccatatgaat gtctttgtgg caatgtattc   1500
gctaggcacg atgctctgac tcggcacaga caacgaggaa tgtgcatcgg cggttacaag   1560
ggtattgtgc gcaagacaac caagcgtggc cgtccaaaga acatcgacc agagttggag   1620
gagagacagg ataaggcagc caagacacgc cagagagtcg ccgaaaagtc atcccatgac   1680
tcctcgtccg ggtgtgttga ttcccccaac tcgccgcctt ccgaaatcct tgaaaatatg   1740
agtcttcacg ggggatcgag ccctaaagag aatatgcccg cgttcattca gcccaacttt   1800
tccttgcctc catcggcgtt tactttcacg cctcctgcgt ctccccgaca gagtcttgga   1860
aaccagccat cgcccgctca gagtcgccgc tcactcacgc ccagtagcga ggatgaaatg   1920
ctgcctttgt ctccctccaa gcgcccctc gagaagatcg ttgaagaacc gagcctgcct   1980
ttcacttcga gtgccgaccc atacaccgat attgctgcct ccaccgcgga gctgtcttct   2040
ccacatacgg ctcccacctt ggctgattcg tctcacggct ccgacctcga tattttcatc   2100
agcacggata gctccgccaa tttcaagcat gaatttcccg atctgagtga ccccgacatg   2160
gccgctttcc ccgactatgt caatgggtct accttcgaac ccggaatgga tctgttctcg   2220
agcaagacat tctctgccgg tacctcgatg aacgaggact tcttttcact ccaattccag   2280
gttgatgata tgaccaaaga attcttcatg gactgctag                           2319
```

<210> SEQ ID NO 30
<211> LENGTH: 2403
<212> TYPE: DNA
<213> ORGANISM: Neosartorya fischeri

<400> SEQUENCE: 30

```
atgttagcca atccacatag caatctgcac gagcgttatc gacaacatcg tcggcagatc     60
```

```
tcaaccccca atgcgctgga agccgccaaa gttcctaccc ttccagcaca ggcattgcag    120
cgaatcaatg cgcatcgccg tggacagagt ctcgaccaac gacctttgca cgtccaacgt    180
cctcgaccta tgcacgatgg ggccgtttcc attactaacg caacagcaac tcagcagcac    240
caaatccttg ccggggagc gcagcatccc cgattctcgc aatcggcgca tttcccccag     300
cactcctctc ccatgcccgt gatgcctgaa tgcccgtctt tgacctcgga agacttgcaa    360
gcattatcca attctaccag caatgcgaac catccgggca tggcttacat gaattcgagc    420
ttcattacca tgggaaatcc gagcttgggg attcgaccaa tggataacaa tctaaatctg    480
atgcaacagc agcagctgca aaatgctcac gtctcatgcg tcaatagcct tgatggccaa    540
atcctcgaca acggtgcctg gaatttctac cagcaaggcc agctccctac gacgcttcgg    600
tctcaagtca caaccttc gaccgatggg agacgacagt ctgttcagtc agatatcacc      660
ccctcgcaac gaccgcatac ccccaagcag gcaaatacgc gtaagttatc cgttcagtca    720
tactggtcat ttttctccca gccactaacg accgatccag actactttcc cataacgcca    780
gcgacaactc cgttcaagaa accagcggaa cttgctcagt atagtacgga catgcagtcc    840 acccctcca aggagacagg ccgctctgca cccgcatcag cccagtcggc atacatgcaa      900
cgagccaaat ccctccaagg agttgccggg tctacctttt ccaactccaa aatcgagatg    960 ccctccccc cgaacactgc ttcatttgaa attgacaatt tgatgcgtt tagcagtcag     1020 cagggttcca gtttcgaaat ttccgagtca gagaatttat cgcagagtca ctatgcctcg   1080
tcgtcagcaa cctcgtcctt tcaatcctcc ccagagctag ccgccatgcc aagcccagaa    1140
gacaatcatg agaaggctca taaactgccc atcttccctg ccgcgtcgag tcgggcaacc    1200
cacaggaagg cgctgagtac cagctccagt tcctccttga cgaaacccg gctctctcca     1260 agagtggctt caattgatag ccttaacctt gatgctaggg ttcatgcttc tatcaaagag    1320
actgggatca ccatcgatga gatagcctcc tacatctctg gccccgaccc ggaggatgga    1380
aagtgggttt gccttcaccc cggctgcgaa cggcggttcg gaagaaaaga gaatattaag    1440
tcacacgtcc aaacccacct tggtgatcgc caatataaat gtgatcattg caacaagtgc    1500
ttcgttcgtg gacatgacct gaagcgtcac gccaagattc acactggaga caaaccatat    1560
gaatgtcttt gtggcaacgt attcgctagg cacgatgctc tgactcggca cagacaacga    1620
ggaatgtgca tcggcggtta caagggtatt gtgcgcaaga caacaaaacg tggtcgtcca    1680
aagaaacatc gaccagagtt ggaggagaga caggacaagg cagccaagac acgccagaga    1740
gtcgccggga agtcatccct tgactcctcg tccgggtgtg ttgataccc caactcgccg      1800 ccttccgaaa tccttgagaa tatgagtctt cacggtggat cgagcccaa agaggatatg      1860 cccgtgttca tccaacccaa cttttccttg cctccatcgg cgtttacttt cacgcctcct    1920
gcgtctccgc gacagagtct tggaaaccag ccatcgcccg ctcagagtcg ccgctcactc    1980
acacccagta gcgaggatga aatgctgcct ttgtcgccct ccaagcgccc cctcgagaag    2040
attgttgaag aaccgagcct gccttcatt tcgaatgccg acccatatac cgatattgct     2100
acctccaccg ccgagctgtc ttctccacat acggctccca ccttggctga ttcgtctcac    2160
ggctccgacc tcgatatctt catcagcacg gacagctccg ccaacttcaa gcatgaattt    2220
cccgatctga gtgaccccga catggccgct ttccccgact atgtcaatgg gtctactttc    2280
gagcccggac tggatctgtt ctcgagcaag acattctctg ccggtacctc gatgaacgag    2340
gacttctttt cactccaatt ccaggttgat gatatgacca aagaattctt catggactgc    2400
tag                                                                    2403
```

<210> SEQ ID NO 31
<211> LENGTH: 2391
<212> TYPE: DNA
<213> ORGANISM: Aspergillus clavatus

<400> SEQUENCE: 31

| | | | | | |
|---|---|---|---|---|---|
| atgtttgcca | atccgcacag | taaccttcac | gagcggtatc | gacaacatcg | ccggcagatc | 60 |
| tcaaccccca | atgtcctgga | agccgtcaaa | gtacctactc | tcccggcgca | ggctttgcag | 120 |
| cgcatccagg | cgcatcgtcg | gggacagagt | ctcgatcagc | gatctgtgca | tgcccaacga | 180 |
| tctcgtccca | tgcaagatgg | tggtccttcc | attactaacc | cagcagtgcc | tcagcaaccc | 240 |
| cagatggttg | ccgggggagc | gcctcatcag | caattccctc | aatcgtcgca | attccccccag | 300 |
| caacttaccc | ccatgcctat | gatgcccgaa | tgtcagtcgt | ttccctccga | cgagttgcag | 360 |
| gcgttgtccg | gacagagcat | caacgtgaat | caaccggaca | tggcttatat | gattccagac | 420 |
| ttcgtcaaca | tcgaaaatca | ttgcgttggg | aaccgaccca | tggtcagcaa | cctcaatctg | 480 |
| attcaacagc | agcaactgca | caatccccat | atcattgcaa | acagtgcgct | cgatggccag | 540 |
| attctcgaca | cagcgctttt | caatatctat | cagcatggcc | ttcgacccca | gacaaacaat | 600 |
| cttttcagtgg | atacacgacg | attgtcagtt | cactcggatg | taagcccctc | gcatcagcca | 660 |
| catacgccca | gcagacgaaa | ttcgcgtaag | tccactgtct | ctccatggcg | aatcctgagt | 720 |
| ccatcaactc | ccgactcacg | actggaatca | gaatatttcc | cgattacccc | agcaacaact | 780 |
| cctttcaaga | aaacagccga | acttgctcag | tatagcacgg | acgtccagac | aactccctcc | 840 |
| aaggagcaac | gcttttcggc | cgctcaggcg | gcctacatgc | agcgggccaa | gtcccttcag | 900 |
| ggcgtggccg | gaactacctt | ttctcaacca | aagatcgaga | tgctttcccc | ccataacaca | 960 |
| ggttcgtttg | aaattgagag | ttttaatact | tttggcagtc | agcagggttc | cacttttgaa | 1020 |
| ttttccgagt | cagagaattt | gtcgcaaggc | cagtatgcct | cgtcgtcagc | aacgtcatcc | 1080 |
| ttccaatcct | ccccagagct | agcggccatg | ccaagccccg | aggaccataa | cgaaaaggcg | 1140 |
| cacaagatcc | ccatcttccc | agccgtatcc | agccgtatca | gtcacaagaa | gactttgagt | 1200 |
| cttcccgcta | gcacttcgcc | ggcgaaaccc | aagcttctc | ccagagtggc | gtccatagac | 1260 |
| aacctgaacc | tcgatgcccg | tgtgcacgcc | tcaatcaaag | agaccggtgt | caccattgac | 1320 |
| gagattgctt | cctacatctc | cggcccggat | ccagaggatg | aaagtgggt | ttgcattcac | 1380 |
| cctggttgcg | agcggcggtt | tggaagaaaa | gaaaacatca | agtcacacgt | ccaaacacat | 1440 |
| ctgggagatc | gccagtataa | atgtgaccat | tgcaacaagt | gtttcgtccg | cggacatgac | 1500 |
| ctgaagcgtc | atgctaagat | ccacactgga | gacaaaccgt | acgaatgcct | tgcgggaac | 1560 |
| gttttcgcta | gacacgatgc | tttgacccgc | caccgacagc | gaggcatgtg | catcggtggt | 1620 |
| tacaagggaa | ttgtgcgcaa | gacaacaaaa | cgcggtcgtc | ctaagaaaca | ccggccggag | 1680 |
| atggatgaaa | ggcaggacaa | agccgccaaa | acacgccagc | gagtcgctga | taagacatcc | 1740 |
| tttgactcct | tgtctgggac | agatgttgcg | ccgaattcac | caccatccga | agttcttgag | 1800 |
| aacatgagcc | tacacgggga | tccaagccca | aagaagaga | tgcccgcgtt | caaccagccc | 1860 |
| gattactcgt | taccaccctc | tgttttcacc | ttcacgcctc | ctgcatcgcc | agggcacaac | 1920 |
| cttggaaacc | ggccatcacc | gaatcagagt | taccggtctc | tcacgcccag | tagtgaagat | 1980 |
| gaaatgctgc | cttcgtcgcc | tatcaagcgg | cctctagaga | ggatcgccga | agagtcgggg | 2040 |
| ttgccttata | tcgaacatgc | agatctctat | actgagatcg | ccacttctgc | tgctgatctg | 2100 |

-continued

```
tcgtctccac acaccgctcc taccttggcc gattcatgtc acggctctga tctcgatatc    2160
ttcatcagcc ctgacagctc tgcgaacttc aaacatgaat tccctgagct gagtgacatg    2220
gccgctttcc ctgactatac gaatacctct accttcgacg ccggactgga cctcttctca    2280
agcaagaact tctccactgt tccttcaatg aatgacgatt tcttctcctt ccaattccag    2340
gctgacgacc aaccccttgga tgtcatggcc aaggagttct tcgccgactg a            2391
```

<210> SEQ ID NO 32
<211> LENGTH: 2298
<212> TYPE: DNA
<213> ORGANISM: Aspergillus terreus

<400> SEQUENCE: 32

```
atgctatcca cccagcaccg aaattcgcat gaccggcacc ggcaacatcg aaggcagatt      60
tccacccctt ctgccattga cgccgcgaaa gctccctccc tgccggcgca ggcattgcat     120
cgataccatg ctcatcgccg aggccagagt ttcgaccaac gatctctaca tgttcaacga     180
ccgcagacca tgcacgatgg taacgtttca gctactaaca cacaggacc gcagacggtg      240 atgggagaag tgcagcagct gcaacgtttc ggacccacag acactcagg ctatcaccaa      300 cactcggctt ctatgccggt aatgcccgag tgccaaccat tgagcagga agacttccag      360 accctgggca atcgcaatgt cccagacaac cagaccgcca tgacctatat gacgcccgcg     420
ctgcacctca acatgatgca gcagcagcag cagcttcaac acgcaagagt gcattccaac     480
aatgcgcttg atggtcagct tctcgagaat ggtccgtggg acatgtatca gcacgacaac     540
cttgctgcgc cgctcccaca gcaacccaac accattcccg cgggcttaag gcgtctgtca     600
gctcaatcag agaccactcc tgcgcaacga ccactcactc cgaagcataa caataccaat     660
taccttccta tcacccctgc cacaacgccc tttaaaaaat cagtggatct tgcccagtac     720
agcggcgaac tccattcaac tcccaccaag gaccagagcc tttccgcacc cggctcttcc     780
caatcgttca tgcaacgtac gaattcactc caaggagtgg ctggaacaac attctcccaa     840
cccaagcttg aagtccctc ccccccaaac actgcgtcat tgatgtgga cagcttcgat       900 gcttttgact atcaacagga atccagttat gaaatcccca gtctgagag cctcaaccat      960 tatgcctcgt cgttggcgtc gtcatcattc aactcatccc cggaactcgc ggctatgccg    1020
tgtccacaag acggcggtag agcgcaaaag ctccccatct acccggtcac accaagtcgc    1080
acaaacatga gaagtctcc cagcgtcacc tccaactcgt ccgcgtcgaa gccaaagctc     1140
tctccaaggg tcgcaaccat tgacagcctc aacctggatg ccagagtcca tgcatccatc    1200
aaagaaactg gcgtcacaat cgacgagatt gcctcgtaca taagcggccc tgatccagag    1260 gacgaaaat gggtgtgtct gcacccagga tgcgagcgtc ggtttggaag aaaagaaaac    1320
atcaagtccc atgttcagac ccatctgggt gaccgtcagt acaagtgcga ccactgcaac    1380
aaatgttttg tccgcggcca cgatctcaaa cgccatgcca aaatccatac cggtgacaag    1440
ccgtacgagt gtctctgcgg taatgtgttc gctcgacacg acgcattgac gcgccaccga    1500
caacggggca tgtgcatcgg tggttacaag ggaatcgttc gcaagacaac gaaacgtggt    1560
cgccccaaga acatcggcc cgagatggac gagagacaag ataaggcatc tagaacccgc    1620
cagcggctcg ccgagaagac atctttcgac tcctccagct cagatatctc tcgcaattct    1680
cccccatcgg aggtactgga caaatgagc cttcacggct ctagcccgc cgaacagatg      1740 ccggtattcc ataatccaaa ctactcgctg cctccggagg tctttacgtt cactcctcct    1800
gcatcccctg gcggtagcgc tggaaacaac ccttctccaa gccacagcca acgctccctc    1860
```

```
acgcctagca ccgaggacga aatgccacct ttgtcacctt ccaagcaacc tctgtcaaag    1920
attgtggaag aatctggctt gcctcttatg cccgattgtg catacaccaa tgccaccaac    1980
tcaaccatca atgctttgtc gtccccgcat accgcaccca ccctgagtga tgcttcaaac    2040
ggctccgatc ttgacatctt tatcagccaa gatccgtcca ccggcttcgg caagcatgag    2100
ttttccgacc tcactgattc cgacatggcg gcattccctg actatgtgaa cggctcttcc    2160
ttcgaaggcg aatggacct cttccaagga aaggggttct ccaatgctcc cccaatgagc    2220
gacgacttct tctccttcca atttcaagtt gacgagcaac catccgatgt tatgacccgc    2280
gatttcttca tggattaa                                                  2298

<210> SEQ ID NO 33
<211> LENGTH: 2316
<212> TYPE: DNA
<213> ORGANISM: Aspergillus niger

<400> SEQUENCE: 33
atgctgtcca cggcgcacag caaccttcat gagcgacatc gacaacacag gcggcagatc     60
tcgacgccgt ccgctcttga tgccgtgaaa gcccccagcc ttccggcgca agcgatgcat    120
cgttatcatg cccatcgtcg aggacagagt tttgacaaca gagctttgcg cgtccagcga    180
tcgcaatcca tgcaagatgg tacaaatcat actactaact ctacagtacc gcagcagcac    240
cattcgaata tgctcgggga cagccaacac caacgatacc tgtgtgtagc gcagccgtcg    300
tttccccagc aatcagcccc catgcccgtg atccccgact gtttcacccc ggaagaggtg    360
caaaaccttc aaagtcacaa tggccaggac agtcaaccaa gcatggccta cctgaatgcg    420
cccttcgcaa aggacgttcc gcacatgaac atgcagttcg acctgatgca acaacaacag    480
atgcacagca ctaaggttcc gtgcgggtct ggaacggaag gtcattttt cgagacggga    540 ctttgggact tttaccagcc aactttcccc cctcacgctg atgtaaggaa gttatcggtg    600
cagtcggatg ctactccgtc tcagcacccg catacgccta agcacggcaa tacacagtat    660
gccccgatta caccagcaac aacaccattc aagcaaaccg tgggcctagc tcagtacggt    720
ggggacatcc agtcaggatc caccaaagat cagggtagcg cgatgcccgg atcagcccag    780
tcgtcgtaca tgcagcgagc aaagtctctc caaggcgtgg ctggaactac tttcacgcag    840
cagaagtttg atgtttctac cccccgaac acagcatcat tgaagtgga taactttgat    900 acttttaact atgagcaggg ttctagcttt gaggttccta aatcggaaag tctgtcacaa    960
agccagtatg catcgtcgtc gtcggcatca tcatcatcct tcatgtcatc tcccgagctt   1020
gcggctatgc cttgccccga agatggaggt gcaaagaccc ccaaaatccc tatctatccc   1080
gccactccca gccgtccgca tcacagaaag acgcccagtg caacacctag ctcatcggcc   1140
aagccaaagc tttctccgcg cgttgcgtct atcgataacc tgaacctcga cgctcgcgtg   1200
caagcatcaa tcaaagaaac gggtgtcacc attgacgaga ttgcttcgta cattcatggg   1260
cctgacccgg aggacgggaa atgggtatgc ctgcaccccg gctgcgagcg ccgcttttgga   1320 agaaaggaga atatcaagtc acatgtccag actcacctgg gcgaccgcca gtacaagtgc   1380
gatcattgca acaaatgctt tgttcgcggt catgaccta agcgtcatgc taagatccat   1440
accggcgaca agccttacga gtgcctctgt ggaaatgtat ttgcgagaca cgacgccttg   1500
actcgacaca gacagcgggg tatgtgcatt ggcggctaca agggcattgt gcgcaagaca   1560
acgaaacggg gtcgtccgaa gaagcaccga ccagagatgg atgagagaca ggacaaagca   1620
```

```
tcgagaacgc gtcagaggat tgcagagaag tcatctttcg actcgtccac atccgagtcc   1680
tcacgcaaca cgcctccttc cgaagtcttc gaaaacatga gcctgcatgg ttctagcccg   1740
gcggaagaga tgccagtgtt caacaacccc aactactcgt tgccaccaga ggttttcaca   1800
ttcacgcctc ctgcatctcc cggttacagc gtgggaatca agccatcgcc ttctcgggac   1860
gagcgatcga tcaccccag ctcagaagat gaaatgcttc cttcctcacc atcaaagcag   1920
cacctcgaga gcctcgtcac agactccagc ttgccttaca tgtctgatcc ggagacatgc   1980
ccgtatacag atgcttccgg cgctgctagc cattctctat cttcacccca tgccgctccc   2040
accctgtccg aatcatctaa cggctctgat ctcgacattt ttattagcca ggattcgacc   2100 tctggtttg gaaagcccga attcggagac ctggctgatc ccgacatggc cccgttccca   2160
gactatgtga acacgacgtc ctttgaaggt ggtctggaac tgttccccaa caagcccttc   2220
tcctcgggcc ccgtcatggc cgacgacttc ttcttccaat ttcaagtgga cgaacaagcc   2280
tcggatgtta tgactaaaga attcttcatg gactaa                              2316

<210> SEQ ID NO 34
<211> LENGTH: 2226
<212> TYPE: DNA
<213> ORGANISM: Aspergillus nidulans

<400> SEQUENCE: 34
atgctttcta atccacaaag tacccttcac gggcgccatc gtcaacatcg acggcagatc     60
tcgactccct ccgcgctcga tgccgtaaaa ccccaggcc tttctccaca ggctctgcag    120
agatatcatg ctcatcgccg cggccaaagt ctggaccagc gagctgtaca agctcaagct    180
cagcgacaac agctcgtgca agatgcgtca agtactaacc aaacagcacc gcaattcgcg    240
cctaactcaa ccctcgtccc cttaattcct gactcccaga tcttcggcca agacgacatg    300
caggcttcaa gtcacgccaa ttaccagacg cctcacagcc taccctactt gcacacgaat    360
tttgtcaagg ccgatgatca ggctcgggat gctcgacctg tcaatcacca tctcaatctc    420
attcaacagc agcagcaaca actgcacaat gctaagctca actgccacga tacacacgat    480
gatcagctgc tcgacaacga cgcgtgggat acatacaaac ccgacatcgc gtcctcgctt    540
caacaaacga ccaccgatat gagacgacaa tctgtccatt caaacccaag tagctcatac    600
catccgcaca ctccgaaaaa aacaaactca ccaacgacgc cgttcgacaa aacagatttt    660
gctcagtact gcgcggagac gcaaatcgtc ccagcaaaag accaaaatgc tgctgatgcc    720
agctcccagt cggcctatat gcaacgcgcc aagtcccttc aaggagtagc ggggactagc    780
ttctcacagc aaaagattga aatgccctct cccctagca ctgattcgtt tgcagttgat    840
ggttttgata cgtttgacta ccagcagtgt tccagtttg ataacctcgc taccaccagc    900
cacagccagt actctacgtc gtccaactca ccagaagtcg ctgccattcc aagctctgga    960
gatcacaccg aaaagaagtc caagctccct atttgtcctg ccacgccag ccgtctcagc   1020 ccaaggaaac agctcgctac gccaagcgcg gcttctttag tgaaggcaaa actttctccg   1080
cgtgtcgcat ctatcgataa cctcaacctg gactcccggg tgcatgcctc tatcaaagaa   1140
actggtgtta gcattgatga aatagcgtcc tatatccacg gtccagaccc cgaagacgga   1200
aagtgggtgt gcctgcaccc cggctgtgag cgacgctttg gccgcaagga aacatcaag   1260 tcacatgtgc aaacccacct aggtgatcgc cagtacaagt gcgatcattg tgataagtgt   1320
ttcgttcgtg gcatgatct gaagcgccac gcgaagatcc acacaggaga caagccgtac   1380
gaatgtctat gcggtaatgt ttttgcccgg cacgatgccc taactcggca ccgccagagg   1440
```

| ggaatgtgca ttggtggtta caagggaatt gtgcgtaaga caacgaaacg tggccgtcct | 1500 |
| aagaagcacc gcccagagat ggatgagaga cgtgacaagg caaccaagac ccgacagagg | 1560 |
| atcgctgaga atcattatt caattcttcc gaatcggaca cttctcgtcg tacgccgccc | 1620 |
| tcggaggtgt tgagaacat gagccttcat ggctccagct cagcagacga gatggtgaca | 1680 |
| tttgacagcc aaaattactt gccgccagaa gtgttcactt tcactccgcc cgaatctcca | 1740 |
| aattacggta cagcaagcaa gcctgccagc ccgcgatctc tcacgccgag ctccgaagac | 1800 |
| gagatgctac ctttgtcatc atccaaacga ccactggaaa acattcttga gcattcgggc | 1860 |
| ctccccttc tcactgatgc cggcacatgc tctttctcct ctgttcaag ttcaagcagc | 1920 |
| catgcactat cttctccgca caccgcgcct accctaagcg acccttcgca accatccgat | 1980 |
| ctcgatatct tcatcaacag tgaaccttcc tctgcctttg gcaaacaaga tttcggcttg | 2040 |
| ggtgattcgg acatggctgc attcccagac tacgtcaacg gctctgcgtt tgacagcagc | 2100 |
| ttggatttgc tccaagggaa gaatttctcc acagggccct ctatgggcga tgacttcttt | 2160 |
| tccttccagt tccaagtcga cgaacaagcg tcggacgtca tgtcaaggga gttttttcctc | 2220 |
| gactaa | 2226 |

<210> SEQ ID NO 35
<211> LENGTH: 2316
<212> TYPE: DNA
<213> ORGANISM: Aspergillus oryzae

<400> SEQUENCE: 35

| atgttatcga acccacatcg caatctacag gaacgacatc gacaacatcg gcggcagatt | 60 |
| tcaacacctt ccgctcttga tgccgccaaa gtccccagtc ttcctgccca ggcaatgcac | 120 |
| cgataccatg ctcaccgtcg cggccagagc ctagaccaga ggtctctaca catgcaacga | 180 |
| tcgcagaccg tgcaagatgg taaccttcta aatactaacg caacaggtcc cctggtaatg | 240 |
| caacagcaac actatgctcg ttcggcgcaa ccgacaccca tgcccatgat gcctgagtgc | 300 |
| cagactttca gtcctgaaga attgcaaacc caaccaagta tgggatacat gagcccagcc | 360 |
| ttcgccaagg ccgagacccc ggcgctggag agtcggccga tgaacctcca tctcaatctg | 420 |
| attcagcaac agcagttgca gcaagcacac tcatggaga atggcgcttg ggatttctac | 480 |
| ccacacgaca acctcccaac gggacttccg caccagacca cgcaatccc tgcagatatg | 540 |
| agacgactat cagtgcagtc ggatgtcagt cccgcgcaaa gaccacatac gccgaaacct | 600 |
| gcacgtaagt gccctgatat tacttacagg agacaagccc cactgatgaa acttaaagac | 660 |
| taccttccca ttaccctgc gacaacacca ttcaagaaaa cagtggatct tgtgcagtat | 720 |
| ggtggcgaca tgcagccaac ccccaccaag gagcagagat tgtctgttcc cgtttcagcc | 780 |
| cagccgtcgt acatgcaacg tgctaagtct cttcaaggag tggctgggac gaccttctcc | 840 |
| cagcaaaaga ttgatatgcc ctctcccca aatacagcat ccttcgaggt ggatagtttc | 900 |
| gatgtgttta actgccagca gggttccagt tttgaaatgt caaagtctga agtttttca | 960 |
| tctagccact cttcaacatc gtcgtcgtca gcaacatccc ctttcaattc gtcaccagac | 1020 |
| cttgcctcca tgccgcacct tgcagacagt ggtaaggcgc agaagattcc tatttaccct | 1080 |
| gcaacaccta gccgtatgac tccaaagaag accccaagtg cgcccccgag ctcggccaaa | 1140 |
| cccaagcttt ctccaagggt agcatctatt gacagcctta atcttgacgc ccgggtccat | 1200 |
| gcctctatta aagaaactgg tgtcaccatt gacgagatag cgtcatacat tcatggccct | 1260 |

```
gacccagaag atggaaaatg ggtatgccta cacccggtt gcgaacgccg gttcggaagg    1320
aaagagaaca tcaagtccca tgtccaaaca catcttggag atcgccagta caagtgtgat    1380
cactgcgata aatgcttcgt ccgcggacac gaccttaagc gccacgccaa gatacatacc    1440
ggtgacaaac catatgaatg cctctgtggt aatgtgttcg cccgacatga tgccttgact    1500
cggcatcggc aacgcggcat gtgtattggc ggctacaagg gtatcgtgcg caagaccacc    1560
aaacgcggtc gtccgagaaa gcaccggcct gaaatggatg aaagacaaga gaaatcctcc    1620
aggacgcgcc agagaatcgc cgaaaagtcg tcatttgact cttctggatc agacacttcg    1680
cacaattcgc cgccctcgga agtcttcgaa aacatgagcc tgcagggttc tagtccggtg    1740
ggagaaatgc caatgttcag caatgttaat tattcattgc ccctgaggt cctgactttc    1800 acacctcccg cctctcctgg cggtagcata agaaacagac catcacctgc ccacagccag    1860
cgatcgatta cacccagcac tgaggatgaa atgccaccat tgtctccatc taaacgacct    1920
ctggaaagga tcattgaaga atccggtcta cctttaattt cggaccctga agcctgcccc    1980
tacacaaacg ctacaaactc aacaactcat gccctatctt ctccacacac cgtgcccact    2040
ttgaccgaat catcaaatgg ctcagaccta gacatcttca tcaaccaaga tccatctaca    2100
agcttcagca agcacgagtt ccctggctta accgaccctg acatggcggc attccctgat    2160
tacgtgaacg gtcccgcttt tgacaacggc atggatttgt ttcaaagcaa aggtttctct    2220
aacggtccct caatgagtga cgatttcttt gctttccagt tccagatgga cgaacaacca    2280
tcggacgtta tgacaaggga attcttcttg gagtga                             2316
```

<210> SEQ ID NO 36
<211> LENGTH: 13
<212> TYPE: DNA
<213> ORGANISM: Artificial Sequence
<220> FEATURE:
<223> OTHER INFORMATION: Primer

<400> SEQUENCE: 36
caacacaggc ggc                                                        13

<210> SEQ ID NO 37
<211> LENGTH: 17
<212> TYPE: DNA
<213> ORGANISM: Artificial Sequence
<220> FEATURE:
<223> OTHER INFORMATION: Primer

<400> SEQUENCE: 37
tctgttgttg ttgcatc                                                    17

<210> SEQ ID NO 38
<211> LENGTH: 15
<212> TYPE: DNA
<213> ORGANISM: Artificial Sequence
<220> FEATURE:
<223> OTHER INFORMATION: Primer

<400> SEQUENCE: 38
aacatcgaag gcaga                                                      15

<210> SEQ ID NO 39
<211> LENGTH: 16
<212> TYPE: DNA
<213> ORGANISM: Artificial Sequence
<220> FEATURE:
<223> OTHER INFORMATION: Primer

```
<400> SEQUENCE: 39
ctgcatcatg ttgagg                                                    16

<210> SEQ ID NO 40
<211> LENGTH: 14
<212> TYPE: DNA
<213> ORGANISM: Artificial Sequence
<220> FEATURE:
<223> OTHER INFORMATION: Primer

<400> SEQUENCE: 40
cgtcaacatc gacg                                                      14

<210> SEQ ID NO 41
<211> LENGTH: 17
<212> TYPE: DNA
<213> ORGANISM: Artificial Sequence
<220> FEATURE:
<223> OTHER INFORMATION: Primer

<400> SEQUENCE: 41
tgctgttgaa tgagatt                                                   17

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
ccgtctttga cctcagaaag a                                              21

<210> SEQ ID NO 43
<211> LENGTH: 14
<212> TYPE: DNA
<213> ORGANISM: Artificial Sequence
<220> FEATURE:
<223> OTHER INFORMATION: Primer

<400> SEQUENCE: 43
cccaattctc gcaa                                                      14

<210> SEQ ID NO 44
<211> LENGTH: 14
<212> TYPE: DNA
<213> ORGANISM: Artificial Sequence
<220> FEATURE:
<223> OTHER INFORMATION: Primer

<400> SEQUENCE: 44
ccggatgatt cgca                                                      14

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
tgcaacagca acactatgc                                                 19

<210> SEQ ID NO 46
```

```
<211> LENGTH: 14
<212> TYPE: DNA
<213> ORGANISM: Artificial Sequence
<220> FEATURE:
<223> OTHER INFORMATION: Primer

<400> SEQUENCE: 46
agaccgtgca agat                                                        14

<210> SEQ ID NO 47
<211> LENGTH: 16
<212> TYPE: DNA
<213> ORGANISM: Artificial Sequence
<220> FEATURE:
<223> OTHER INFORMATION: Primer

<400> SEQUENCE: 47
ggtttgcaat tcttca                                                      16

<210> SEQ ID NO 48
<211> LENGTH: 17
<212> TYPE: DNA
<213> ORGANISM: Artificial Sequence
<220> FEATURE:
<223> OTHER INFORMATION: Primer

<400> SEQUENCE: 48
cctgtgtgta gcgcagc                                                     17

<210> SEQ ID NO 49
<211> LENGTH: 13
<212> TYPE: DNA
<213> ORGANISM: Artificial Sequence
<220> FEATURE:
<223> OTHER INFORMATION: Primer

<400> SEQUENCE: 49
acagtaccgc agc                                                         13

<210> SEQ ID NO 50
<211> LENGTH: 13
<212> TYPE: DNA
<213> ORGANISM: Artificial Sequence
<220> FEATURE:
<223> OTHER INFORMATION: Primer

<400> SEQUENCE: 50
cttccggggt gaa                                                         13

<210> SEQ ID NO 51
<211> LENGTH: 22
<212> TYPE: DNA
<213> ORGANISM: Artificial Sequence
<220> FEATURE:
<223> OTHER INFORMATION: Primer

<400> SEQUENCE: 51
cgatctctac atgttcaacg ac                                               22

<210> SEQ ID NO 52
<211> LENGTH: 12
<212> TYPE: DNA
<213> ORGANISM: Artificial Sequence
<220> FEATURE:
<223> OTHER INFORMATION: Primer

<400> SEQUENCE: 52
```
cgaaagctcc ct                                                              12

<210> SEQ ID NO 53
<211> LENGTH: 12
<212> TYPE: DNA
<213> ORGANISM: Artificial Sequence
<220> FEATURE:
<223> OTHER INFORMATION: Primer

<400> SEQUENCE: 53
ccgtctgcgg tc                                                              12

<210> SEQ ID NO 54
<211> LENGTH: 21
<212> TYPE: DNA
<213> ORGANISM: Artificial Sequence
<220> FEATURE:
<223> OTHER INFORMATION: Primer

<400> SEQUENCE: 54
attccttgct ggaggagaac a                                                    21

<210> SEQ ID NO 55
<211> LENGTH: 15
<212> TYPE: DNA
<213> ORGANISM: Artificial Sequence
<220> FEATURE:
<223> OTHER INFORMATION: Primer

<400> SEQUENCE: 55
gcacgatggg accgt                                                           15

<210> SEQ ID NO 56
<211> LENGTH: 16
<212> TYPE: DNA
<213> ORGANISM: Artificial Sequence
<220> FEATURE:
<223> OTHER INFORMATION: Primer

<400> SEQUENCE: 56
gattgcgaga attggg                                                          16

<210> SEQ ID NO 57
<211> LENGTH: 18
<212> TYPE: DNA
<213> ORGANISM: Artificial Sequence
<220> FEATURE:
<223> OTHER INFORMATION: Primer

<400> SEQUENCE: 57
ccgattgcga gaattggg                                                        18

<210> SEQ ID NO 58
<211> LENGTH: 13
<212> TYPE: DNA
<213> ORGANISM: Artificial Sequence
<220> FEATURE:
<223> OTHER INFORMATION: Primer

<400> SEQUENCE: 58
acgatgggac cgt                                                             13

<210> SEQ ID NO 59
<211> LENGTH: 23
<212> TYPE: DNA

```
<213> ORGANISM: Artificial Sequence
<220> FEATURE:
<223> OTHER INFORMATION: Primer

<400> SEQUENCE: 59
gtctctacac atgcaacgat cgc                                           23

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
tgcattacca ggggacctgt t                                             21

<210> SEQ ID NO 61
<211> LENGTH: 25
<212> TYPE: DNA
<213> ORGANISM: Artificial Sequence
<220> FEATURE:
<223> OTHER INFORMATION: Primer

<400> SEQUENCE: 61
tgtgcaagat ggtaaccttc taaat                                         25

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
gaccatgcac gatggtaacg tt                                            22

<210> SEQ ID NO 63
<211> LENGTH: 19
<212> TYPE: DNA
<213> ORGANISM: Artificial Sequence
<220> FEATURE:
<223> OTHER INFORMATION: Primer

<400> SEQUENCE: 63
gtgggtccga aacgttgca                                                19

<210> SEQ ID NO 64
<211> LENGTH: 19
<212> TYPE: DNA
<213> ORGANISM: Artificial Sequence
<220> FEATURE:
<223> OTHER INFORMATION: Primer

<400> SEQUENCE: 64
agacggtgat gggagaagt                                                19

<210> SEQ ID NO 65
<211> LENGTH: 18
<212> TYPE: DNA
<213> ORGANISM: Artificial Sequence
<220> FEATURE:
<223> OTHER INFORMATION: Primer

<400> SEQUENCE: 65
atccatgcaa gatggtac                                                 18
```

```
<210> SEQ ID NO 66
<211> LENGTH: 18
<212> TYPE: DNA
<213> ORGANISM: Artificial Sequence
<220> FEATURE:
<223> OTHER INFORMATION: Primer

<400> SEQUENCE: 66
ctacacacag gtatcgtt                                                       18

<210> SEQ ID NO 67
<211> LENGTH: 16
<212> TYPE: DNA
<213> ORGANISM: Artificial Sequence
<220> FEATURE:
<223> OTHER INFORMATION: Primer

<400> SEQUENCE: 67
tgctcgggga cagcca                                                         16

<210> SEQ ID NO 68
<211> LENGTH: 414
<212> TYPE: DNA
<213> ORGANISM: Aspergillus fumigatus

<400> SEQUENCE: 68
tttcaacccc caatgcgctg gaagccgcca aagttcctac ccttccagca caggcattgc         60
agcgaatcaa tgcgcatcgc cgtggacaga gtctcgacca acgacctttg cacgatggga        120
ccgtttccat tactaacgca acagcaactc agcagcacca aatccttgct ggaggagaac        180
agcatcccca attctcgcaa tcggcacatt tcccccagca ctcctctccc atgcccgtga        240
tgcctgaatg cccgtctttg acctcagaag acttgcaagc attatccaat tctaccagca        300
atgcgaatca tccgggcatg gcttacatga attcgagctt cattgctatg gaaatccga         360 gcttgggact tcgaccaatg gataacaatc tgaatctgat gcaacagcaa cagc              414

<210> SEQ ID NO 69
<211> LENGTH: 414
<212> TYPE: DNA
<213> ORGANISM: Aspergillus fumigatus

<400> SEQUENCE: 69
tttcaacccc caatgcgctg gaagccgcca aagttcctac ccttccagca caggcattgc         60
agcgaatcaa tgcgcatcgc cgtggacaga gtctcgacca acgacctttg cacgatggga        120
ccgtttccat tactaacgca acagcaactc agcagcacca aatccttgct ggaggagaac        180
agcatcccca attctcgcaa tcggcacatt tcccccagca ctcctctccc atgcccgtga        240
tgcctgaatg cccgtctttg acctcagaag acttgcaagc attatccaat tctaccagca        300
atgcgaatca tccgggcatg gcttacatga attcgagctt ctttgctatg gaaatccga        360 gcttgggact tcgaccaatg gataacaatc tgaatctgat gcaacagcaa cagc              414

<210> SEQ ID NO 70
<211> LENGTH: 414
<212> TYPE: DNA
<213> ORGANISM: Aspergillus fumigatus

<400> SEQUENCE: 70
tttcaacccc caatgcgctg gaagccgcca aagttcctac ccttccagca caggcattgc         60
```

```
agcgaatcaa tgcgcatcgc cgtggacaga gtctcgacca acgacctttg cacgatggga      120
ccgtttccat tactaacgca acagcaactc agcagcacca aatccttgct ggaggagaac      180
agcatcccca attctcgcaa tcggcacatt tcccccagca ctcctctccc atgcccgtga      240
tgcctgaatg cccgtctttg acctcagaag acttgcaagc attatccaat tctaccagca      300
atgcgaatca tccgggcatg gcttacatga attcgagctt ctttgctatg ggaaatccga      360
gcttgggact tcgaccaatg gataacaatc tgaatctgat gcaacagcaa cagc            414
```

<210> SEQ ID NO 71
<211> LENGTH: 412
<212> TYPE: DNA
<213> ORGANISM: Aspergillus fumigatus

<400> SEQUENCE: 71

```
tttcaacccc caatgcgctg gaagccgcca aagttcctac ccttccagca caggcattgc       60
agcgaatcaa tgcgcatcgc cgtggacaga gtctcgacca acgacctttg cacgatggga      120
ccgtttccat tactaacgca acagcaactc agcagcacca aatccttgct ggaggagaac      180
agcatcccca attctcgcaa tcggcacatt tcccccagca ctcctctccc atgcccgtga      240
tgcctgaatg cccgtctttg acctcagaag acttgcaagc attatccaat tctaccagca      300
atgcgaatca tccgggcatg gcttacatga attcgagctt ctttgctatg ggaaatccga      360
gcttgggact tcgaccaatg gataacaatc tgaatctgat gcaacagcaa ca              412
```

<210> SEQ ID NO 72
<211> LENGTH: 414
<212> TYPE: DNA
<213> ORGANISM: Aspergillus fumigatus

<400> SEQUENCE: 72

```
tttcaacccc caatgcgctg gaagccgcca aagttcctac ccttccagca caggcattgc       60
agcgaatcaa tgcgcatcgc cgtggacaga gtctcgacca acgacctttg cacgatggga      120
ccgtttccat tactaacgca acagcaactc agcagcacca aatccttgct ggaggagaac      180
agcatcccca attctcgcaa tcggcacatt tcccccagca ctcctctccc atgcccgtga      240
tgcctgaatg cccgtctttg acctcagaag acttgcaagc attatccaat tctaccagca      300
atgcgaatca tccgggcatg gcttacatga attcgagctt cattgctatg ggaaatccga      360
gcttgggact tcgaccaatg gataacaatc tgaatctgat gcaacagcaa cagc            414
```

<210> SEQ ID NO 73
<211> LENGTH: 378
<212> TYPE: DNA
<213> ORGANISM: Aspergillus flavus

<400> SEQUENCE: 73

```
tttcaacacc ttccgctctt gatgccgcca aagtccccag tcttcctgcc caggcaatgc       60
accgatacca tgctcaccgt cgcggccaga gcctagacca gaggtctcta cacatgcaac      120
gatcgcagac cgtgcaagat ggtaaccttc taaatactaa cgcaacaggt ccctggtaa       180 tgcaacagca acactatgct cgttcggcgc aaccgacacc catgcccatg atgcctgagt      240
gccagacttt cagtcctgaa gaattgcaaa cccaaccaag tatgggatac atgagcccag      300
ccttcgccaa ggccgagacc ccggcgctgg agagtcggcc gatgaacctc catctcaatc      360
tgatgcaaca gcaacagc                                                   378
```

<210> SEQ ID NO 74
<211> LENGTH: 378
<212> TYPE: DNA
<213> ORGANISM: Aspergillus flavus

<400> SEQUENCE: 74

| | |
|---|---|
| tttcaacacc ttccgctctt gatgccgcca aagtccccag tcttcctgcc caggcaatgc | 60 |
| accgatacca tgctcaccgt cgcggccaga gcctagacca gaggtctcta cacatgcaac | 120 |
| gatcgcagac cgtgcaagat ggtaaccttc taaatactaa cgcaacaggt ccctggtaa | 180 |
| tgcaacagca acactatgct cgttcggcgc aaccgacacc catgcccatg atgcctgagt | 240 |
| gccagactt cagtcctgaa gaattgcaaa cccaaccaag tatgggatac atgagcccag | 300 |
| ccttcgccaa ggccgagacc ccggcgctgg agagtcggcc gatgaacctc catctcaatc | 360 |
| tgatgcaaca gcaacagc | 378 |

<210> SEQ ID NO 75
<211> LENGTH: 378
<212> TYPE: DNA
<213> ORGANISM: Aspergillus flavus

<400> SEQUENCE: 75

| | |
|---|---|
| tttcaacacc ttccgctctt gatgccgcca aagtccccag tcttcctgcc caggcaatgc | 60 |
| accgatacca tgctcaccgt cgcggccaga gcctagacca gaggtctcta cacatgcaac | 120 |
| gatcgcagac cgtgcaagat ggtaaccttc taaatactaa cgcaacaggt ccctggtaa | 180 |
| tgcaacagca acactatgct cgttcggcgc aaccgacacc catgcccatg atgcctgagt | 240 |
| gccagactt cagtcctgaa gaattgcaaa cccaaccaag tatgggatac atgagcccag | 300 |
| ccttcgccaa ggccgagacc ccggcgctgg agagtcggcc gatgaacctc catctcaatc | 360 |
| tgatgcaaca gcaacagc | 378 |

<210> SEQ ID NO 76
<211> LENGTH: 421
<212> TYPE: DNA
<213> ORGANISM: Aspergillus niger

<400> SEQUENCE: 76

| | |
|---|---|
| tcgacgccgt ccgctcttga tgccgtgaaa gccccagcc ttccggcgca agcgatgcat | 60 |
| cgttatcatg cccatcgtcg aggacagagt tttgacaaca gagctttgcg cgtccagcga | 120 |
| tcgcaatcca tgcaagatgg tacaaatcat actactaact ctacagtacc gcagcagcac | 180 |
| cattcgaata tgctcgggga cagccaacac caacgatacc tgtgtgtagc gcagccgtcg | 240 |
| tttccccagc aatcagcccc catgcccgtg atccccgact gtttcacccc ggaagaggtg | 300 |
| caaaaccttc aaagtcacaa tggccagaac agtcaaccaa gcatggccta cctgaatgcg | 360 |
| cccttcgcaa aggacgttcc gcacatgaac atgcagttcg acctgatgca caacaacag | 420 |
| a | 421 |

<210> SEQ ID NO 77
<211> LENGTH: 421
<212> TYPE: DNA
<213> ORGANISM: Aspergillus niger

<400> SEQUENCE: 77

| | |
|---|---|
| tcgacgccgt ccgctcttga tgccgtgaaa gccccagcc ttccggcgca agcgatgcat | 60 |
| cgttatcatg cccatcgtcg aggacagagc tttgacaaca gagctttgcg cgtccagcga | 120 |

```
tcgcaatcca tgcaagatgg tacaaatcat actactaact ctacagtacc gcagcagcac    180
cattcgaata tgctcgggga cagccaacac caacgatacc tgtgtgtagc gcagccgtcg    240
tttccccagc aatcagcccc catgcccatg atccccgact gtttcacccc ggaagaggtg    300
caaaaccttc aaagtcacaa tggccaggac agtcaaccaa gcatggccta cctgaatgcg    360
cccttcgcaa aggacgttcc gcacatgaac atgcagttcg atctgatgca acaacaacag    420
a                                                                    421
```

<210> SEQ ID NO 78
<211> LENGTH: 421
<212> TYPE: DNA
<213> ORGANISM: Aspergillus niger

<400> SEQUENCE: 78

```
tcgacgccgt ccgctcttga tgccgtgaaa gccccagcc ttccggcgca agcgatgcat      60
cgttatcatg cccatcgtcg aggacagagt tttgacaaca gagctttgcg cgtccagcga    120
tcgcaatcca tgcaagatgg tacaaaccat actactaact ctacagtacc gcagcagcac    180
cattcgaata tgctcgggga cagccaacac caacgatacc tgtgtgtagc gcagccgtcg    240
tttccccagc aatcagcccc catgcccgtg atccccgact gtttcacccc ggaagaggtg    300
caaaaccttc aaagtcacaa tggccaggac agtcaaccaa gcatggccta cctgaatgcg    360
cccttcgcaa aggacgttcc gcacatgaac atgcagttcg acctgatgca acaacaacag    420
a                                                                    421
```

<210> SEQ ID NO 79
<211> LENGTH: 421
<212> TYPE: DNA
<213> ORGANISM: Aspergillus niger

<400> SEQUENCE: 79

```
tcgacgccgt ccgctcttga tgccgtgaaa gccccagcc ttccggcgca agcgatgcat      60
cgttatcatg cccatcgtcg aggacagagt tttgacaaca gagctttgcg cgtccagcga    120
tcgcaatcca tgcaagatgg tacaaatcat actactaact ctacagtacc gcagcagcac    180
cattcgaata tgctcgggga cagccaacac caacgatacc tgtgtgtagc gcagccgtcg    240
tttccccagc aatcagcccc catgcccgtg atccccgact gtttcacccc ggaagaggtg    300
caaaaccttc aaagtcacaa tggccaggac agtcaaccaa gcatggccta cctgaatgcg    360
cccttcgcaa aggacgttcc gcacatgaac atgcagttcg acctgatgca acaacaacag    420
a                                                                    421
```

<210> SEQ ID NO 80
<211> LENGTH: 421
<212> TYPE: DNA
<213> ORGANISM: Aspergillus niger

<400> SEQUENCE: 80

```
tcgacgccgt ccgctcttga tgccgtgaaa gccccagcc ttccggcgca agcgatgcat      60
cgttatcatg cccatcgtcg aggacagagt tttgacaaca gagctttgcg cgtccagcga    120
tcgcaatcca tgcaagatgg tacaaatcat actactaact ctacagtacc gcagcagcac    180
cattcgaata tgctcgggga cagccaacac caacgatacc tgtgtgtagc gcagccgtcg    240
tttccccagc aatcagcccc catgcccgtg atccccgact gtttcacccc ggaagaggtg    300
caaaaccttc aaagtcacaa tggccaggac agtcaaccaa gcatggccta cctgaatgcg    360
```

```
ccattcgcaa aggacgttcc gcacatgaac atgcagttcg acctgatgca acaacaacag    420
a                                                                    421
```

<210> SEQ ID NO 81
<211> LENGTH: 383
<212> TYPE: DNA
<213> ORGANISM: Aspergillus terreus

<400> SEQUENCE: 81

```
tttccacccc ttctgccatt gacgccgcga aagctccctc cctgccggcg caggcattgc     60
atcgatacca tgctcatcgc cgaggccaga gtttcgacca acgatctcta catgttcaac    120
gaccgcagac catgcacgat ggtaacgttt cagctactaa caacacagga ccgcagacgg    180
tgatgggaga agtgcagcag ctgcaacgtt tcggacccac aggacactca ggctatcacc    240
aacactcggc ttctatgccg gtaatgcccg agtgccaacc attgagccag gaagacttcc    300
agaccctggg caatcgcaat gtcccagaca accagaccgc catgacctat atgacgcccg    360
cgctgcacct caacatgatg cag                                            383
```

<210> SEQ ID NO 82
<211> LENGTH: 383
<212> TYPE: DNA
<213> ORGANISM: Aspergillus terreus

<400> SEQUENCE: 82

```
tttccacccc ttctgccatt gacgccgcga aagctccctc cctgccggcg caggcattgc     60
atagatacca tgctcatcgc cgaggccaga gtttcgacca acgatctcta catgttcaac    120
gaccgcagac catgcacgat ggtaacgttt cagctactaa caactcagga ccgcagacgg    180
tgatgggaga agtgcagcag ctgcaacgtt tcggacccac aggacactca ggctatcacc    240
aacactcggc ttctatgccg gtaatgcccg agtgccaacc attgagccag gaagacttcc    300
agaccctggg caatcgcaat gtcccagaca accagaccgc catgacctat atgacgcccg    360
cgctgcacct caacatgatg cag                                            383
```

<210> SEQ ID NO 83
<211> LENGTH: 383
<212> TYPE: DNA
<213> ORGANISM: Aspergillus terreus

<400> SEQUENCE: 83

```
tttccacccc ttctgccatt gacgccgcga aagctccctc cctgccggcg caggcattgc     60
atcgatacca tgctcatcgc cgaggccaga gtttcgacca acgatctcta catgttcaac    120
gaccgcagac catgcacgat ggtaacgttt cagctactaa caacacagga ccgcagacgg    180
tgatgggaga agtgcagcag ctgcaacgtt tcggacccac aggacactca ggctatcacc    240
aacactcggc ttctatgccg gtaatgcccg agtgccaacc attgagccag gaagacttcc    300
agaccctggg caatcgcaat gtcccagaca accagaccgc catgacctat atgacgcccg    360
cgctgcacct caacatgatg cag                                            383
```

<210> SEQ ID NO 84
<211> LENGTH: 420
<212> TYPE: DNA
<213> ORGANISM: Neosartorya fischeri

<400> SEQUENCE: 84

```
tctccacccc caatgcgctg gaggccgcca aagttcctac ccttccagca caggcattgc    60
agcgaatcaa tgcgcatcgc cgtgggcaga gtcttgacca acgtcctcga cctatgcacg   120
atggggccgt ttccattact aacgcaacag caactcagca gtcccgaatc cttgccgggg   180
gagcgcatca tccccgattc tcgcaatcgg cgcattaccc tcaccattcc tctcccatgc   240
ctgtgatgcc tgaatgcccg tctctgactt cggaagactt ggaagcatta ccaattcta    300 ccagcaacgc gacccatcca ggcatggctt acatgaattc gagcttcgtt accatgggaa   360
acccgagctt ggggaatcga ccaatggata acaatctcaa tctgatgcaa cagcaacagc   420
```

<210> SEQ ID NO 85
<211> LENGTH: 420
<212> TYPE: DNA
<213> ORGANISM: Neosartorya fischeri

<400> SEQUENCE: 85

```
tctccactcc caatgcgctg gaggccgcca aagttcctac acttccagca caggcattgc    60
agcgaatcaa tgcgcatcgc cgtgggcaga gtctcgacca acgtcctcga cctatgcacg   120
atggggccgt ttccattact aacgcaacag caactcagca gtcccgaatc cttgccgggg   180
gagcgcatca tccccgattc tcgcaatcgg cgcatttccc tcagcattcc tctcccatgc   240
ctgtgatgcc tgaatgcccg tctctgacct cggaagactt ggaagcacta ccaattcta    300 ccagcaacgc gaacgatcca ggcatggctt acatgaattc gagcttcatt cccatgggaa   360
acccgagctt ggggaatcga ccaatggaca gcaatctcaa tctgatgcaa cagcaacagc   420
```

<210> SEQ ID NO 86
<211> LENGTH: 438
<212> TYPE: DNA
<213> ORGANISM: Neosartorya fischeri

<400> SEQUENCE: 86

```
tctcaacccc caatgcgctg gaagccgcca aagttcctac ccctccagca caggcattgc    60
agcgaatcaa tgcgcatcgc cgtggacaga gtctcgacca acgacctttg cacgtccgac   120
gtcctcgacc tatgcacgat ggggccgttt ccattactaa cgcaacagca actcagcaaa   180
cccaaatcct tgccggggga gcgcaacatc cccgattctc gcaatcggcg cattttcccc   240
agcattcctc tcccatgcct gtaatgcctg agtgcccatc tttgacctcg aagacttgc    300 aagcattgtc caattctacc agcaatgcga accatccggg catggcttac atgaattcga   360
gcttcattac catgggaaac ccgagcttgg ggatccgacc aatggacaac aatctcaatc   420
tgatgcaaca gcaacagc                                                 438
```

<210> SEQ ID NO 87
<211> LENGTH: 438
<212> TYPE: DNA
<213> ORGANISM: Aspergillus clavatus

<400> SEQUENCE: 87

```
tctcaacccc caatgtcctg gaagccgtca agtacctac tctcccggcg caggctttgc     60
agcgcatcca ggcgcatcgt cggggacaga gtctcgatca gcgatctgtg catgcccaac   120
gatctcgtcc catgcaagat ggtggtcctt ccattactaa cccagcagtg cctcagcaac   180
cccagatggt tgccggggga gcgcctcatc agcaattccc tcaatcgtcg caattccccc   240
agcaacttac ccccatgcct atgatgcccg aatgtcagtc gtttccctcc gacgagttgc   300
aggcgttgtc cggacagagc atcaacgtga atcaaccgga catggcttat atgattccag   360
```

```
acttcgtcaa catcggaaat cattgcgttg ggaaccgacc catggtcagc aacctcaatc    420
tgatgcaaca gcaacagc                                                  438

<210> SEQ ID NO 88
<211> LENGTH: 438
<212> TYPE: DNA
<213> ORGANISM: Aspergillus clavatus

<400> SEQUENCE: 88
tctcaacccc caatgtcctg aagccgtca aagtacctac tctcccggcg caggctttgc      60
agcgcatcca ggcgcatcgt cggggacaga gtctcgatca gcgatctgtg catgcccaac    120
gatctcgtcc catgcaagat ggtggtcctt ccattactaa cccagcagtg cctcagcaac    180
cccagatggt tgccggggga gcgcctcatc agcaattccc tcaatcgtcg caattccccc    240
agcaacttac ccccatgcct atgatgcccg aatgtcagtc gtttccctcc gacgagttgc    300
aggcgttgtc cggacagagc atcaacgtga atcaaccgga catggcttat atgattccag    360
acttcgtcaa catcggaaat cattgcgttg ggaaccgacc catggtcagc aacctcaatc    420
tgatgcaaca gcaacagc                                                  438

<210> SEQ ID NO 89
<211> LENGTH: 438
<212> TYPE: DNA
<213> ORGANISM: Aspergillus clavatus

<400> SEQUENCE: 89
tctcaacccc caatgtcctg aagccgtca aagtacctac tctcccggcg caggctttgc      60
agcgcatcca ggcgcatcgt cggggacaga gtctcgatca gcgatctgtg catgcccaac    120
gatctcgtcc catgcaagat ggtggtcctt ccattactaa cccagcagtg cctcagcaac    180
cccagatggt tgccggggga gcgcctcatc agcaattccc tcaatcgtcg caattccccc    240
agcaacttac ccccatgcct atgatgcccg aatgtcagtc gtttccctcc gacgagttgc    300
aggcgttgtc cggacagagc atcaacgtga atcaaccgga catggcttat atgattccag    360
acttcgtcaa catcggaaat cattgcgttg ggaaccgacc catggtcagc aacctcaatc    420
tgatgcaaca gcaacagc                                                  438

<210> SEQ ID NO 90
<211> LENGTH: 370
<212> TYPE: DNA
<213> ORGANISM: Aspergillus nidulans

<400> SEQUENCE: 90
cgactccctc cgcgctcgat gccgtaaaac cccaggcct ttctccacag gctctgcaga      60
gatatcatgc tcatcgccgc ggccaaagtc tggaccagcg agctgtacaa gctcaagctc    120
agcgacaaca gctcgtgcaa gatgcgtcaa gtactaacca aacagcaccg caattcgcgc    180
ctaactcaac cctcgtcccc ttaattcctg actcccagat cttcggccaa gacgacatgc    240
aggcttcaag tcacgccaat taccagacgc ctcacagcct accctacttg cacacgaatt    300
ttgtcaaggc cgatgatcag gctcgggatg ctcgacctgt caatcaccat ctcaatctca    360
ttcaacagca                                                           370

<210> SEQ ID NO 91
<211> LENGTH: 370
<212> TYPE: DNA
```

<213> ORGANISM: Aspergillus nidulans

<400> SEQUENCE: 91

| | |
|---|---|
| cgactccctc cgcgctcgat gccgcaaaac ctccaggcct ttctccacag gctctgcaga | 60 |
| gataccatgc tcatcgccgc ggccaaagtc tggaccagcg agctgtgcaa gctcaagctc | 120 |
| agcgacaaca gctcgtgcaa gatgcgtcaa gtactaacca aacagcaccg caattcgcgc | 180 |
| ctaactcaac cctcgtccct ttaatgcctg actcccagat cttcggccaa gacgacatgc | 240 |
| aggcttcaag tcacgccaat taccagacgc ctcacagtct accctacttg cacacgaact | 300 |
| ttgtcaaggc cgatgatcag gctcgggatg ctcgacctgt caatcaccac ctcaatctca | 360 |
| ttcaacagca | 370 |

<210> SEQ ID NO 92
<211> LENGTH: 370
<212> TYPE: DNA
<213> ORGANISM: Aspergillus nidulans

<400> SEQUENCE: 92

| | |
|---|---|
| cgactccctc cgcgctcgat gccgtaaaac ccccaggcct ttctccacag gctctgcaga | 60 |
| gatatcatgc tcatcgccgc ggccaaagtc tggaccagcg agctgtacaa gctcaagctc | 120 |
| agcgacaaca gctcgtgcaa gatgcgtcaa gtactaacca aacagcaccg caattcgcgc | 180 |
| ctaactcaac cctcgtcccc ttaattcctg actcccagat cttcggccaa gacgacatgc | 240 |
| aggcttcaag tcacgccaat taccagacgc ctcacagcct accctacttg cacacgaatt | 300 |
| ttgtcaaggc cgatgatcag gctcgggatg ctcgacctgt caatcaccat ctcaatctca | 360 |
| ttcaacagca | 370 |

<210> SEQ ID NO 93
<211> LENGTH: 370
<212> TYPE: DNA
<213> ORGANISM: Aspergillus nidulans

<400> SEQUENCE: 93

| | |
|---|---|
| cgactccctc cgcgctcgat gccgcaaaac ctccaggcct ttctccacag gctctgcaga | 60 |
| gataccatgc tcatcgccgc ggccaaagtc tggaccagcg agctgtgcaa gctcaagctc | 120 |
| agcgacaaca gctcgtgcaa gatgcgtcaa gtactaacca aacagcaccc caattcgcgc | 180 |
| ctaactcaac cctcgtccct ttaatgcctg actcccagat cttcggccaa gacgacatgc | 240 |
| aggcttcaag tcacgccaat taccagacgc ctcacagtct accctacttg cacacgaact | 300 |
| ttgtcaaggc cgatgatcag gctcgggatg ctcgacctgt caatcaccac ctcaatctca | 360 |
| ttcaacagca | 370 |

<210> SEQ ID NO 94
<211> LENGTH: 418
<212> TYPE: DNA
<213> ORGANISM: Aspergillus glaucus

<400> SEQUENCE: 94

| | |
|---|---|
| tctcgcaacc ctacagccct cgaggccgcg aaagttccca gtctccctgc accggcattg | 60 |
| caacggctca atgctcatcg acgaggccag agcctcgaca cacgggcctt ccagatgcaa | 120 |
| caacgagcac aggccatgca ggatgggaat ctttcttttta ctaaccaagg aacagtacac | 180 |
| caacaaccaa aaccacacaa tgtccttgcg cgaggcccaac aacagcgatt ggctagacag | 240 |
| ggacatcaga tgtatcccgc taattcaaca tctgtacccc tgatgcccga ctgccacgcg | 300 |

```
ttcagccaag gggacctgca tatgcctgcg aaccaagaca acaatgagaa ccaccaaagc    360
gcggcgtata ttgaagcaca gctgaatctg aacttcaatc tgatgcaaca gcaacagc     418

<210> SEQ ID NO 95
<211> LENGTH: 418
<212> TYPE: DNA
<213> ORGANISM: Aspergillus glaucus

<400> SEQUENCE: 95
tctcgcaacc ctacagccct cgaggccgcg aaagttccca gtatccctgc accggcattg     60
caacggctca atgctcatcg acgaggccag agcctcgaca cacgggcctt ccagatgcaa    120
caacgagcac aggccatgca ggatgggaat ctttctttta ctaaccaagg aacagtacac    180
caacaaccac aaccacacaa tgtcttgcgc gaggtccaac aacagcgatt ggctagacag    240
ggacatcaga tgtatcccgc taattcaaca tctgtacccc tgatgcccga ctgccacgcg    300
ttcagccaag gggacctgca tatgcctgcg aaccaagaca acaatgagaa ccaccaaagc    360
gcggcgtata ttgaagcaca gctgaatctg aacttcaatc tgatgcaaca gcaacagc     418
```